United States Patent
Sawa et al.

(10) Patent No.: US 10,538,521 B2
(45) Date of Patent: Jan. 21, 2020

(54) PYRIMIDINE DERIVATIVE HAVING ANTIMALARIAL ACTIVITY

(71) Applicants: CARNA BIOSCIENCES, INC., Hyogo (JP); THE KITASATO INSTITUTE, Tokyo (JP)

(72) Inventors: Masaaki Sawa, Ibaraki (JP); Yuko Asamitsu, Kobe (JP); Yuko Uno, Amagasaki (JP); Satoshi Omura, Tokyo (JP); Kazuhiko Otoguro, Yokohama (JP); Masato Iwatsuki, Tokyo (JP); Aki Ishiyama, Tokyo (JP); Rei Hokari, Fuchu (JP)

(73) Assignees: CARNA BIOSCIENCES, INC., Hyogo (JP); THE KITASATO INSTITUTE, Tokyo (JP)

( * ) Notice: Subject to any disclaimer, the term of this patent is extended or adjusted under 35 U.S.C. 154(b) by 0 days.

(21) Appl. No.: 16/344,471

(22) PCT Filed: Oct. 25, 2017

(86) PCT No.: PCT/JP2017/038588
§ 371 (c)(1),
(2) Date: Apr. 24, 2019

(87) PCT Pub. No.: WO2018/079629
PCT Pub. Date: May 3, 2018

(65) Prior Publication Data
US 2019/0345154 A1 Nov. 14, 2019

(30) Foreign Application Priority Data
Oct. 26, 2016 (JP) .................................. 2016-209766

(51) Int. Cl.
*C07D 471/04* (2006.01)
*A61P 33/06* (2006.01)
*A61K 31/506* (2006.01)

(52) U.S. Cl.
CPC .......... *C07D 471/04* (2013.01); *A61K 31/506* (2013.01); *A61P 33/06* (2018.01)

(58) Field of Classification Search
CPC .............. C07D 471/04; C07D 491/056; C07D 491/107; A61K 31/506; A61K 31/5377; A61P 33/06
See application file for complete search history.

(56) References Cited

U.S. PATENT DOCUMENTS

2017/0050951 A1   2/2017   Hameed Peer Mohamed et al.

FOREIGN PATENT DOCUMENTS

| WO | 2015/165660 | 11/2015 |
| WO | 2016/175264 | 11/2016 |

OTHER PUBLICATIONS

International Search Report dated Jan. 16, 2018 in International Application No. PCT/JP2017/038588.
International Preliminary Report on Patentability dated May 9, 2019 in International Application No. PCT/JP2017/038588, with English translation.
Hameed et al., "Triaminopyrimidine is a fast-killing and long-acting antimalarial clinical candidate", Nature Communications, 6: 6715, 2015.
Deng et al., "Discovery of novel 1H-imidazol-2-yl-pyrimidine-4,6-diamines as potential antimalarials", Bioorganic & Medicinal Chemistry Letters, 20: 4027-4031, 2010.

*Primary Examiner* — Deepak R Rao
(74) *Attorney, Agent, or Firm* — Wenderoth, Lind & Ponack, L.L.P.

(57) ABSTRACT

The present invention provides a novel 2,4,6-substituted pyrimidine derivative, which is a compound represented by formula (I) (in the formula, ring A is a 6-membered heteroaryl group having at least one N atom optionally substituted with R1, R2, and R3; Z is an optionally substituted alkoxy group, an optionally substituted amino group, an optionally substituted heterocycloalkyl group, or an optionally substituted heteroaryl group; and R1, R2, and R3 are each independently selected from the group consisting of a hydrogen atom, a halogen atom, an optionally substituted alkyl group, an optionally substituted cycloalkyl group, an optionally substituted alkoxy group, an optionally substituted cycloalkyloxy group, an optionally substituted heterocycloalkyloxy group, an optionally substituted phenoxy group, an optionally substituted amino group, a nitro group, and a hydroxy group) or a pharmaceutically acceptable salt thereof.

6 Claims, No Drawings

PYRIMIDINE DERIVATIVE HAVING ANTIMALARIAL ACTIVITY

TECHNICAL FIELD

The present invention relates to a novel pyrimidine derivative, more specifically to a 2,4,6-substituted pyrimidine derivative. The present invention has an action of inhibiting the growth of *Plasmodium* species and thus can be useful for the treatment, prevention and/or inhibition of propagation of *Plasmodium* infection.

BACKGROUND ART

Malaria is a protozoan infection widely distributed in tropical to subtropical regions. About 80% of the patients with malaria is infected with *Plasmodium falciparum*, a *Plasmodium* species parasitic on humans, and this is a very dangerous infection causing death in serious cases. Furthermore, due to recent global warming, malaria is not only endemic in developing countries in tropical and subtropical regions but also seems to be spreading in developed countries in temperate regions.

For *Plasmodium* species parasitic on humans, chloroquine and fansidar (a drug combination of pyrimethamine and sulfadoxin), which are called a traditional drug and were developed in the 1930s to the 1960s, have been used. Later, artemisinin derivatives, an active ingredient of *Artemisia annua*, a herbal drug, was developed after the 1980s, and have been used.

However, *Plasmodium* resistant to chloroquine and/or fansidar and *Plasmodium* resistant to a multidrug containing those have emerged. There is also a report on the emergence of protozoa resistant even to artemisinin derivatives which was developed later.

In response to the emergence of such protozoa resistant to existing drugs, antimalarials effective for *Plasmodium* species have been developed worldwide. However, in the development of antimalarials, in many cases the antimalarial activity identified in vitro cannot be identified in vivo, or drugs are found to be toxic, and thus few drugs have been found to be effective for drug-resistant strains and have antimalarial activity in vivo.

Heretofore 2,4,5-substituted pyrimidine derivatives (Non patent document 1 and Patent document 1) and 2,4,6-substituted pyrimidine derivatives (Non patent document 2) have been reported as a substance having antimalarial activity, but no compounds are known to have the structure of the compound of the present invention.

PRIOR ART DOCUMENT(S)

Patent Document(s)

[Patent document 1] WO2015/165660

Non-Patent Document(S)

[Non-patent document 1] Shahul Hameed P. et al., Nat. Commun. 6:6715, 2015.

[Non-patent document 2] Xianming Deng, et al., Bioorg. Med. Chem. Lett. 20: 4027-4031, 2010.

DISCLOSURE OF INVENTION

Problem to be Solved by the Invention

An object of the present invention is to provide a novel compound which shows antimalarial activity even on *Plasmodium* species resistant to existing antimalarial.

Means for Solving Problem

The present inventors have conducted intensive studies to achieve the above object, and as a result have found that the compound represented by Formula (I), i.e., a 2,4,6-substituted pyrimidine derivative, and a pharmaceutically acceptable salt thereof (hereinafter may be referred to as "the compounds of the present invention") have the action of inhibiting growth of *Plasmodium*, and have completed the present invention. According to the present invention, propagation of infection with human infectious *Plasmodium* such as *Plasmodium falciparum, Plasmodium vivax* (*P. vivax*), *Plasmodium malariae* (*P. malariae*), *Plasmodium ovale* (*P. ovale*) and *Plasmodium knowlesi* (*P. knowlesi*) can be treated, prevented and/or inhibited.

The present invention includes following embodiments;

[1] A compound of the formula (I):

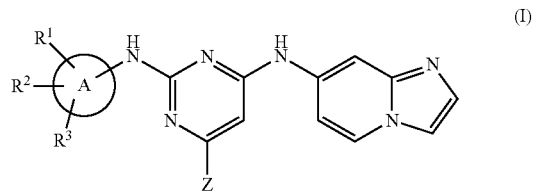

wherein the ring A is a 6-membered heteroaryl having one or more nitrogen atom(s) optionally substituted with $R^1$, $R^2$ and $R^3$, Z is an optionally substituted alkoxy group, an optionally substituted amino group, optionally substituted heterocycloalkyl group, or an optionally substituted heteroaryl group, and $R^1$, $R^2$ and $R^3$ are, each independently, selected from a group consisting of a hydrogen atom, a halogen atom, an optionally substituted alkyl group, an optionally substituted cycloalkyl group, an optionally substituted alkoxy group, an optionally substituted cycloalkyloxy group, an optionally substituted heterocycloalkyloxy group, an optionally substituted phenoxy group, an optionally substituted amino group, a nitro group, and a hydroxy group, or pharmaceutically acceptable salt thereof,

[2] The compound of the formula (I) according to [1] above, wherein the ring A is an optionally substituted 6-membered heteroaryl group containing a nitrogen atom, or pharmaceutically acceptable salt thereof,

[3] The compound of the formula (I) according to [1] above, wherein the ring A is an optionally substituted 6-membered heteroaryl group containing two nitrogen atoms, or pharmaceutically acceptable salt thereof,

[4] The compound according to [1] above, wherein the group of

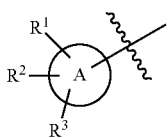

is a heteroaryl group selected from a group consisting of

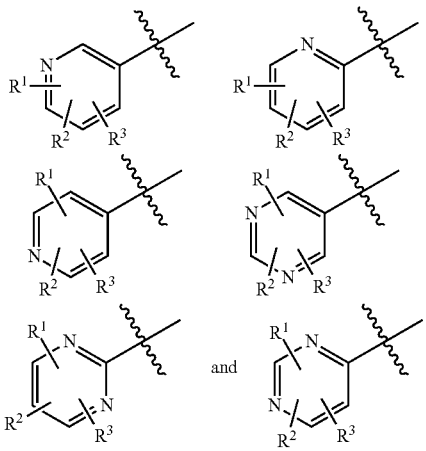

or pharmaceutically acceptable salt thereof,

[5] A compound of the general formula (I),

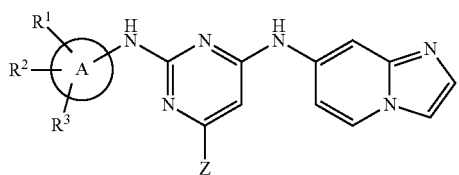

wherein the ring A is a heteroaryl group containing one or more nitrogen atom(s) optionally substituted with $R^1$, $R^2$ and $R^3$, Z is

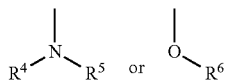

wherein $R^4$ and $R^5$ are, each independently a hydrogen atom, a $C_{1-6}$ alkyl group, a $C_{2-6}$ alkenyl group, a —$C_{0-4}$ alkylene-CO—$C_{1-6}$ alkyl group, a —$C_{1-4}$ alkylene-O—$C_{1-6}$ alkyl group, a —$C_{1-4}$ alkylene-NH—$C_{1-6}$ alkyl group, a —$C_{1-4}$ alkylene-NH—CO—$C_{1-6}$ alkyl group, a —$C_{1-4}$ alkylene-NH—COO—$C_{1-6}$ alkyl group, a —$C_{1-4}$ alkylene-N (the same or different $C_{1-6}$ alkyl)$_2$, —$C_{0-4}$ alkylene-COOH, a —$C_{0-4}$ alkylene-COO—$C_{1-6}$ alkyl group, —$C_{0-4}$ alkylene-CH=NH, a —$C_{0-4}$ alkylene-CH=N—$C_{1-6}$ alkyl group, —$C_{0-4}$ alkylene-SO$_2$H, a —$C_{0-4}$ alkylene-SO$_2$—$C_{1-8}$ alkyl group, a —$C_{0-4}$ alkylene-(5-, or 6-membered heterocycloalkyl group), a —$C_{0-4}$ alkylene-$C_{6-10}$ aryl group, or a —$C_{0-4}$ alkylene-(5-, or 6-membered heteroaryl group), wherein the alkyl group, the alkenyl group, the heterocycloalkyl group, the aryl group, the heteroaryl group and the alkylene group may be independently substituted on a carbon atom which can be substituted, with a substituent or two or more substituents, the same or different, selected from a group consisting of a halogen atom, a $C_{1-6}$ alkyl group, a $C_{1-6}$ haloalkyl group, a $C_{1-6}$ alkoxy group, a $C_{1-6}$ haloalkoxy group, a $C_{3-8}$ cycloalkyl group, a hydroxy group, a mercapto group, a cyano group, a nitro group, an amino group, a mono- or di-$C_{1-6}$ alkyl-amino group, a carboxyl group, a $C_{1-4}$ acyl group and a $C_{1-4}$ acylamino group, or $R^4$ and $R^5$ together with a nitrogen atom which they bound, may form a 3- to 12-membered heterocycloalkyl group or a 5- or 6-membered heteroaryl group, $R^6$ is a hydrogen atom, a $C_{1-8}$ alkyl group, a $C_{2-6}$ alkenyl group, a $C_{3-8}$ cycloalkyl group, a $C_{3-8}$ heterocycloalkyl group or a $C_{6-10}$ aryl group, each group may be substituted on a position which can be substituted, with a substituent or two or more substituents, the same or different, selected from a group consisting of a halogen atom, a $C_{1-6}$ alkyl group, a $C_{1-6}$ haloalkyl group, a $C_{1-6}$ alkoxy group, a $C_{1-6}$ haloalkoxy group, a $C_{3-8}$ cycloalkyl group, a hydroxy group, a mercapto group, a cyano group, a nitro group, an amino group, a mono- or di-$C_{1-6}$ alkyl-amino group, a carboxy group, a $C_{1-4}$ acyl group and a $C_{1-4}$ acylamino group, and $R^1$, $R^2$ and $R^3$ are independently selected from a group consisting of a hydrogen atom, a halogen atom, a $C_{1-6}$ alkyl group, a $C_{1-6}$ alkoxy group, an amino group, a mono- or di-$C_{1-6}$ alkyl-amino group, a nitro group, a hydroxy group, a $C_{3-6}$ cycloalkyl group, a $C_{3-6}$ cycloalkyloxy group, a 3- to 6-membered heterocycloalkyl group, a 3- to 6-membered heterocycloalkyloxy group, a phenoxy group and a $C_{1-4}$ acylamino group, each group may be substituted on a position which can be substituted, with a substituent, or two or more substituents, the same or different, selected from a group consisting of a halogen atom, a $C_{1-6}$ alkyl group, a $C_{2-6}$ alkenyl group, a $C_{1-6}$ haloalkyl group, a $C_{1-6}$ alkoxy group, a $C_{1-6}$ haloalkoxy group, a $C_{3-6}$ cycloalkyl group, a phenyl group, a hydroxy group, a mercapto group, a cyano group, a nitro group, an amino group, a mono- or di-$C_{1-6}$ alkyl-amino group, a carboxy group, a $C_{1-4}$ acyl group, a $C_{1-4}$ acylamino group and a 5- or 6-membered heterocycloalkyl group, or pharmaceutically acceptable salt thereof,

[6] The compound according to any of [1] to [5] above, wherein Z is selected from a group of amino, $C_{1-6}$ alkoxy, and

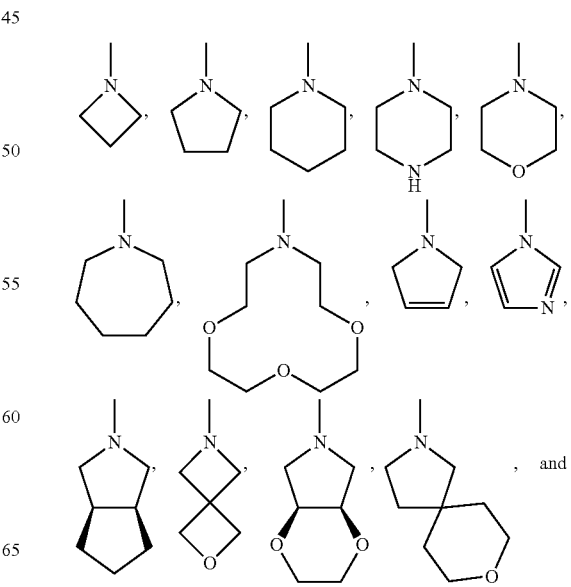

-continued

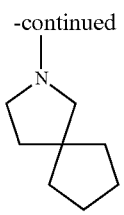

wherein each group may be substituted on a position which can be substituted, with a substituent, or two or more substituents, the same or different, selected from a group consisting of a halogen atom, a $C_{1-6}$ alkyl group, a $C_{1-6}$ haloalkyl group, a hydroxy group, a $C_{1-6}$ hydroxyalkyl group, a $C_{1-6}$ alkoxy group, an amino group, a mono- or di-$C_{1-6}$ alkyl-amino group, a carboxy group, a $C_{1-6}$ alkoxycarbonyl group, a 5- or 6-membered heterocycloalkyl group, a phenyl group, a benzyl group, and a 5- or 6-membered heteroaryl group, or pharmaceutically acceptable salt thereof.

[7] The compound according to any of [4] to [6], wherein the group of

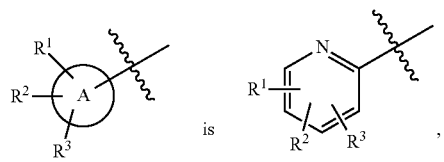

is two substituents of $R^1$, $R^2$ and $R^3$ are hydrogen atoms, and the remainder is selected from a halogen atom, a hydroxy group, a $C_{1-6}$ alkyl group, a $C_{1-6}$ alkoxy group, a $C_{3-6}$ cycloalkyloxy group, a 3- to 6-membered heterocyclo-alkyloxy group and a phenoxy group, which is linked to the pyridine at 2-, 4-, 5- or 6-position, and the $C_{1-6}$ alkyl group, $C_{1-6}$ alkoxy group, $C_{3-6}$ cycloalkyloxy group, 3- to 6-membered heterocyclo-alkyloxy group and phenoxy group may be substituted with one or more group(s), the same or different, selected from the group consisting of a halogen atom, a hydroxy group, a $C_{1-6}$ alkyl group, a $C_{2-6}$ alkenyl group, a $C_{1-6}$ alkoxy group, a phenyl group, an amino group, a mono-$C_{1-6}$ alkyl amino group or a di-$C_{1-6}$ alkyl amino group and a carboxy group, at a position which can be substituted, or pharmaceutically acceptable salt thereof.

[8] The compound according to any of [4] to [6], wherein the group of

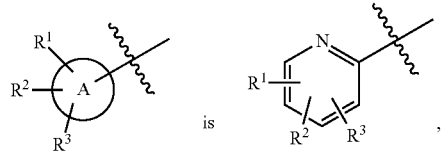

is one of $R^1$, $R^2$ and $R^3$ is a hydrogen atom, and the remainders are selected from a $C_{1-6}$ alkyl group and a $C_{3-6}$ cycloalkyl group, which are linked to the pyridine ring at 4- and 6-, or 5- and 6-positions, and the $C_{1-6}$ alkyl group and $C_{3-6}$ cycloalkyl group may be independently substituted with one or more group(s), the same or different, selected from the group consisting of a halogen atom, a hydroxy group, an amino group, and a mono-$C_{1-6}$ alkyl amino group or a di-$C_{1-6}$ alkyl amino group and a carboxy group, at a position which can be substituted, or pharmaceutically acceptable salt thereof.

[9] The compound according to any of [4] to [6], wherein the group of

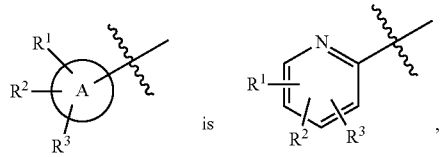

is two of $R^1$, $R^2$ and $R^3$ are hydrogen atoms, and the remainder is a halogen atom, a $C_{1-6}$ alkyl group, a nitro group, a $C_{1-6}$ alkoxy group or a $C_{3-6}$ cycloalkyl group, which is linked to the pyridine ring at 3-, 4-, 5- or 6-position, and the $C_{1-6}$ alkyl group, $C_{1-6}$ alkoxy group and $C_{3-6}$ cycloalkyl group may be substituted with one or more group(s), the same of different, selected from the group consisting of a halogen atom, a hydroxy group, a $C_{1-6}$ alkoxy group, an amino group, and a mono-$C_{1-6}$ alkyl amino group or a di-$C_{1-6}$ alkyl amino group and a carboxy group, at a position which can be substituted, or pharmaceutically acceptable salt thereof.

[10] The compound according to any of [4] to [6], wherein the group of

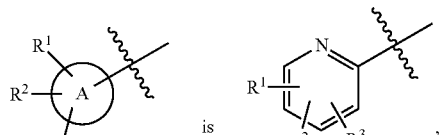

is $R^1$, $R^2$ and $R^3$ are independently selected from the group of a halogen atom, a $C_{1-6}$ alkyl group and a $C_{3-6}$ cycloalkyl group, which are linked to the pyridine ring at 4-, 5- and 6-positions, and the $C_{1-6}$ alkyl group and $C_{3-6}$ cycloalkyl group may be substituted with one or more group(s), the same of different, selected from the group consisting of a halogen atom, a hydroxy group, an amino group, and a mono- or di-$C_{1-6}$ alkylamino group and a carboxy group, at a position which can be substituted, or pharmaceutically acceptable salt thereof,

[11] The compound according to any of [4] to [6], wherein the group of

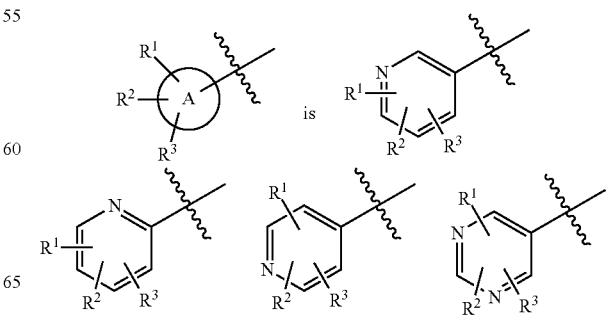

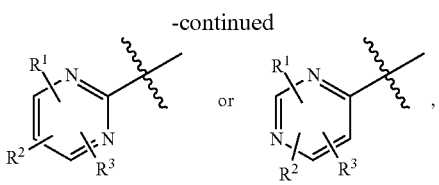

and
R¹, R² and R³ are hydrogen atoms,
or pharmaceutically acceptable salt thereof.

[12] A pharmaceutical composition comprising the compound according to any of [1] to [11] or a pharmaceutically acceptable salt thereof and a pharmaceutically acceptable carrier.

[13] A therapeutic agent for treating infection diseases of malaria *plasmodium*, comprising the compound according to any of [1] to [11] or a pharmaceutically acceptable salt thereof.

[14] Method for treating infection diseases of malaria *plasmodium* in a patient in need of such treatment, characterized in administrating a therapeutically effective amount of the compound according to any of [1] to [11] or a pharmaceutically acceptable salt thereof.

[15] The compound according to any of [1] to [11] or a pharmaceutically acceptable salt thereof for use in treating infection diseases of malaria *plasmodium*.

[16] Use of the compound according to any of [1] to [11] or a pharmaceutically acceptable salt thereof for manufacturing a medicine for treating infection diseases of malaria *plasmodium*.

[17] An inhibitor for proliferation of malaria *plasmodium* comprising the compound according to any of [1] to [11] or a pharmaceutically acceptable salt thereof.

[18] Method for inhibiting proliferation of malaria *plasmodium*, characterized in administrating a therapeutically effective amount of the compound according to any of [1] to [11] or a pharmaceutically acceptable salt thereof.

Effects of Invention

A compound of the present invention has an activity of inhibiting proliferation of malaria *plasmodium*, and is useful as a novel therapeutic agent, preventing and/or inhibiting agent for propagation of infection disease caused by malaria *plasmodium*. Also it is useful as a therapeutic agent, preventing and/or inhibiting agent for treating infection disease of malaria *plasmodium*, which is tolerant to known anti-malaria agents such as chloroquine and sulfadoxine/pyrimethamine (fansidar). Moreover, it is useful as a reagent of experimental or laboratory use for inhibiting proliferation of malaria *plasmodium*.

BEST MODE FOR CARRYING OUT THE INVENTION

Terms used in this specification are explained as follows;
"Halogen atom" means a fluorine atom, a chlorine atom, a bromine atom or an iodine atom. A fluorine atom, a chlorine atom and/or a bromine atom are preferable among them.

"Alkyl" or "alkylene" means a monovalent and divalent saturated hydrocarbon groups respectively, having a straight or branched carbon chain with pre-determined number of carbon atoms. It may be substituted with one or more substituent(s) included in this application, if necessary, at a position which can be substituted. Preferable examples of the alkyl include $C_{1-6}$ alkyl, $C_{1-4}$ alkyl and a lower alkyl. For example, "$C_{1-6}$ alkyl" means alkyl having 1 to 6 carbon atom(s), and "lower alkyl" means alkyl having 1 to 4 carbon atom(s). "Co alkylene" means a single bond, and "$C_{1-4}$ alkylene" means a divalent group having 1 to 4 carbon atom(s) such as methylene, ethylene, propylene and butylene etc. Non-limiting examples of alkyl include methyl, ethyl, propyl, isopropyl, butyl, isobutyl, tert-butyl, pentyl, isopentyl, neopentyl and hexyl etc.

"Alkenyl" means an unsaturated hydrocarbon group including one or more of carbon-carbon double bond(s), having a straight or branched carbon chain with pre-determined number of carbon atoms. It may be substituted with one or more substituent(s) included in this application, if necessary, at a position which can be substituted. Examples of preferred alkenyl include $C_{2-6}$ alkenyl or $C_{2-4}$ alkenyl. For example, "$C_{2-6}$ alkenyl" means alkenyl having 2 to 6 carbon atoms. Non-limiting examples of alkenyl include ethenyl, propenyl, butenyl, pentenyl, hexenyl etc.

"Haloalkyl" means the alkyl group defined above with pre-determined number of carbon atom(s), in which one or more of hydrogen atom(s) are replaced with halogen atoms. For example, "$C_{1-6}$ haloalkyl" means haloalkyl having 1 to 6 carbon atom(s). A range of numbers of replaced hydrogen atoms can be from 1 to the total number of hydrogen atoms existing in the parent alkyl group. The alkyl may be substituted with the same or different halogen atoms when two or more hydrogen atoms are substituted. Non-limiting examples of haloalkyl include chloromethyl, trifluoromethyl, 2,2,2-trifluoroethyl etc.

"Hydroxyalkyl" means hydroxy to which the alkyl defined above having predetermined number of carbon atoms were connected. The alkyl moiety may be substituted with one or more substituent(s) included in the present invention. Examples of the preferred hydroxyalkyl include $C_{1-6}$ hydroxyalkyl and $C_{1-4}$ hydroxyalkyl. For example, "$C_{1-6}$ hydroxyalkyl" means hydroxyalkyl having 1 to 6 carbon atom(s). Non-limiting examples of the hydroxyalkyl include hydroxymethyl and hydroxyethyl etc.

"Alkoxy" means a group in which the above defined alkyl with predetermined number of carbon atoms is connecting through an oxygen atom. The alkyl moiety may be substituted with one or more substituent(s) included in the present invention. Examples of the preferred alkoxy include $C_{1-6}$ alkoxy and $C_{1-4}$ alkoxy. For example, "$C_{1-6}$ alkoxy" means alkoxy (—O—$C_{1-6}$ alkyl) having 1 to 6 carbon atom(s). Non-limiting examples of alkoxy include methoxy, ethoxy, propoxy, isopropoxy, butyloxy, pentyloxy, isopentyloxy, neopentyloxy, hexyloxy etc.

"Haloalkoxy" means the above defined alkoxy with pre-determined number of carbon atoms, in which one or more hydrogen atom(s) are replaced with halogen atom(s). For example, "$C_{1-6}$ haloalkoxy" means haloalkoxy having 1 to 6 carbon atoms. A range of numbers of replaced hydrogen atoms can be from 1 to the total number of hydrogen atoms existing in the parent alkyl group. The alkoxy may be substituted with same or different halogen atoms when two or more hydrogen atoms are substituted. Non-limiting examples of haloalkoxy include chloromethoxy, trifluoromethoxy, 2,2,2-trifluoroethoxy etc.

"Cycloalkyl" means monocyclic or multicyclic saturated hydrocarbon having three or more carbon atoms, and it may be substituted with a substituent included in the present invention, if necessary, at a position which can be substituted. Examples of preferred cycloalkyl include $C_{3-10}$ cycloalkyl, $C_{3-8}$ cycloalkyl, and $C_{3-6}$ cycloalkyl. For example, "$C_{3-8}$ cycloalkyl" means cycloalkyl having 3 to 8 carbon atoms. Examples of cycloalkyl include cyclopropyl, cyclobutyl, cyclopentyl, cyclohexyl, cycloheptyl, and cyclooctyl etc. but they are not limited to these examples. Examples of multicyclic saturated hydrocarbon include bicyclic saturated hydrocarbon and tricyclic saturated hydrocarbon, and decahydronaphthalene, bicyclo[2.1.0]pentane, tricyclo[3.2.1.0$^{2,7}$]octane etc. are exemplified.

"Heterocycoalkyl" means the cycloalkyl defined above, in which at least one ring carbon is replaced with a heteroatom selected from the group consisting of a nitrogen atom, an oxygen atom and a sulfur atom, and it may be substituted with one or more substituent(s) included in the present invention, if necessary, at position(s) which can be substituted. Also, the nitrogen atom and/or the sulfur atom may be oxidized and the nitrogen atom may be quaternized, if necessary. In bicyclic heterocycloalkyl, one of the fused ring may contain only carbon atoms, and a saturated, partially saturated and/or unsaturated ring may be included. Examples of preferred heterocycloalkyl include 3- to 10-membered heterocycloalkyl, 3- to 8-membered heterpcycloalkyl, 3- to 6-membered heterocycloalkyl and the like. For example, "3- to 8-membered heterocycloalkyl" means 3- to 8-membered cycloalkyl containing at least one heteroatom selected from a nitrogen atom, an oxygen atom and a sulfur atom. Non-limiting examples of heterocycloalkyl includes aziridine, azetidine, pyrrolidine, piperidine, piperazine, morpholine, thiomorpholine, homopiperidine, tetrahydrofuran, tetrahydropyran, oxazolidinone, 2-azaspiro[4.4]nonane, 8-oxa-2-azaspiro[4.5]decane, hexahydropenta[c]pyrrole, 2-oxa-6-azaspiro[3.3]heptane, tetrahydro-2H-[1.4]dioxino[2,3-c]pyrrole etc.

"Aryl" means a monocyclic or bicyclic aromatic hydrocarbon group having six or more carbon atoms, in which one hydrogen atom on the aromatic ring is excluded, and it may be substituted with one or more substituent(s) included in the present invention, if necessary, at position(s) which can be substituted. Non-limiting examples of preferred aryl include $C_{6-10}$ aryl. Examples of aryl include phenyl, 1-naphthyl, 2-naphthyl, anthracenyl etc.

"Heteroaryl" means a monocyclic or bicyclic aromatic heterocyclo group containing at least one heteroatom selected from the group consisting of a nitrogen atom, an oxygen atom and a sulfur atom, and it may be substituted with one or more substituent(s) included in the present invention, if necessary, at position(s) which can be substituted. Examples of preferred heteroaryl include 3- to 10-membered heteroaryl, 3- to 6-membered heteroaryl, and 5- to 6-membered heteroaryl. For example, "5- to 6-membered heteroaryl" means 5- and 6-membered monocyclic heterocyclo group containing at least one heteroatom selected from a nitrogen atom, an oxygen atom and a sulfur atom. Non-limiting examples of heteroaryl include thiophen, furan, pyrrole, imidazole, pyrazole, thiazole, oxazole, isothiazole, isooxazole, pyridine, pyrimidine, pyrazine, pyridazine, triazine, indole, purin, quinoline, isoquinoline etc.

"Acyl" means carbonyl group [—C(=O)] connected to a hydrogen atom or above-defined alkyl, cycloalkyl, cycloheteroalkyl, aryl, or heteroaryl. Examples of preferred acyl include $C_{1-7}$ acyl, and $C_{1-4}$ acyl. For example, "$C_{1-4}$ acyl" means carbonyl group connected to an alkyl group having 1 to 3 carbon atom(s). Non-limiting examples of acyl include formyl, acetyl, propanoyl, butyryl, pivaloyl, cyclopentanecarbonyl, benzoyl etc.

"Acylamino" means an amino group connected to the acyl group defined above, and examples of preferred acylamino include $C_{1-7}$ acylamino, $C_{1-4}$ acylamino. For example, "$C_{1-4}$ acylamino" means an amino group connected to acyl having 1 to 4 carbon atom(s). Non-limiting examples of acylamino include acetylamino, propionylamino etc.

"Mono- or di-$C_{1-6}$ alkylamino" means an amino group in which one or two hydrogen atom(s) are replaced with $C_{1-6}$ alkyl defined above, and it may be substituted with the same or different alkyl groups when substituted with two alkyl groups. Non-limiting examples of mono- or di-$C_{1-6}$ alkylamino include methylamino, ethylamino, dimethylamino and diethylamino etc.

"Alkoxycarbonyl" means a carbonyl group to which the above-defined alkoxy is connected. Examples of preferred alkoxycarbonyl include $C_{1-6}$ alkoxycarbonyl, and $C_{1-4}$ alkoxycarbonyl. For example, "$C_{1-6}$ alkoxycarbonyl" means a carbonyl group to which an alkoxy group having 1- to 6-carbon atoms is connected. Non-limiting examples of alkoxycarbonyl include methoxycarbonyl, ethoxycarbonyl, propoxycarbonyl, butoxycarbonyl, tert-butoxycarbonyl, and hexyloxycarbonyl etc.

"Optionally substituted" means a case in which the position is not substituted (non-substituted) and a case in which it is substituted at a position which can be substituted. "Non-substituted" means all positions which can be substituted are hydrogen atoms. When substituted, it may be substituted with two or more substituent, if possible, and the substituents may be the same or different from each other. Examples of the substituent include a halogen atom, an alkyl group, an alkenyl group, a cycloalkyl group, a heterocyoalkyl group, a haloalkyl group, an alkoxy group, a haloalkoxy group, an amino group, a nitro group, a cyano group, a hydroxy group, a mono- or di-alkylamino group, a carbamoyl group, a carboxyl group, a morpholinyl group, a formyl group, an acetyl group, a mesyl group, a benzoyl group, an acylamino group, a benzyl group, an aryl group, a heteroaryl group etc.

"Pharmaceutically acceptable salt" means a salt formed by a compound of the formula (I) in the present invention and a pharmaceutically acceptable acid or base. When the compound of the formula (I) in the present invention has a basic functional group such as an amino group, it is possible to form a salt with a variety of acids. Examples of an acid-addition salt include a non-organic acid salt such as hydrochloride, hydrobromide, hydroiodide, sulfate, perchlorate and phosphate etc., an organic acid salt such as oxalate, malonate, maleate, fumarate, lactate, malate, citrate, tartrate, benzoate, trifluoroacetate, acetate, methanesulfonate, p-toluenesulfonate and trifluoromethanesulfonate, and an acidic amino acid salt such as glutamate, and aspartate.

When the compound of the formula (I) in the present invention has an acidic functional group, it is possible to form a salt with a variety of bases. Examples of a base-addition salt include an alkali metal salt such as a sodium salt and a potassium salt, an alkali earth metal salt such as a calcium salt, an organic amine salt such as a lower alkyl amine salt and a lower alcohol amine salt, a basic amino acid salt such as a lysine salt, an arginine salt and an ornithine salt, and an ammonium salt.

These salts can be prepared in a conventional manner such as recrystallization etc. after mixing the compound of the formula (I) in the present invention with an acid or base.

A compound of the present invention may be obtained as an inner salt, a hydrate and/or a solvate, and these inner salt, hydrate and solvate are also included in the present invention. Examples of the solvate include an ethanol solvate.

"Treatment" means healing and/or improvement of infection diseases caused by malaria *plasmodium* in mammals, especially human. For example, it is included (a) to prevent infection diseases caused by malaria *plasmodium*; (b) to inhibit propagation of infection disease caused by malaria *plasmodium*; and (c) to alleviate and/or reduce infection disease caused by malaria *plasmodium*.

"Patient" means human and animals such as a dog, a cat and a horse etc., and among them, human is preferable.

"Effective amount for treatment" means an amount for improvement, healing, prevention and/or reduction of a disease, a disorder and/or a side effect compared with an untreated patient, or an amount for retarding progression of a disease and/or a disorder. Said term also includes an effective amount for enhancing normal physiological functions. An effective amount of a compound of the formula (I) in the present invention may be administered as an unformulated bulk. Usually, a range from about 1 to about 1,000 mg/kg (body weight) of a compound of the formula (I) is effective, but the effective amount is not limited thereto.

Examples of the effective amount include an amount of the compound in the present invention alone, an amount of a combination of the compounds in the present invention and an amount of the compound of the present invention in a combination with other anti-malarial agent(s).

A preferred embodiment of the ring A is a 6-membered heteroaryl group having one or more nitrogen atom(s) optionally substituted with $R^1$, $R^2$ and $R^3$, and a more specific embodiment of the ring A is a heteroaryl group selected from the group consisting of

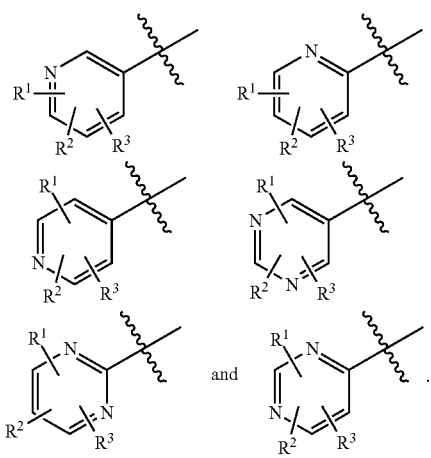

A preferred embodiment of Z is a group selected from the group consisting of an amino group, $C_{1-6}$ alkoxy group,

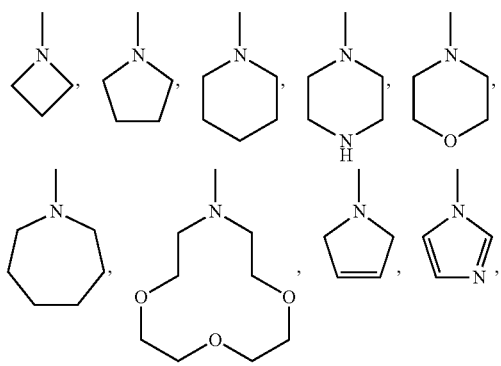

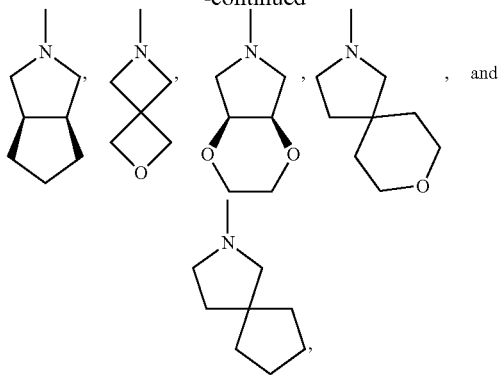

and each group may be substituted with one or more substituent(s), the same or different, selected from the group consisting of a halogen atom, a $C_{1-6}$ alkyl group, a $C_{1-6}$ haloalkyl group, a hydroxy group, a $C_{1-6}$ hydroxyalkyl group, a $C_{1-6}$ alkoxy group, an amino group, a mono- or di-$C_{1-6}$ alkylamino group, a carboxy group, a $C_{1-6}$ alkoxycarbonyl group, a 5- or 6-membered heterocycloalkyl group, a phenyl group, a benzyl group and a 5- or 6-membered heteroaryl group at a position which can be substituted.

A preferred embodiment of $R^1$ to $R^3$ is a hydrogen atom, a halogen atom, a hydroxy group, a nitro group, a $C_{1-6}$ alkyl group, a $C_{1-6}$ alkoxy group, a $C_{3-6}$ cycloalkyl group, a $C_{3-6}$ cycloalkyloxy group, a 3- to 6-membered heterocyclo-alkyloxy group, or a phenoxy group, wherein
the $C_{1-6}$ alkyl group, the $C_{1-6}$ alkoxy group, the $C_{3-6}$ cycloalkyl group, the $C_{3-6}$ cycloalkyloxy group, the 3- to 6-membered heterocycloalkyloxy group, and the phenoxy group may be independently substituted with one or more substituent(s), the same or different, selected from the group consisting of a halogen atom, a hydroxy group, an amino group, a mono- or di-$C_{1-6}$ alkylamino group, carboxy group, $C_{1-6}$ alkyl group, a $C_{2-6}$ alkenyl group, a $C_{1-6}$ alkoxy group and a phenyl group at a position which can be substituted.

A more preferred embodiment of $R^1$ to $R^3$ is a hydrogen atom, a fluorine atom, a chlorine atom, a hydroxy group, a nitro group, a methyl group, an ethyl group, an isopropyl group, a butyl group, an isobutyl group, a tert-butyl group, a neopentyl group, a fluoromethyl group, a trifluoromethyl group, a hydroxymethyl group, an ethoxymethyl group, a propoxymethyl group, a 2-(pyrrolidin-1-yl)ethyl group, a methoxy group, an ethoxy group, a propoxy group, an isopropoxy group, a butoxy group, an isobutoxy group, a neopentyloxy group, a difluoromethoxy group, a trifluoroethoxy group, a 2-(dimethylamino)ethoxy group, an allyloxy group, a 2-methoxyethoxy group, a 2-(tert-butoxy) ethoxy group, a 2-morpholinoethoxy group, a 2-hydroxyethoxy group, a benzyloxy group, a cyclopropyl group, a cyclobutoxy group, a cyclohexyloxy group, a (1-methylpiperidin-4-yl)oxy group, a (tetrahydro-2H-pyran-4-yl)oxy group or a phenoxy group.

A compound of the formula (I) or an intermediate of the present invention can be separated and purified with a method known to a skilled person in the art. For example, an extraction, a distribution, a re-precipitation, a column chromatography such as a silica gel column chromatography, an ion-exchange column chromatography or a preparative liquid chromatography and a recrystallization etc. are exemplified.

A compound of the formula (I) of the present invention may have one or more asymmetric carbon(s), or include geometric isomerism or axial chirality, and several kinds of optical isomers or stereoisomers may be provided. These optical isomers or stereoisomers, a mixture thereof and a racemate are included in the compound of the formula (I) of the present invention.

A compound of the formula (I) of the present invention may have an isomer depending on a structure of its substituent, for example. The present invention include every possible isomer (a geometric isomer, an optical isomer and a tautomer etc.), and not only an isolated isomer, but a mixture of isomers are included therein, though only one chemical structure of the single isomer is described in this specification.

Further a deuterated compound of the formula (I) in the present invention in which one or more $^1$H are replaced with $^2$H(D) is also include therein.

A compound of the formula (I) or its pharmaceutical salt of the present invention may have crystalline polymorph, which is also included in the present invention.

A compound of the present invention or pharmaceutically acceptable salt thereof can be prepared, for example, according to methods described below. When a group defined in the formula may be changed under the described conditions or is improper for the chemical reaction, the desired product may be easily obtained by using a means which is common in an organic synthesis such as a protection and a deprotection of a functional group [T. W. Greene, Protective Groups in Organic Synthesis 3rd Edition, John Wiley & Sons, Inc., 1999]. Also it is possible to change an order of processes introducing a substituent etc., if necessary.

Meanings of abbreviations and symbols used in the following description are as follows.

THF: Tetrahydrofuran
NMP: N-methyl pyrrolidone
2-PrOH: 2-propanol
DIEA: N,N-diisopropyl ethylamine
DMSO: Dimethyl sulfoxide
DMF: Dimethylformamide
TEA: Triethylamine
MeOH: Methanol
EtOH: Ethanol
CHCl$_3$: Chloroform
CDCl$_3$: Heavy chloroform
DCM: Dichloromethane
RuPhos: 2-Dicyclohexylphosphino-2',6'-diisopropoxybiphenyl
BrettPhos: 2-(Dicyclohexylphosphino)-3,6-dimethoxy-2',4',6'-triisopropyl-1,1'-biphenyl
Xantphos: 4,5-Bis(diphenyl phosphino)-9,9-dimethyl xanthene
Pd(dba)$_2$: Bis(dibenzylideneacetone)palladium(0)

[Method for Preparing a Compound of the Formula (I) in the Present Invention]

A compound of the formula (I) of the present invention can be prepared according to scheme 1, for example:

scheme 1 wherein the ring A, R$^1$, R$^2$, R$^3$ and Z are the same as described before.

The compound (I) can be prepared by reacting a chloro compound (II) with imidazo[1,2-a]pyrdine-7-amine under the condition of a cross-coupling reaction such as Buchwald/Hartwig type reaction. Specifically, the reaction is carried out by using a palladium catalyst such as Pd(dba)$_2$, a base such as sodium tert-butoxide, potassium carbonate, and cesium carbonate and a ligand such as RuPhos, BrettPhos, Xantphos in an inert solvent such as toluene, THF or dioxane. It is preferable to use equivalent or excess amount of imidazo[1,2-a]pyrdine-7-amine compared with the chloro compound (II), and 1 to 10 equivalent is more preferrable. The product is synthesized by the reaction for a few minutes to a few days at 0° C. to 200° C., preferably for 1 hour to 36 hours at 20° C. to 150° C. It is also possible to synthesize the product by reacting under the temperature condition of from 60° C. to 150° C. for several minutes to several hours, using a microwave synthesis equipment.

The chloro compound (II) which is used in scheme 1 as a starting material can be prepared according to scheme 2, for example:

scheme 2 wherein the ring A, R$^1$, R$^2$, R$^3$ and Z are the same as described before.

The chloro compound (II) can be prepared by heating and reacting 0.8 to 5 mole equivalent, preferably 0.8 to 1 mole equivalent of the compound (IV) with the dichloro compound (III) in a solvent. If necessary, an acid catalyst such as hydrochloric acid, or a base may be added to the reaction, and any solvent may be used if the reaction is not disturbed, but a polar solvent such as DMF or THF is preferable. When the compound (IV) is a liquid and the reacting point is an alcoholic hydroxy group, the compound (IV) itself may be used as a solvent. The reaction can be carried out by stirring the reaction mixture for 3 to 24 hours at room temperature to a refluxing condition of the solvent.

The compound (IV) which is one of starting materials in scheme 2 can be obtained as a commercially available product, or can be obtained by a well-known procedure or the procedure according to it.

The dichloro compound (III) can be prepared according to scheme 3, for example;

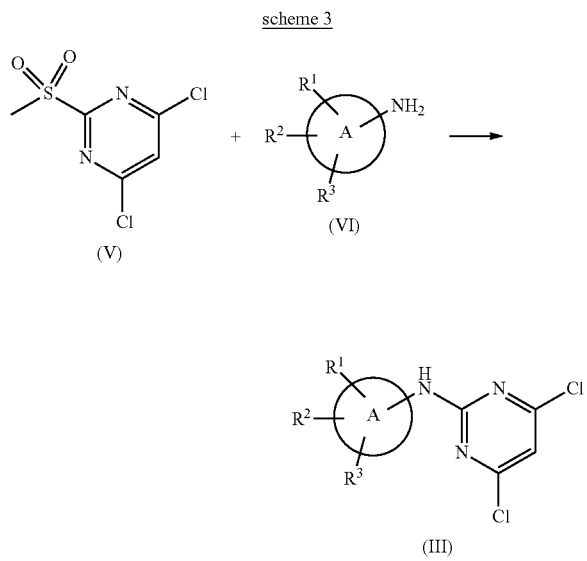

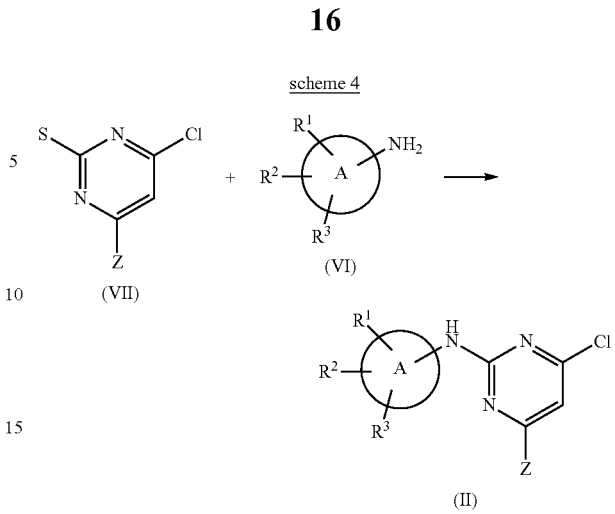

wherein the ring A, $R^1$, $R^2$ and $R^3$ are the same as described before.

The dichloro compound (III) can be prepared by reacting 4,6-dichloro-2-(methylsulfonyl)pyrimidine (V) with the amine (VI). Specifically, The dichloro compound (III) can be obtained by reacting 0.5 to 5 mole equivalent, preferably 1.2 to 2.0 mole equivalent of the amine (VI) with 4,6-dichloro-2-(methylsulfonyl)pyrimidine (V) in a solvent. If necessary, an acid catalyst such as hydrochloric acid, or a base may be added to the reaction, and any solvent may be used if the reaction is not disturbed, but a polar solvent such as THF or dioxane is preferable. The reaction can be carried out by reacting for 1 to 24 hours at −78° C. to a refluxing condition of the solvent, preferably reacting for 0.5 to 2 hours at −78° C. to −70° C.

The amine (VI) which is one of starting materials in scheme 3 can be obtained as a commercially available product, or can be obtained by a well-known procedure or the procedure according to it.

The dichloro compound (III) can be also prepared by replacing 4,6-dichloro-2-(methylsulfonyl)pyrimidine (V) with 2,4,6-trichloropyrimidine in scheme 3 and reacting it in the same manner.

The chloro compound (II) which is used in scheme 1 as a starting material can be also prepared according to scheme 4, for example;

wherein the ring A, $R^1$, $R^2$, $R^3$ and Z are the same as described before.

The chloro compound (II) can be prepared by reacting the compound (VII) with the amine (VI). Specifically, the chloro compound (II) can be obtained by reacting 0.5 to 2 mole equivalent, preferably 0.8 to 1.5 mole equivalent of the amine (VI) with the compound (VII) in a solvent. If necessary, an acid catalyst such as hydrochloric acid, or a base may be added to the reaction, and any solvent may be used if the reaction is not disturbed, but a polar solvent, preferably an alcoholic solvent such as EtOH or 2-PrOH, or dioxane or THF may be used. The reaction can be carried out by reacting for 1 to 24 hours at −40° C. to a refluxing condition of the solvent, preferably reacting for 1 to 16 hours at room temperature to a refluxing condition of the solvent.

The compound (VII) which is used in scheme 4 as a starting material can be obtained as a commercially available product, or can be obtained by a well-known procedure or the procedure according to it.

In addition, a compound of the present invention having a desired functional group at a desired position can be prepared by a suitable combination of the methods above, or a procedure usually carried out in an organic synthesis (for example, alkylation reaction of an amino group, oxidation reaction of an alkylthio group into a sulfoxide group or a sulfone group, converting reaction of an alkoxy group into a hydroxy group, or opposite converting reaction thereof).

[Use of a Compounds of the Present Invention]

A compound (I) or a pharmaceutically acceptable salt thereof of the present invention can be prepared into a form of a conventional pharmaceutical formulation (pharmaceutical composition), which is suited for oral administration, parenteral administration, or local administration.

Formulations for oral administration include solid formulations such as tablets, granules, powders, and capsules; and liquid formulations such as syrups. These formulations can be prepared by a conventional method. The solid formulations can be prepared by using conventional pharmaceutical carriers, for example, lactose; starches such as corn starch; crystalline celluloses such as microcrystalline cellulose; and hydroxypropyl cellulose, calcium carboxymethyl cellulose; talc, and magnesium stearate. Capsules can be prepared by encasing thus prepared granules or powders in capsules. Syrups can be prepared by dissolving or suspending the compound (I) or a pharmaceutically acceptable salt thereof of the present invention in an aqueous solution containing sucrose and carboxymethyl cellulose etc.

Formulations for parenteral administration include injections such as instillation. Injection formulations can also be prepared by a conventional method, and can be appropriately incorporated into isotonic agents (for example, mannitol, sodium chloride, glucose, sorbitol, glycerol, xylitol, fructose, maltose, mannose), stabilizers (for example, sodium sulfite, albumin), and antiseptics (for example, benzyl alcohol, methyl p-oxybenzoate).

The dosage of the compound (I) or a pharmaceutically acceptable salt thereof of the present invention can vary depending on severity of disease, age and body weight of the patient, and dosage form, and is usually within a range from 1 mg to 1,000 mg per day for adults. The compound or a pharmaceutically acceptable salt thereof can be administered once, or dividedly administered twice or three times according to an oral or parenteral route.

A compound (I) of the present invention is useful for treating, preventing and/or inhibiting propagation of infection disease caused by malaria *plasmodium*, which is tolerant to known anti-malaria agents such as chloroquine and sulfadoxine/pyrimethamine (fansidar). Moreover, it is useful as a reagent of experimental or laboratory use for inhibiting proliferation of malaria *plasmodium*.

EXAMPLES

The present invention will be more specifically described below by way of Examples and Test Examples, but the present invention is not limited to these Examples.

Identification of the compound was carried out by hydrogen nuclear magnetic resonance spectrum ($^1$H-NMR) and mass spectrum (MS). $^1$H-NMR is measured at 400 MHz, unless otherwise specified, and exchangeable hydrogen cannot be sometimes clearly observed depending on the compound and measurement conditions. Abbreviation of "br." means a broad signal (broad).

HPLC preparative chromatography was carried out by a commercially available ODS column in a gradient mode using water/methanol (containing formic acid) as eluents, unless otherwise specified.

Reference Example 1

Preparation of 4-Chloro-N-(6-ethoxypyridin-3-yl)-6-morpholinopyrimidin-2-amine

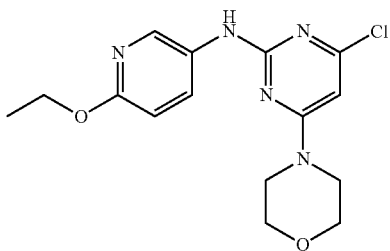 [SMILES: CCOc1ccc(Nc2nc(Cl)cc(N3CCOCC3)n2)cn1]

(Process 1)

A THF solution (5 ml) of 5-amino-2-ethoxypyridine (0.5 g, 3.6 mmol) was cooled to −78° C., a THF solution of sodium bis(trimethylsilyl)amide (2M, 3 ml, 6.0 mmol) was added thereto and the mixture was stirred for 10 minutes. A THF solution (5 ml) of 4,6-dichloro-2-(methylsulfonyl)pyrimidine (0.548 g, 2.4 mmol) was added to the reaction mixture, and the whole mixture was stirred for an hour. After confirming disappearance of the starting material, acetic acid and water were added, and extracted with 50% ethyl acetate/hexane. The obtained organic layer was dried over anhydrous sodium sulfate. The solvent was evaporated and the residue was purified with a column chromatography (silica gel, ethyl acetate/hexane) to give 4,6-dichloro-N-(6-ethoxypyridin-3-yl)pyrimidin-2-amine (0.325 g).

$^1$H-NMR (CDCl$_3$) δ(ppm): 8.25 (d, J=2.5 Hz, 1H), 7.84 (dd, J=2.9, 8.8 Hz, 1H), 7.00 (br. s, 1H), 6.77-6.74 (m, 2H), 4.35 (q, J=7.3 Hz, 2H), 1.40 (t, J=7.1 Hz, 3H); LCMS (m/z) 285.1[M+H]$^+$.

(Process 2)

A DMF solution (5 ml) of 4,6-dichloro-N-(6-ethoxypyridin-3-yl)pyrimidin-2-amine (0.325 g, 1.14 mmol) was cooled to 0° C., sodium hydrogen carbonate (0.191 g, 2.28 mmol) and morpholine (0.092 g, 105 mmol) were added thereto and the mixture was stirred at room temperature for 16 hours. After confirming disappearance of the starting material, water was added, and extracted with ethyl acetate. The obtained organic layer was dried over anhydrous sodium sulfate. The solvent was evaporated and the residue was purified with a column chromatography (silica gel, ethyl acetate/hexane) to give the titled compound (0.28 g).

$^1$H-NMR (DMSO-d$_6$) δ(ppm): 9.36 (br. s, 1H), 8.36 (d, J=2.5 Hz, 1H), 7.87 (dd, J=2.7, 9.1 Hz, 1H), 6.74 (d, J=8.8 Hz, 1H), 6.32 (s, 1H), 4.24 (q, J=6.9 Hz, 2H), 3.65-3.56 (m, 8H), 1.29 (t, J=6.9 Hz, 3H); LCMS (m/z) 336.2[M+H]$^+$.

Reference Example 2

Preparation of 4-chloro-6-morpholino-N-(pyridin-4-yl)pyrimidin-2-amine

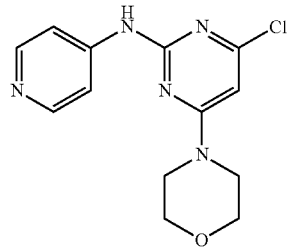 [SMILES: Clc1cc(N2CCOCC2)nc(Nc2ccncc2)n1]

A catalytic amount of conc. hydrochloric acid was added to an isopropanol solution (10 ml) of 4-(2,6-dichloro-4-pyrimidinyl)morpholine (1.0 g, 4.27 mmol) and 4-aminopyridine (0.321 g, 3.41 mmol), and stirred at 90° C. for 16 hours. The precipitated solid was collected by filtration, washed with isopropanol, methanol and ethyl acetate successively, and a white crude product was obtained. The solid was dissolved in 10% MeOH/DCM, and washed with water. The obtained aqueous layer was condensed under reduced pressure, and the obtained solid was purified with a column chromatography (silica gel, TEA/MeOH/DCM) to give the titled compound (0.8 g).

$^1$H-NMR (CD$_3$OD) δ(ppm): 9.22-9.18 (m, 2H), 7.20-6.88 (m, 4H), 3.75-3.65 (m, 8H); LCMS (m/z) 292.4[M+H]$^+$.

Example 7

Preparation of N2-(6-Ethoxypyridin-3-yl)-N4-(imidazo[1,2-a]pyridin-7-yl)-6-morpholinopyrimidine-2,4-diamine

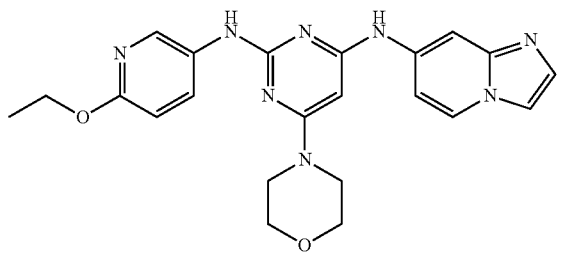 [SMILES: CCOc1ccc(Nc2nc(Nc3ccn4ccnc4c3)cc(N3CCOCC3)n2)cn1]

A dioxane solution (7 ml) of the compound of Reference Example 1 (0.2 g. 0.598 mmol), imidazo[1,2-a]pyridin-7-amine (0.119 g, 0.898 mmol) and sodium tert-butoxide (0.115 g, 1.19 mmol) was degassed, and Brettphos palladacycle G1 (0.048 g, 0.05 mmol) and Ruphos (0.028 g, 0.05 mmol) were added. The reaction mixture was further degassed by blowing nitrogen gas into it and the reaction was continued in a microwave reaction equipment at 110° C. for 30 minute. After confirming disappearance of the starting material, the reaction mixture was filtered with celite, and washed with 10% MeOH/DCM. The filtrate was condensed under reduced pressure, and the obtained solid was purified with a column chromatography (silica gel, MeOH/DCM) to give the titled compound (0.05 g).

$^1$H-NMR (DMSO-$d_6$) δ(ppm): 9.16 (s, 1H), 8.90 (br. s, 1H), 8.38-8.33 (m, 2H), 8.10-8.05 (m, 1H), 8.01 (dd, J=2.7, 9.1 Hz, 1H), 7.72 (s, 1H), 7.40 (s, 1H), 7.05-7.00 (m, 1H), 6.78-6.70 (m, 1H), 5.56 (s, 1H), 4.25 (q, J=7.2 Hz, 2H), 3.70-3.67 (m, 4H), 3.45-3.43 (m, 4H), 1.29 (t, J=6.9 Hz, 3H); LCMS (m/z) 433.3[M+H]$^+$.

Examples 1-6 and 8-222

Each of the Example compounds shown in the following [Table 1-1] to [Table 1-40] were prepared according to the procedure described in Example 7 above or said procedure combined with a common method well known in the art of organic chemistry, if needed, using appropriate starting materials (those materials are obtained from commercial sources, or are prepared by literature procedures or modifications of literature procedures known to persons skilled in the art).

The physicochemical data of each compound were shown in the following [Table 2-1] to [Table 2-41].

TABLE 1-1

| Ex. | Structure | Name |
|---|---|---|
| 1 | 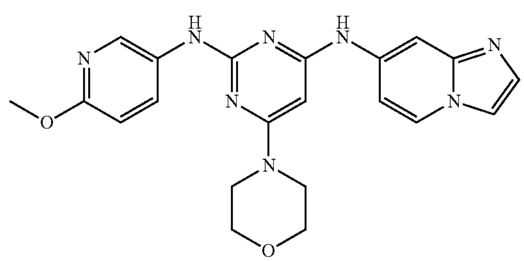 [SMILES: COc1ccc(Nc2nc(Nc3ccn4ccnc4c3)cc(N3CCOCC3)n2)cn1] | N4-(Imidazo[1,2-a]pyridin-7-yl)-N2-(6-methoxypyridin-3-yl)-6-morpholinopyrimidine-2,4-diamine |
| 2 | 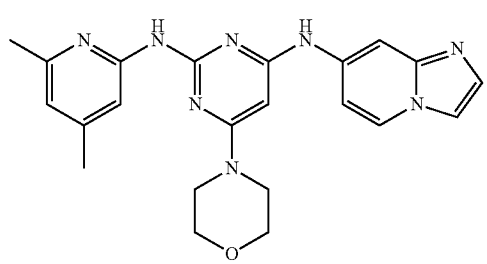 [SMILES: Cc1cc(C)nc(Nc2nc(Nc3ccn4ccnc4c3)cc(N3CCOCC3)n2)c1] | N2-(4,6-dimethylpyridin-2-yl)-N4-(imidazo[1,2-a]pyridin-7-yl)-6-morpholinopyrimidine-2,4-diamine |
| 3 | 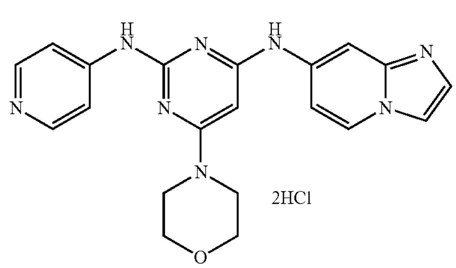 [SMILES: c1cc(Nc2nc(Nc3ccn4ccnc4c3)cc(N3CCOCC3)n2)ccn1] | N4-(imidazo[1,2-a]pyridin-7-yl)-6-morpholino-N2-(pyridin-4-yl)pyrimidine-2,4-diamine dihydrochloride |

TABLE 1-1-continued

| Ex. | Structure | Name |
|---|---|---|
| 4 | 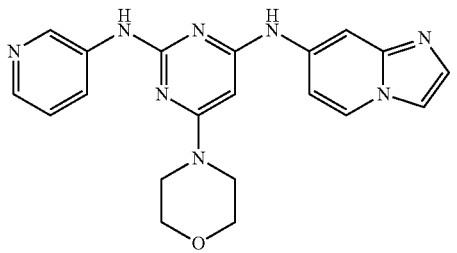 [SMILES: c1cncc(Nc2nc(Nc3ccn4ccnc4c3)cc(N3CCOCC3)n2)c1] | N4-(Imidazo[1,2-a]pyridin-7-yl)-6-morpholino-N2-(pyridin-3-yl)pyrimidine-2,4-diamine |
| 5 | 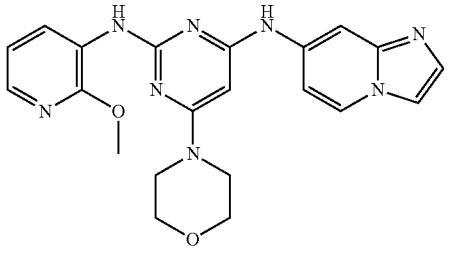 [SMILES: COc1ncccc1Nc1nc(Nc2ccn3ccnc3c2)cc(N2CCOCC2)n1] | N4-(Imidazo[1,2-a]pyridin-7-yl)-N2-(2-methoxypyridin-3-yl)-6-morpholinopyrimidine-2,4-diamine |
| 6 | 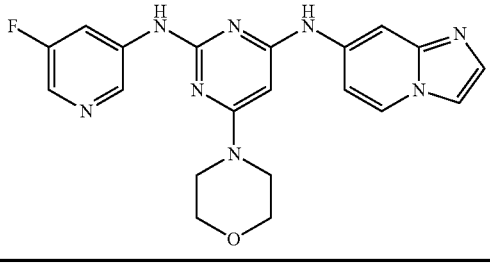 | N2-(5-Fluoropyridin-3-yl)-N4-(imidazo[1,2-a]pyridin-7-yl)-6-morpholinopyrimidine-2,4-diamine |

TABLE 1-2

| 8 | 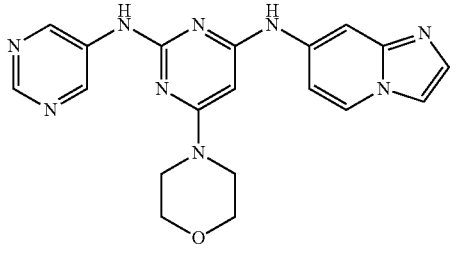 [SMILES: c1ncc(Nc2nc(Nc3ccn4ccnc4c3)cc(N3CCOCC3)n2)cn1] | N4-(Imidazo[1,2-a]pyridin-7-yl)-6-morpholino-N2-(pyrimidin-5-yl)pyrimidine-2,4-diamine |
| 9 | 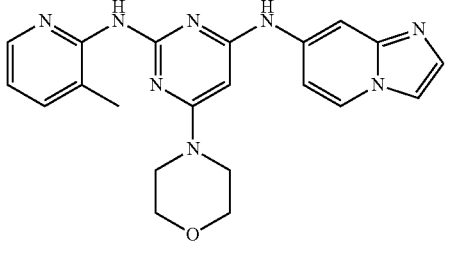 [SMILES: Cc1cccnc1Nc1nc(Nc2ccn3ccnc3c2)cc(N2CCOCC2)n1] | N4-(Imidazo[1,2-a]pyridin-7-yl)-N2-(3-methylpyridin-2-yl)-6-morpholinopyrimidine-2,4-diamine |

TABLE 1-2-continued

| 10 | 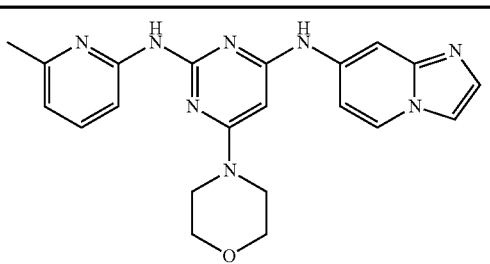 | N4-(Imidazo[1,2-a]pyridin-7-yl)-N2-(6-methylpyridin-2-yl)-6-morpholinopyrimidine-2,4-diamine |
| 11 | 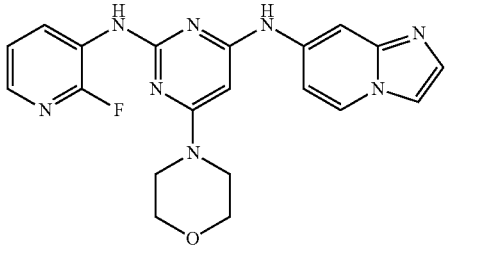 [SMILES: Fc1ncccc1Nc1nc(Nc2ccn3ccnc3c2)cc(N2CCOCC2)n1] | N2-(2-Fluoropyridin-3-yl)-N4-(imidazo[1,2-a]pyridin-7-yl)-6-morpholinopyrimidine-2,4-diamine |
| 12 | 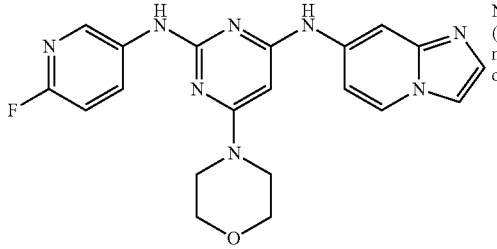 | N2-(6-Fluoropyridin-3-yl)-N4-(imidazo[1,2-a]pyridin-7-yl)-6-morpholinopyrimidine-2,4-diamine |
| 13 | 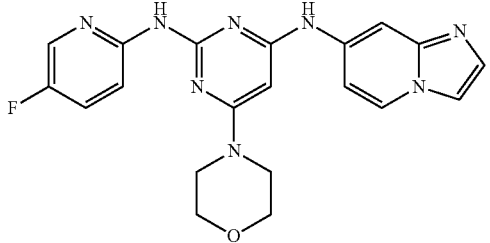 [SMILES: Fc1ccc(Nc2nc(Nc3ccn4ccnc4c3)cc(N3CCOCC3)n2)nc1] | N2-(5-Fluoropyridin-2-yl)-N4-(imidazo[1,2-a]pyridin-7-yl)-6-morpholinopyrimidine-2,4-diamine |
| 14 | 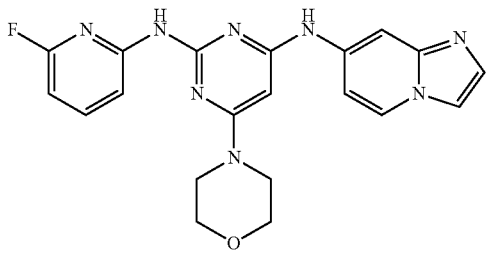 [SMILES: Fc1cccc(Nc2nc(Nc3ccn4ccnc4c3)cc(N3CCOCC3)n2)n1] | N2-(6-Fluoropyridin-2-yl)-N4-(imidazo[1,2-a]pyridin-7-yl)-6-morpholinopyrimidine-2,4-diamine |

TABLE 1-3

| 15 | 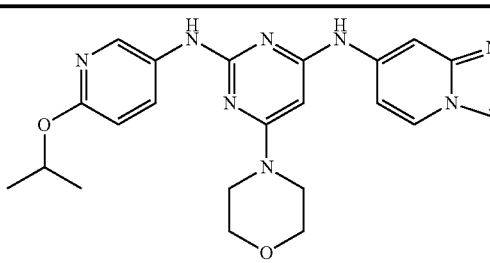 | N4-(Imidazo[1,2-a]pyridin-7-yl)-N2-(6-isopropoxypyridin-3-yl)-6-morpholinopyrimidine-2,4-diamine |

TABLE 1-3-continued

| | Structure | Name |
|---|---|---|
| 16 | 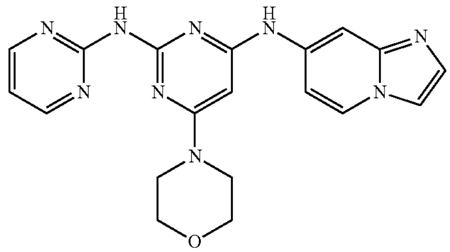 [SMILES: c1cnc(Nc2nc(Nc3ccn4ccnc4c3)cc(N3CCOCC3)n2)nc1] | N4-(Imidazo[1,2-a]pyridin-7-yl)-6-morpholino-N2-(pyrimidin-2-yl)pyrimidine-2,4-diamine |
| 17 | 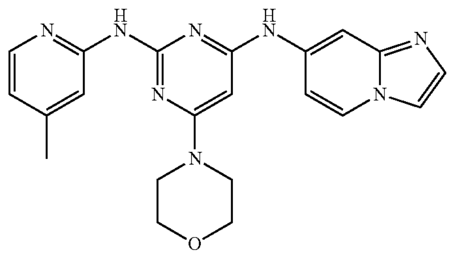 [SMILES: Cc1ccnc(Nc2nc(Nc3ccn4ccnc4c3)cc(N3CCOCC3)n2)c1] | N4-(Imidazo[1,2-a]pyridin-7-yl)-N2-(4-methylpyridin-2-yl)-6-morpholinopyrimidine-2,4-diamine |
| 18 | 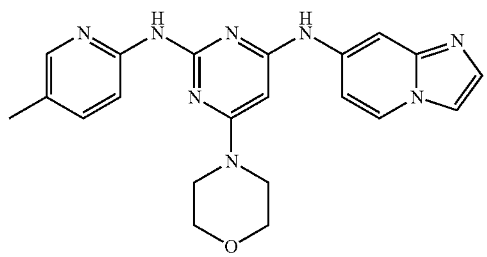 | N4-(Imidazo[1,2-a]pyridin-7-yl)-N2-(5-methylpyridin-2-yl)-6-morpholinopyrimidine-2,4-diamine |
| 19 | 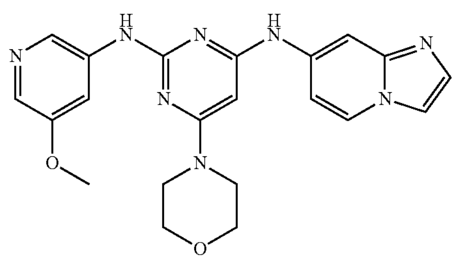 [SMILES: COc1cncc(Nc2nc(Nc3ccn4ccnc4c3)cc(N3CCOCC3)n2)c1] | N4-(Imidazo[1,2-a]pyridin-7-yl)-N2-(5-methoxypyridin-3-yl)-6-morpholinopyrimidine-2,4-diamine |
| 20 | 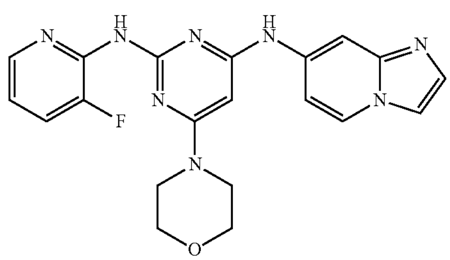 | N2-(3-Fluoropyridin-2-yl)-N4-(imidazo[1,2-a]pyridin-7-yl)-6-morpholinopyrimidine-2,4-diamine |
| 21 | 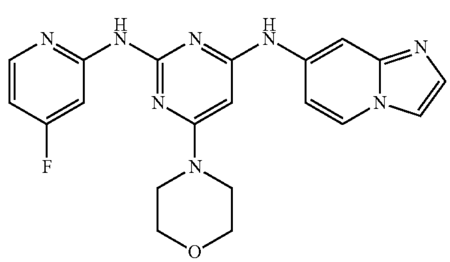 | N2-(4-Fluoropyridin-2-yl)-N4-(imidazo[1,2-a]pyridin-7-yl)-6-morpholinopyrimidine-2,4-diamine |

TABLE 1-4

| 22 | | N4-(Imidazo[1,2-a]pyridin-7-yl)-6-morpholino-N2-(pyrimidin-4-yl)pyrimidine-2,4-diamine |
| --- | --- | --- |
| 23 | | N4-(Imidazo[1,2-a]pyridin-7-yl)-N2-(4-methoxypyridin-3-yl)-6-morpholinopyrimidine-2,4-diamine |
| 24 | | 5-(4-(Imidazo[1,2-a]pyridin-7-ylamino)-6-morpholinopyrimidin-2-ylamino)pyridin-2-ol |
| 25 | | N4-(imidazo[1,2-a]pyridin-7-yl)-6-(4-methylpiperazin-1-yl)-N2-(4-methylpyridin-2-yl)pyrimidine-2,4-diamine |
| 26 | | N4-(imidazo[1,2-a]pyridin-7-yl)-N2-(5-methylpyridin-2-yl)-6-(piperidin-1-yl)pyrimidine-2,4-diamine |
| 27 | | N4-(imidazo[1,2-a]pyridin-7-yl)-6-(4-methylpiperazin-1-yl)-N2-(5-methylpyridin-2-yl)pyrimidine-2,4-diamine |

TABLE 1-4-continued

| | | |
|---|---|---|
| 28 | 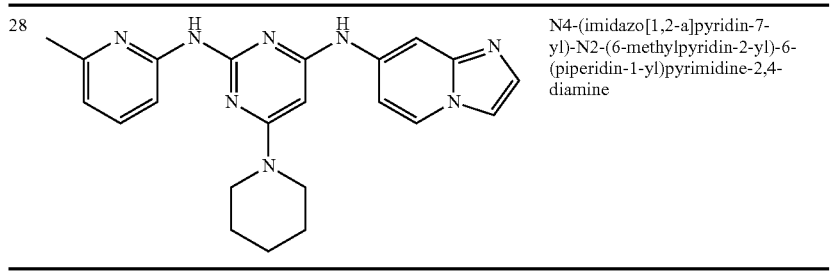 | N4-(imidazo[1,2-a]pyridin-7-yl)-N2-(6-methylpyridin-2-yl)-6-(piperidin-1-yl)pyrimidine-2,4-diamine |

TABLE 1-5

| | | |
|---|---|---|
| 29 | 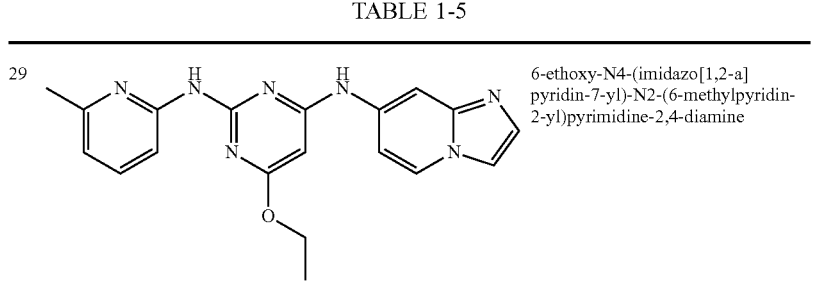 | 6-ethoxy-N4-(imidazo[1,2-a]pyridin-7-yl)-N2-(6-methylpyridin-2-yl)pyrimidine-2,4-diamine |
| 30 | 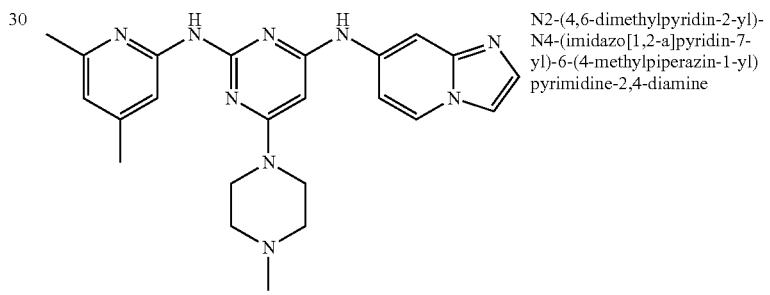 | N2-(4,6-dimethylpyridin-2-yl)-N4-(imidazo[1,2-a]pyridin-7-yl)-6-(4-methylpiperazin-1-yl)pyrimidine-2,4-diamine |
| 31 | 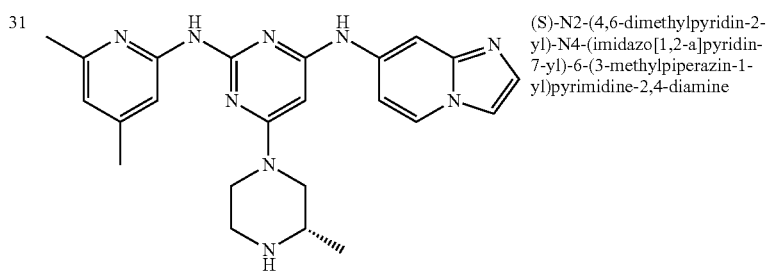 | (S)-N2-(4,6-dimethylpyridin-2-yl)-N4-(imidazo[1,2-a]pyridin-7-yl)-6-(3-methylpiperazin-1-yl)pyrimidine-2,4-diamine |
| 32 | 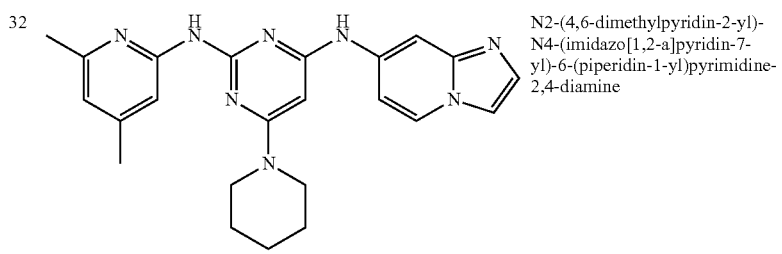 | N2-(4,6-dimethylpyridin-2-yl)-N4-(imidazo[1,2-a]pyridin-7-yl)-6-(piperidin-1-yl)pyrimidine-2,4-diamine |

TABLE 1-5-continued

| # | Structure | Name |
|---|---|---|
| 33 | 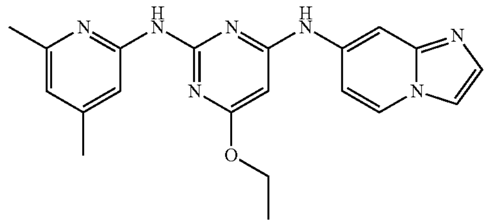 [SMILES: CCOc1cc(Nc2ccn3ccnc3c2)nc(Nc2cc(C)cc(C)n2)n1] | N2-(4,6-dimethylpyridin-2-yl)-6-ethoxy-N4-(imidazo[1,2-a]pyridin-7-yl)pyrimidine-2,4-diamine |
| 34 | 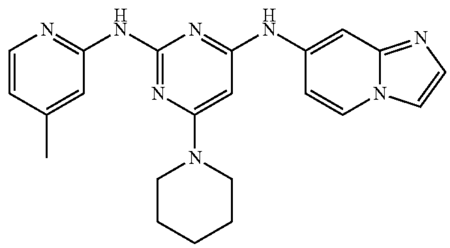 [SMILES: Cc1ccnc(Nc2nc(Nc3ccn4ccnc4c3)cc(N3CCCCC3)n2)c1] | N4-(imidazo[1,2-a]pyridin-7-yl)-N2-(4-methylpyridin-2-yl)-6-(piperidin-1-yl)pyrimidine-2,4-diamine |
| 35 | 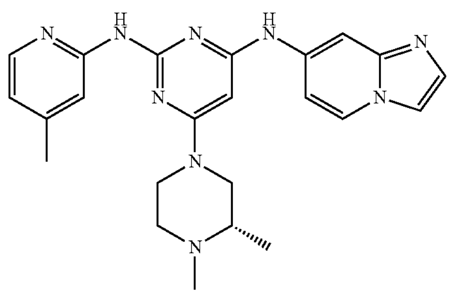 [SMILES: Cc1ccnc(Nc2nc(Nc3ccn4ccnc4c3)cc(N3CCN(C)[C@@H](C)C3)n2)c1] | (S)-6-(3,4-dimethylpiperazin-1-yl)-N4-(imidazo[1,2-a]pyridin-7-yl)-N2-(4-methylpyridin-2-yl)pyrimidine-2,4-diamine |

TABLE 1-6

| # | Structure | Name |
|---|---|---|
| 36 | 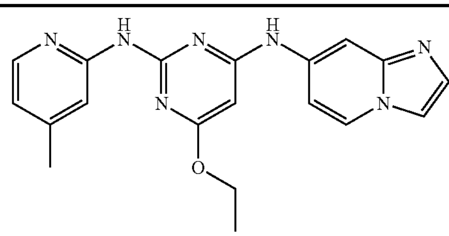 | 6-ethoxy-N4-(imidazo[1,2-a]pyridin-7-yl)-N2-(4-methylpyridin-2-yl)pyrimidine-2,4-diamine |
| 37 | 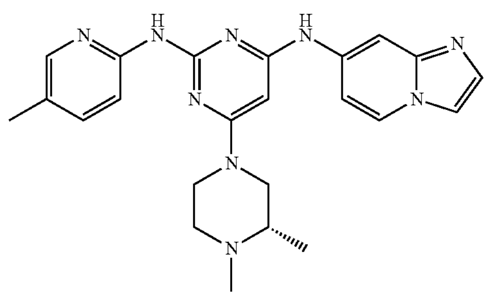 [SMILES: Cc1ccc(Nc2nc(Nc3ccn4ccnc4c3)cc(N3CCN(C)[C@@H](C)C3)n2)nc1] | (S)-6-(3,4-dimethylpiperazin-1-yl)-N4-(imidazo[1,2-a]pyridin-7-yl)-N2-(5-methylpyridin-2-yl)pyrimidine-2,4-diamine |
| 38 | 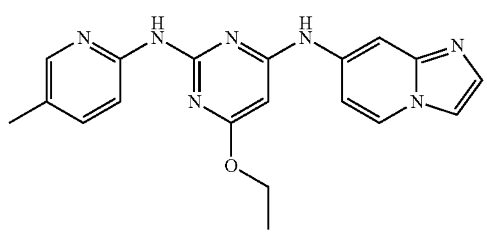 [SMILES: CCOc1cc(Nc2ccn3ccnc3c2)nc(Nc2ccc(C)cn2)n1] | 6-ethoxy-N4-(imidazo[1,2-a]pyridin-7-yl)-N2-(5-methylpyridin-2-yl)pyrimidine-2,4-diamine |

TABLE 1-6-continued

| # | Structure | Name |
|---|---|---|
| 39 | 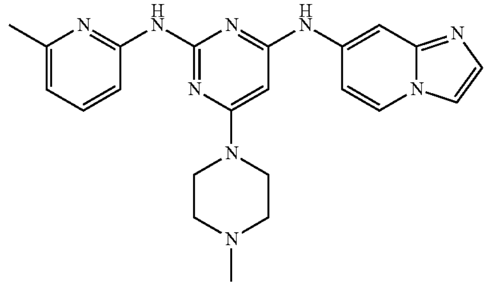 | N4-(imidazo[1,2-a]pyridin-7-yl)-6-(4-methylpiperazin-1-yl)-N2-(6-methylpyridin-2-yl)pyrimidine-2,4-diamine |
| 40 | 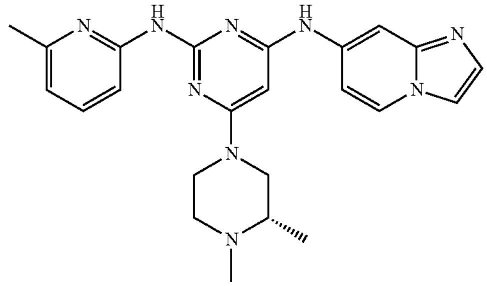 [SMILES: Cc1cccc(Nc2nc(Nc3ccn4ccnc4c3)cc(N3CCN(C)[C@@H](C)C3)n2)n1] | (S)-6-(3,4-dimethylpiperazin-1-yl)-N4-(imidazo[1,2-a]pyridin-7-yl)-N2-(6-methylpyridin-2-yl)pyrimidine-2,4-diamine |
| 41 | 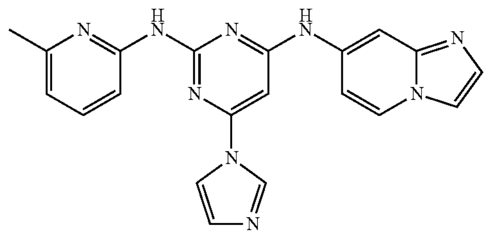 [SMILES: Cc1cccc(Nc2nc(Nc3ccn4ccnc4c3)cc(-n3ccnc3)n2)n1] | N4-(imidazo[1,2-a]pyridin-7-yl)-6-(1H-imidazol-1-yl)-N2-(6-methylpyridin-2-yl)pyrimidine-2,4-diamine |
| 42 | 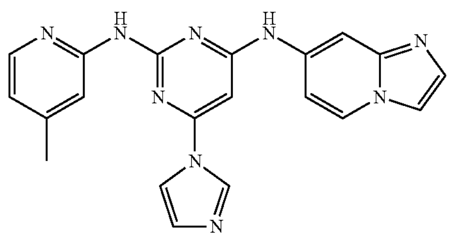 [SMILES: Cc1ccnc(Nc2nc(Nc3ccn4ccnc4c3)cc(-n3ccnc3)n2)c1] | N4-(imidazo[1,2-a]pyridin-7-yl)-6-(1H-imidazol-1-yl)-N2-(4-methylpyridin-2-yl)pyrimidine-2,4-diamine |

TABLE 1-7

| # | Structure | Name |
|---|---|---|
| 43 | 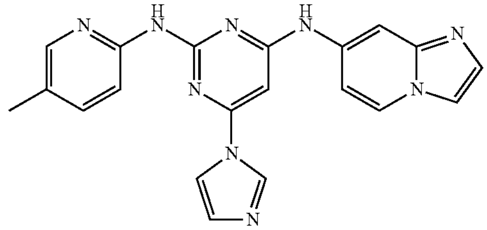 [SMILES: Cc1ccc(Nc2nc(Nc3ccn4ccnc4c3)cc(-n3ccnc3)n2)nc1] | N4-(imidazo[1,2-a]pyridin-7-yl)-6-(1H-imidazol-1-yl)-N2-(5-methylpyridin-2-yl)pyrimidine-2,4-diamine |
| 44 | 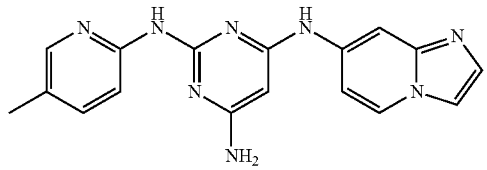 [SMILES: Cc1ccc(Nc2nc(N)cc(Nc3ccn4ccnc4c3)n2)nc1] | N4-amidazo[1,2-a]pyridin-7-yl)-N2-(5-methylpyridin-2-yl)pyrimidine-2,4,6-triamine |

TABLE 1-7-continued

| | | |
|---|---|---|
| 45 | | (S)-6-(3,4-dimethylpiperazin-1-yl)-N2-(4,6-dimethylpyridin-2-yl)-N4-(imidazo[1,2-a]pyridin-7-yl)pyrimidine-2,4-diamine |
| 46 | | N2-(4,6-dimethylpyridin-2-yl)-N4-(imidazo[1,2-a[pyridin-7-yl)-6-(1H-imidazol-1-yl)pyrimidine-2,4-diamine |
| 47 | | N4-(imidazo[1,2-a]pyridin-7-yl)-6-morpholino-N2-(4-(trifluoromethyl)pyridin-2-yl)pyrimidine-2,4-diamine |
| 48 | | N4-(imidazo[1,2-a]pyridin-7-yl)-N2-(4-methoxypyridin-2-yl)-6-morpholinopyrimidine-2,4-diamine |

TABLE 1-8

| | | |
|---|---|---|
| 49 | | N4-(imidazo[1,2-a]pyridin-7-yl)-6-morpholino-N2-(4-nitropyridin-2-yl)pyrimidine-2,4-diamine |
| 50 | | N4-(imidazo[1,2-a]pyridin-7-yl)-N2-(4-methylpyridin-2-yl)pyrimidine-2,4,6-triamine |

TABLE 1-8-continued

| | | |
|---|---|---|
| 51 | 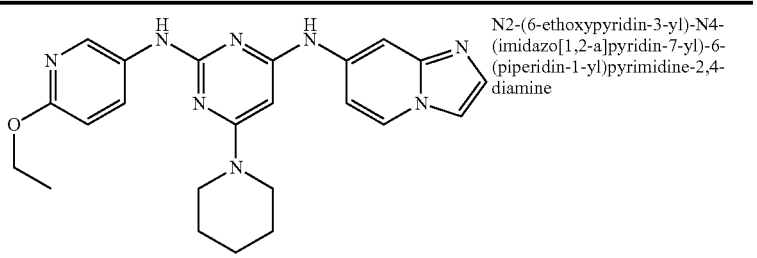 | N2-(6-ethoxypyridin-3-yl)-N4-(imidazo[1,2-a]pyridin-7-yl)-6-(piperidin-1-yl)pyrimidine-2,4-diamine |
| 52 | 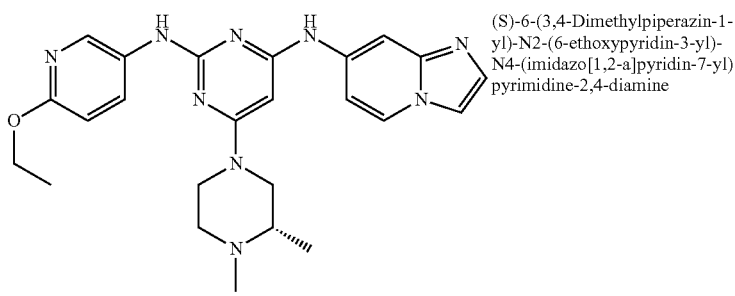 | (S)-6-(3,4-Dimethylpiperazin-1-yl)-N2-(6-ethoxypyridin-3-yl)-N4-(imidazo[1,2-a]pyridin-7-yl)pyrimidine-2,4-diamine |
| 53 | 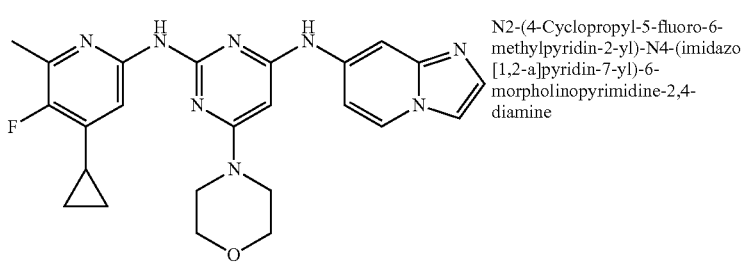 | N2-(4-Cyclopropyl-5-fluoro-6-methylpyridin-2-yl)-N4-(imidazo[1,2-a]pyridin-7-yl)-6-morpholinopyrimidine-2,4-diamine |
| 54 | 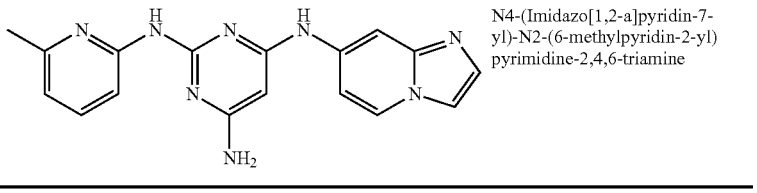 | N4-(Imidazo[1,2-a]pyridin-7-yl)-N2-(6-methylpyridin-2-yl)pyrimidine-2,4,6-triamine |

TABLE 1-9

| | | |
|---|---|---|
| 55 | 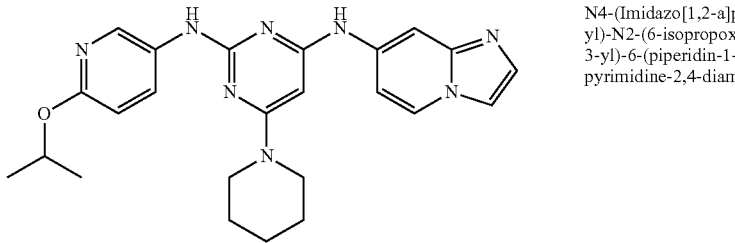 | N4-(Imidazo[1,2-a]pyridin-7-yl)-N2-(6-isopropoxypyridin-3-yl)-6-(piperidin-1-yl)pyrimidine-2,4-diamine |
| 56 | 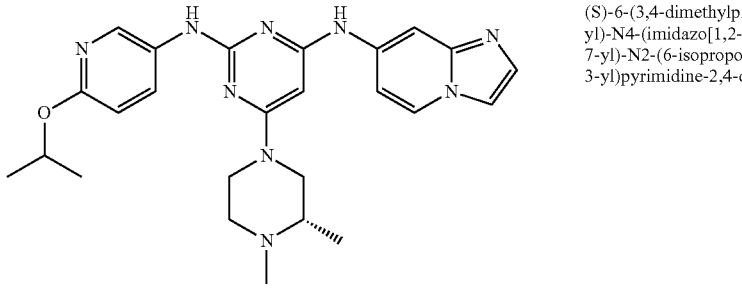 | (S)-6-(3,4-dimethylpiperazin-1-yl)-N4-(imidazo[1,2-a]pyridin-7-yl)-N2-(6-isopropoxypyridin-3-yl)pyrimidine-2,4-diamine |

TABLE 1-9-continued

| | | |
|---|---|---|
| 57 | | 6-Ethoxy-N4-(Imidazo[1,2-a]pyridin-7-yl)-N2-(6-isopropoxypyridin-3-yl)pyrimidine-2,4-diamine |
| 58 | | N2-(4,6-dimethylpyridin-2-yl)-N4-(imidazo[1,2-a]pyridin-7-yl)pyrimidine-2,4,6-triamine |
| 59 | | N4-(imidazo[1,2-a]pyridin-7-yl)-N2-(6-isopropoxypyridin-3-yl)-6-(4-methylpiperazin-1-yl)pyrimidine-2,4-diamine |
| 60 | | N4-(imidazo[1,2-a]pyridin-7-yl)-N2-(6-methylpyridin-3-yl)-6-morpholinopyrimidine-2,4-diamine |

TABLE 1-10

| | | |
|---|---|---|
| 61 | | N2-(6-(2-(dimethylamino)ethoxy)pyridin-3-yl)-N4-(imidazo[1,2-a]pyridin-7-yl)-6-morpholino-pyrimidine-2,4-diamine |
| 62 | | N2-(6-butoxypyridin-3-yl)-N4-(imidazo[1,2-a]pyridin-7-yl)-6-morpholinopyrimidine-2,4-diamine |

TABLE 1-10-continued

| | | |
|---|---|---|
| 63 | 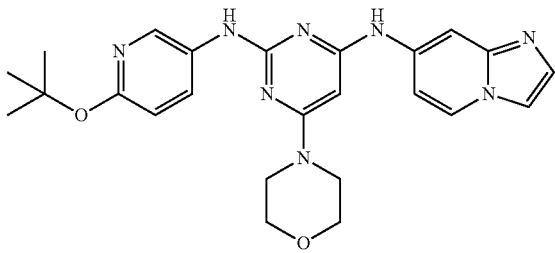 [SMILES: CC(C)(C)Oc1ccc(Nc2nc(Nc3ccn4ccnc4c3)cc(N3CCOCC3)n2)cn1] | N2-(6-(tert-butoxy)pyridin-3-yl)-N4-(imidazo[1,2-a]pyridin-7-yl)-6-morpholinopyrimidine-2,4-diamine |
| 64 | 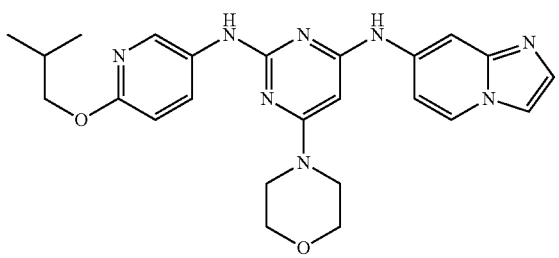 [SMILES: CC(C)(C)COc1ccc(Nc2nc(Nc3ccn4ccnc4c3)cc(N3CCOCC3)n2)cn1] | N4-(imidazo[1,2-a]pyridin-7-yl)-N2-(6-isobutoxypyridin-3-yl)-6-morpholinopyrimidine-2,4-diamine |
| 65 | 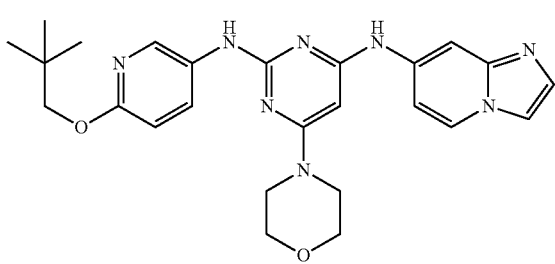 | N4-(imidazo[1,2-a]pyridin-7-yl)-6-morpholino-N2-(6-(neopentyloxy)pyridin-3-yl)pyrimidine-2,4-diamine |
| 66 | 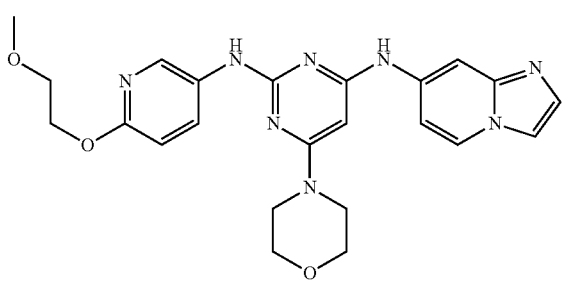 [SMILES: COCCOc1ccc(Nc2nc(Nc3ccn4ccnc4c3)cc(N3CCOCC3)n2)cn1] | N4-(imidazo[1,2-a]pyridin-7-yl)-N2-(6-(2-methoxyethoxy)-pyridin-3-yl)-6-morpholino-pyrimidine-2,4-diamine |

TABLE 1-11

| | | |
|---|---|---|
| 67 | 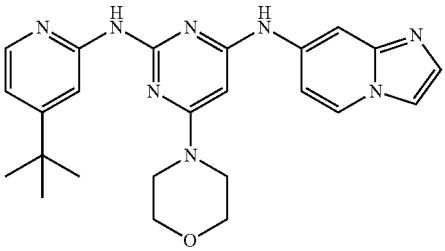 [SMILES: CC(C)(C)c1ccnc(Nc2nc(Nc3ccn4ccnc4c3)cc(N3CCOCC3)n2)c1] | N2-(4-(tert-butyl)pyridin-2-yl)-N4-(imidazo[1,2-a]pyridin-7-yl)-6-morpholinopyrimidine-2,4-diamine |
| 68 | 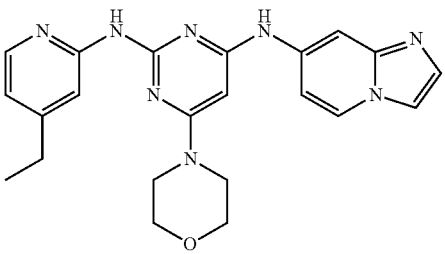 [SMILES: CCc1ccnc(Nc2nc(Nc3ccn4ccnc4c3)cc(N3CCOCC3)n2)c1] | N2-(4-ethylpyridin-2-yl)-N4-(imidazo[1,2-a]pyridin-7-yl)-6-morpholinopyrimidine-2,4-diamine |

TABLE 1-11-continued

| | | |
|---|---|---|
| 69 | 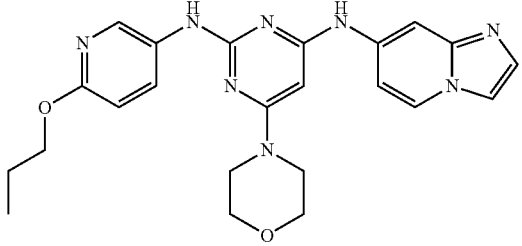 [SMILES: CCCOc1ccc(Nc2nc(Nc3ccn4ccnc4c3)cc(N3CCOCC3)n2)cn1] | N4-(imidazo[1,2-a]pyridin-7-yl)-6-morpholino-N2-(6-propoxy-pyridin-3-yl)pyrimidine-2,4-diamine |
| 70 | 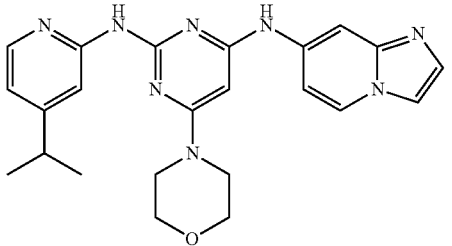 | N4-(imidazo[1,2-a]pyridin-7-yl)-N2-(4-isopropylpyridin-2-yl)-6-morpholinopyrimidine-2,4-diamine |
| 71 | 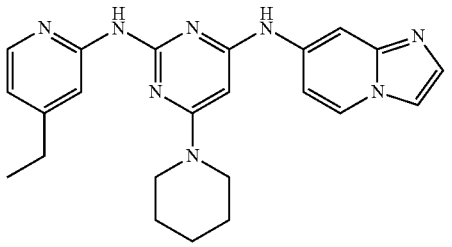 [SMILES: CCc1ccnc(Nc2nc(Nc3ccn4ccnc4c3)cc(N3CCCCC3)n2)c1] | N2-(4-ethylpyridin-2-yl)-N4-(imidazo[1,2-a]pyridin-7-yl)-6-(piperidin-1-yl)pyrimidine-2,4-diamine |
| 72 | 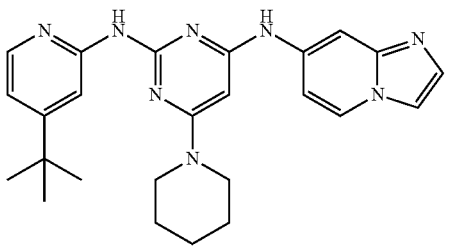 [SMILES: CC(C)(C)c1ccnc(Nc2nc(Nc3ccn4ccnc4c3)cc(N3CCCCC3)n2)c1] | N2-(4-(tert-butyl)pyridin-2-yl)-N4-(imidazo[1,2-a]pyridin-7-yl)-6-(piperidin-1-yl)pyrimidine-2,4-diamine |

TABLE 1-12

| | | |
|---|---|---|
| 73 | 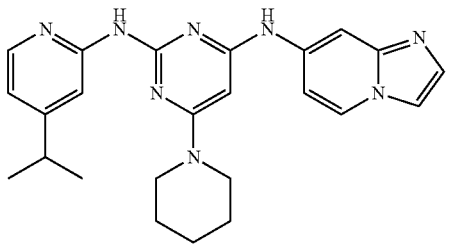 [SMILES: CC(C)c1ccnc(Nc2nc(Nc3ccn4ccnc4c3)cc(N3CCCCC3)n2)c1] | N4-(imidazo[1,2-a]pyridin-7-yl)-N2-(4-isopropylpyridin-2-yl)-6-(piperidin-1-yl)pyrimidine-2,4-diamine |
| 74 | 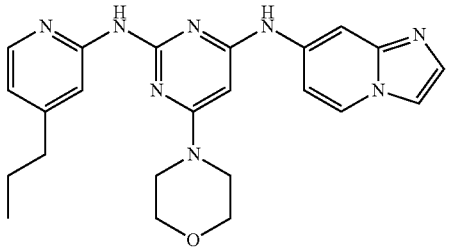 | N4-(imidazo[1,2-a]pyridin-7-yl)-6-morpholino-N2-(4-propylpyridin-2-yl)pyrimidine-2,4-diamine |

TABLE 1-12-continued

| | | |
|---|---|---|
| 75 | | N4-(imidazo[1,2-a]pyridin-7-yl)-6-(piperidin-1-yl)-N2-(4-propylpyridin-2-yl)pyrimidine-2,4-diamine |
| 76 | | N2-(6-(allyloxy)pyridin-3-yl)-N4-(imidazo[1,2-a]pyridin-7-yl)-6-morpholinopyrimidine-2,4-diamine |
| 77 | | N4-(imidazo[1,2-a]pyridin-7-yl)-6-morpholino-N2-(6-(2,2,2-trifluoroethoxy)pyridin-3-yl)pyrimidine-2,4-diamine |
| 78 | | N2-(6-(difluoromethoxy)pyridin-3-yl)-N4-(imidazo[1,2-a]pyridin-7-yl)-6-morpholinopyrimidine-2,4-diamine |

TABLE 1-13

| | | |
|---|---|---|
| 79 | | N4-(imidazo[1,2-a]pyridin-7-yl)-N2-(6-methylpyridin-3-yl)-6-(piperidin-1-yl)pyrimidine-2,4-diamine |
| 80 | | N2-(6-cyclobutoxypyridin-3-yl)-N4-(imidazo[1,2-a]pyridin-7-yl)-6-morpholinopyrimidine-2,4-diamine |

TABLE 1-13-continued

| | Structure | Name |
|---|---|---|
| 81 | 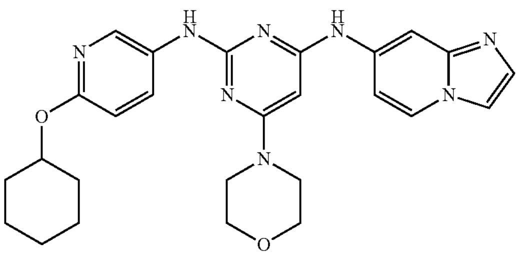 [SMILES: c1cn2ccc(Nc3cc(N4CCOCC4)nc(Nc4ccc(OC5CCCCC5)nc4)n3)cc2n1] | N2-(6-(cyclohexyloxy)pyridin-3-yl)-N4-(imidazo[1,2-a]pyridin-7-yl)-6-morpholinopyrimidine-2,4-diamine |
| 82 | 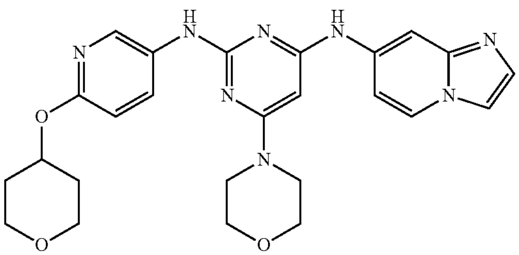 [SMILES: c1cn2ccc(Nc3cc(N4CCOCC4)nc(Nc4ccc(OC5CCOCC5)nc4)n3)cc2n1] | N4-(imidazo[1,2-a]pyridin-7-yl)-6-morpholino-N2-(6-((tetrahydro-2H-pyran-4-yl)oxy)pyridin-3-yl)pyrimidine-2,4-diamine |
| 83 | 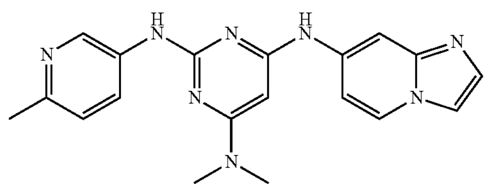 [SMILES: Cc1ccc(Nc2nc(Nc3ccn4ccnc4c3)cc(N(C)C)n2)cn1] | N4-(imidazo[1,2-a]pyridin-7-yl)-N6,N6-dimethyl-N2-(6-methylpyridin-3-yl)pyrimidine-2,4,6-triamine |
| 84 | 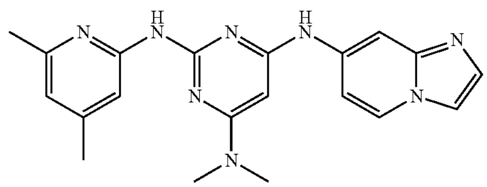 [SMILES: Cc1cc(C)nc(Nc2nc(Nc3ccn4ccnc4c3)cc(N(C)C)n2)c1] | N2-(4,6-dimethylpyridin-2-yl)-N4-(imidazo[1,2-a]pyridin-7-yl)-N6,N6-dimethylpyrimidine-2,4,6-triamine |

TABLE 1-14

| | Structure | Name |
|---|---|---|
| 85 | 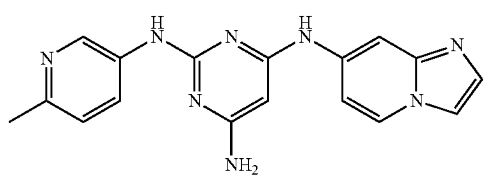 [SMILES: Cc1ccc(Nc2nc(N)cc(Nc3ccn4ccnc4c3)n2)cn1] | N4-(imidazo[1,2-a]pyridin-7-yl)-N2-(6-methylpyridin-3-yl)pyrimidine-2,4,6-triamine |
| 86 | 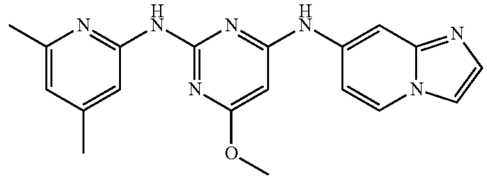 [SMILES: COc1cc(Nc2ccn3ccnc3c2)nc(Nc2cc(C)cc(C)n2)n1] | N2-(4,6-dimethylpyridin-2-yl)-N4-(imidazo[1,2-a]pyridin-7-yl)-6-methoxypyrimidine-2,4-diamine |

TABLE 1-14-continued

| | Structure | Name |
|---|---|---|
| 87 | 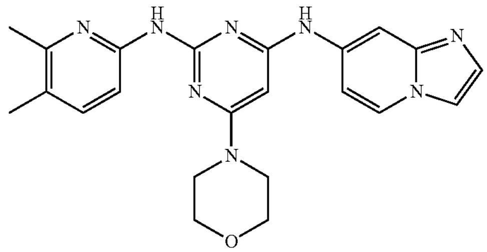 [SMILES: Cc1ccc(Nc2nc(Nc3ccn4ccnc4c3)cc(N3CCOCC3)n2)nc1C] | N2-(5,6-dimethylpyridin-2-yl)-N4-(imidazo[1,2-a]pyridin-7-yl)-6-morpholinopyrimidine-2,4-diamine |
| 88 | 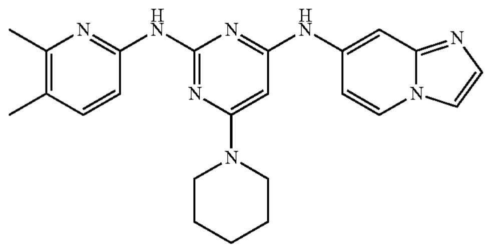 [SMILES: Cc1ccc(Nc2nc(Nc3ccn4ccnc4c3)cc(N3CCCCC3)n2)nc1C] | N2-(5,6-dimethylpyridin-2-yl)-N4-(imidazo[1,2-a]pyridin-7-yl)-6-(piperidin-1-yl)pyrimidine-2,4-diamine |
| 89 | 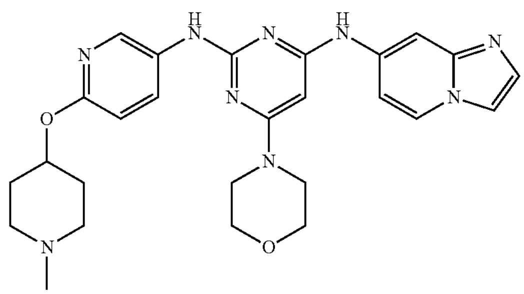 [SMILES: CN1CCC(Oc2ccc(Nc3nc(Nc4ccn5ccnc5c4)cc(N4CCOCC4)n3)cn2)CC1] | N4-(imidazo[1,2-a]pyridin-7-yl)-N2-(6-((1-methylpiperidin-4-yl)oxy)pyridin-3-yl)-6-morpholinopyrimidine-2,4-diamine |
| 90 | 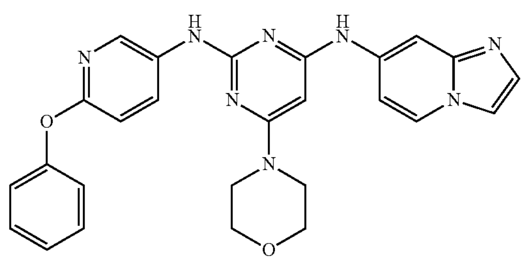 [SMILES: c1ccc(Oc2ccc(Nc3nc(Nc4ccn5ccnc5c4)cc(N4CCOCC4)n3)cn2)cc1] | N4-(imidazo[1,2-a]pyridin-7-yl)-6-morpholino-N2-(6-phenoxypyridin-3-yl)pyrimidine-2,4-diamine |

TABLE 1-15

| | Structure | Name |
|---|---|---|
| 91 | 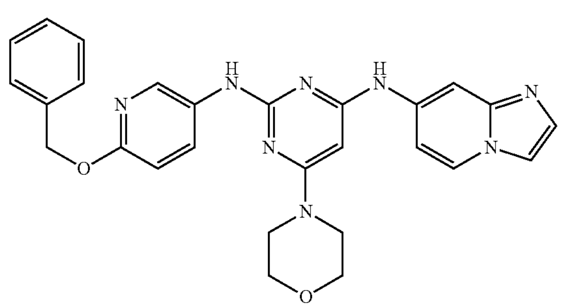 [SMILES: c1ccc(COc2ccc(Nc3nc(Nc4ccn5ccnc5c4)cc(N4CCOCC4)n3)cn2)cc1] | N2-(6-(benzyloxy)pyridin-3-yl)-N4-(imidazo[1,2-a]pyridin-7-yl)-6-morpholinopyrimidine-2,4-diamine |

TABLE 1-15-continued

| # | Structure | Name |
|---|---|---|
| 92 | 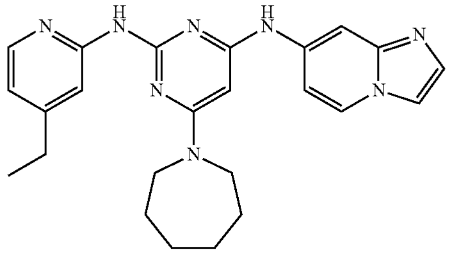 [SMILES: CCc1ccnc(Nc2nc(Nc3ccn4ccnc4c3)cc(N3CCCCCC3)n2)c1] | 6-(azepan-1-yl)-N2-(4-ethylpyridin-2-yl)-N4-(imidazo[1,2-a]pyridin-7-yl)pyrimidine-2,4-diamine |
| 93 | 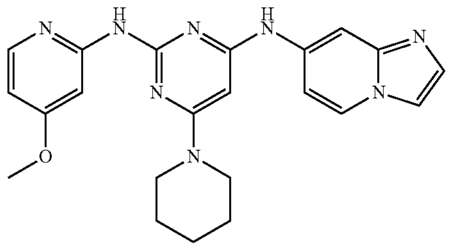 [SMILES: COc1ccnc(Nc2nc(Nc3ccn4ccnc4c3)cc(N3CCCCC3)n2)c1] | N4-(imidazo[1,2-a]pyridin-7-yl)-N2-(4-methoxypyridin-2-yl)-6-(piperidin-1-yl)pyrimidine-2,4-diamine |
| 94 | 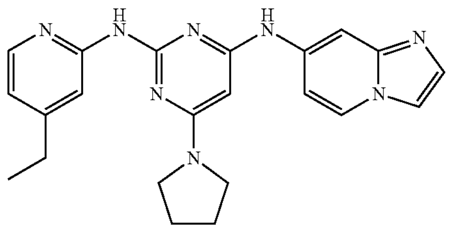 | N2-(4-ethylpyridin-2-yl)-N4-(imidazo[1,2-a]pyridin-7-yl)-6-(pyrrolidin-1-yl)pyrimidine-2,4-diamine |
| 95 | 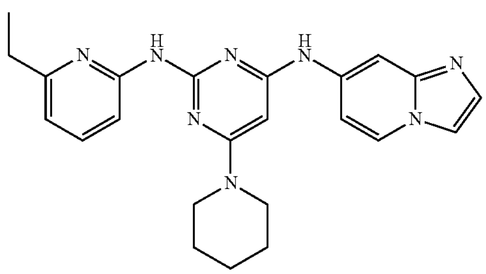 [SMILES: CCc1cccc(Nc2nc(Nc3ccn4ccnc4c3)cc(N3CCCCC3)n2)n1] | N2-(6-ethylpyridin-2-yl)-N4-(imidazo[1,2-a]pyridin-7-yl)-6-(piperidin-1-yl)pyrimidine-2,4-diamine |
| 96 | 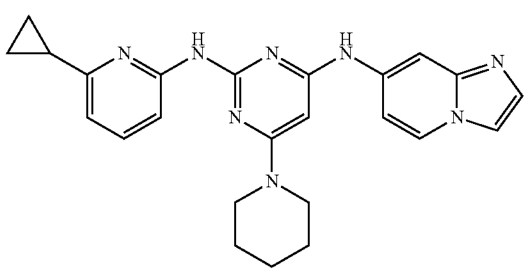 [SMILES: c1cc(Nc2nc(Nc3ccn4ccnc4c3)cc(N3CCCCC3)n2)nc(C2CC2)c1] | N2-(6-cyclopropylpyridin-2-yl)-N4-(imidazo[1,2-a]pyridin-7-yl)-6-(piperidin-1-yl)pyrimidine-2,4-diamine |

TABLE 1-16

| # | Structure | Name |
|---|---|---|
| 97 | 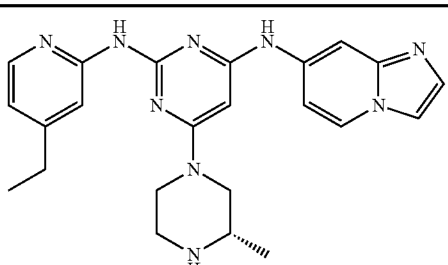 | (S)-N2-(4-ethylpyridin-2-yl)-N4-(imidazo[1,2-a]pyridin-7-yl)-6-(3-methylpiperazin-1-yl)pyrimidine-2,4-diamine |

TABLE 1-16-continued

| # | Structure | Name |
|---|---|---|
| 98 | 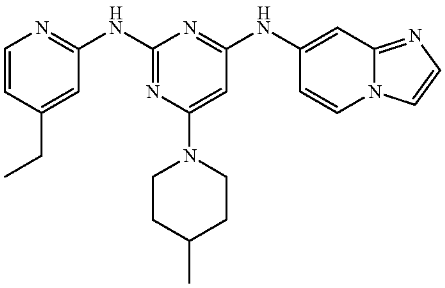 | N2-(4-ethylpyridin-2-yl)-N4-(imidazo[1,2-a]pyridin-7-yl)-6-(4-methylpiperidin-1-yl)pyrimidine-2,4-diamine |
| 99 | 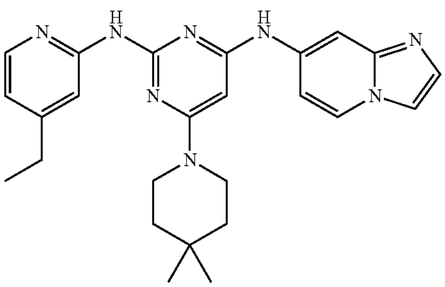 [SMILES: CCc1ccnc(Nc2nc(Nc3ccn4ccnc4c3)cc(N3CCC(C)(C)CC3)n2)c1] | 6-(4,4-dimethylpiperidin-1-yl)-N2-(4-ethylpyridin-2-yl)-N4-(imidazo[1,2-a]pyridin-7-yl)pyrimidine-2,4-diamine |
| 100 | 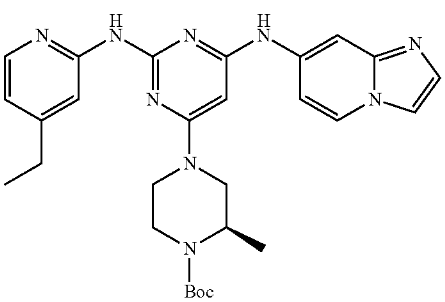 [SMILES: CCc1ccnc(Nc2nc(Nc3ccn4ccnc4c3)cc(N3CCN(C(=O)OC(C)(C)C)[C@H](C)C3)n2)c1] | (R)-tert-butyl 4-(2-((4-ethylpyridin-2-yl)amino)-6-(imidazo[1,2-a]pyridin-7-ylamino)pyrimidin-4-yl)-2-methylpiperazine-1-carboxylate |
| 101 | 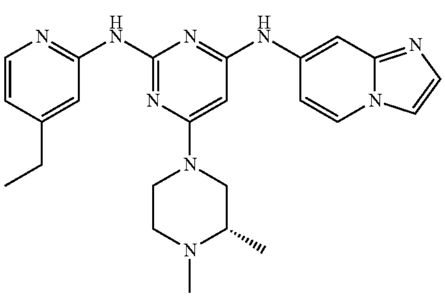 [SMILES: CCc1ccnc(Nc2nc(Nc3ccn4ccnc4c3)cc(N3CCN(C)[C@@H](C)C3)n2)c1] | (S)-6-(3,4-dimethylpiperazin-1-yl)-N2-(4-ethylpyridin-2-yl)-N4-(imidazo[1,2-a]pyridin-7-yl)pyrimidine-2,4-diamine |

TABLE 1-17

| # | Structure | Name |
|---|---|---|
| 102 | 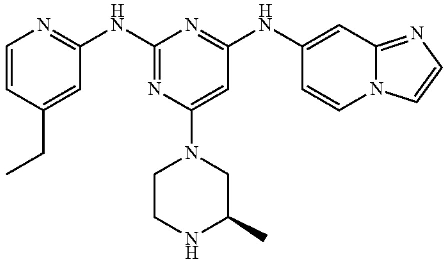 [SMILES: CCc1ccnc(Nc2nc(Nc3ccn4ccnc4c3)cc(N3CCN[C@H](C)C3)n2)c1] | (R)-N2-(4-ethylpyridin-2-yl)-N4-(imidazo[1,2-a]pyridin-7-yl)-6-(3-methylpiperazin-1-yl)pyrimidine-2,4-diamine |

TABLE 1-17-continued

| | | |
|---|---|---|
| 103 | 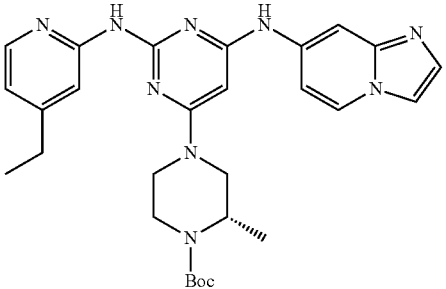 [SMILES: CCc1ccnc(Nc2nc(Nc3ccn4ccnc4c3)cc(N3CCN(C(=O)OC(C)(C)C)[C@@H](C)C3)n2)c1] | (S)-tert-butyl 4-(2-((4-ethylpyridin-2-yl)amino)-6-(imidazo[1,2-a]pyridin-7-ylamino)pyrimidin-4-yl)-2-methylpiperazine-1-carboxylate |
| 104 | 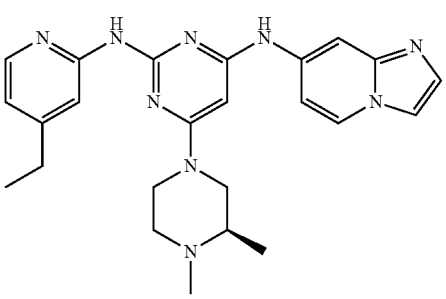 [SMILES: CCc1ccnc(Nc2nc(Nc3ccn4ccnc4c3)cc(N3CCN(C)[C@H](C)C3)n2)c1] | (R)-6-(3,4-dimethylpiperazin-1-yl)-N2-(4-ethylpyridin-2yl)-N4-(imidazo[1,2-a]pyridin-7-yl)pyrimidine-2,4-diamine |
| 105 | 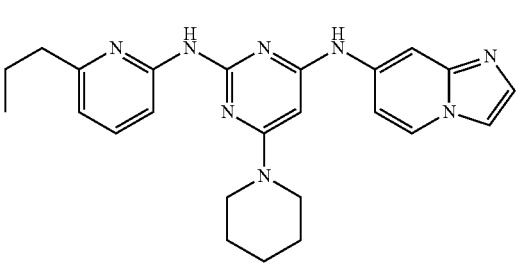 [SMILES: CCCc1cccc(Nc2nc(Nc3ccn4ccnc4c3)cc(N3CCCCC3)n2)n1] | N4-(imidazo[1,2-a]pyridin-7-yl)-6-(piperidin-1-yl)-N2-(6-propylpyridin-2-yl)pyrimidine-2,4-diamine |
| 106 | 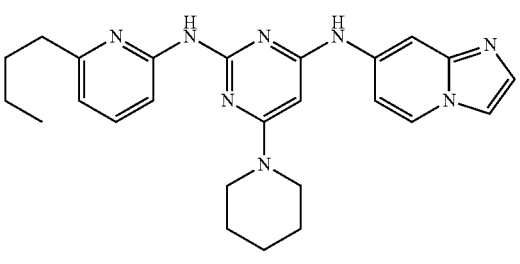 [SMILES: CCCCc1cccc(Nc2nc(Nc3ccn4ccnc4c3)cc(N3CCCCC3)n2)n1] | N2-(6-butylpyridin-2-yl)-N4-(imidazo[1,2-a]pyridin-7-yl)-6-(piperidin-1-yl)pyrimidine-2,4-diamine |

TABLE 1-18

| | | |
|---|---|---|
| 107 | 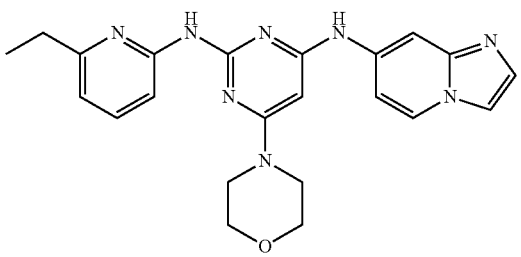 [SMILES: CCc1cccc(Nc2nc(Nc3ccn4ccnc4c3)cc(N3CCOCC3)n2)n1] | N2-(6-ethylpyridin-2-yl)-N4-(imidazo[1,2-a]pyridin-7-yl)-6-morpholinopyrimidine-2,4-diamine |

TABLE 1-18-continued

| | | |
|---|---|---|
| 108 | | N4-(imidazo[1,2-a]pyridin-7-yl)-6-morpholino-N2-(6-propylpyridin-2-yl)pyrimidine-2,4-diamine |
| 109 | | N2-(6-butylpyridin-2-yl)-N4-(imidazo[1,2-a]pyridin-7-yl)-6-morpholinopyrimidine-2,4-diamine |
| 110 | | N2-(6-cyclopropylpyridin-2-yl)-N4-(imidazo[1,2-a]pyridin-7-yl)-6-morpholinopyrimidine-2,4-diamine |
| 111 | | 1-(2-((4-ethylpyridin-2-yl)amino)-6-(imidazo[1,2-a]pyridin-7-ylamino)pyrimidin-4-yl)piperidin-4-ol |
| 112 | | N2-(4-ethylpyridin-2-yl)-N4-(imidazo[1,2-a]pyridin-7-yl)-6-(4-morpholinopiperidin-1-yl)pyrimidine-2,4-diamine |

TABLE 1-19

| | | |
|---|---|---|
| 113 | | 6-([1,4'-bipiperidin]-1'-yl)-N2-(4-ethylpyridin-2-yl)-N4-(imidazo[1,2-a]pyridin-7-yl)pyrimidine-2,4-diamine |
| 114 | | N2-(4-ethylpyridin-2-yl)-N4-(imidazo[1,2-a]pyridin-7-yl)-6-(4-methoxypiperidin-1-yl)pyrimidine-2,4-diamine |
| 115 | | 1-(2-((4-ethylpyridin-2-yl)amino)-6-(imidazo[1,2-a]pyridin-7-ylamino)pyrimidin-4-yl)azetidin-3-ol |
| 116 | | (R)-1-(2-((4-ethylpyridin-2-yl)amino)-6-(imidazo[1,2-a]pyridin-7-ylamino)pyrimidin-4-yl)pyrrolidin-3-ol |
| 117 | | (S)-1-(2-((4-ethylpyridin-2-yl)amino)-6-(imidazo[1,2-a]pyridin-7-ylamino)pyrimidin-4-yl)pyrrolidin-3-ol |

TABLE 1-20

| 118 | | 6-(azetidin-1-yl)-N2-(4-ethylpyridin-2-yl)-N4-(imidazo[1,2-a]pyridin-7-yl)pyrimidine-2,4-diamine |
|---|---|---|
| 119 | | (1-(2-((4-ethylpyridin-2-yl)amino)-6-(imidazo[1,2-a]pyridin-7-ylamino)pyrimidin-4-yl)piperidin-4-yl)methanol |
| 120 | | N2-(4-ethylpyridin-2-yl)-N4-(imidazo[1,2-a]pyridin-7-yl)-6-(1,4,7-trioxa-10-azacyclododecan-10-yl)pyrimidine-2,4-diamine |
| 121 | | N4-(imidazo[1,2-a]pyridin-7-yl)-N2-(6-isopropylpyridin-2-yl)-6-(piperidin-1-yl)pyrimidine-2,4-diamine |
| 122 | | N2-(6-(tert-butyl)pyridin-2-yl)-N4-(imidazo[1,2-a]pyridin-7-yl)-6-(piperidin-1-yl)pyrimidine-2,4-diamine |

TABLE 1-21

| | | | |
|---|---|---|---|
| 123 | 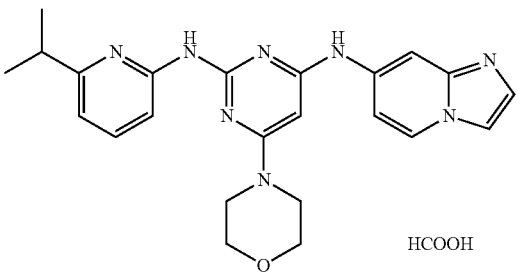 [SMILES: CC(C)c1cccc(Nc2nc(Nc3ccn4ccnc4c3)cc(N3CCOCC3)n2)n1 ; "HCOOH"] HCOOH | | N4-(imidazo[1,2-a]pyridin-7-yl)-N2-(6-isopropylpyridin-2-yl)-6-morpholinopyrimidine-2,4-diamine formate |
| 124 | 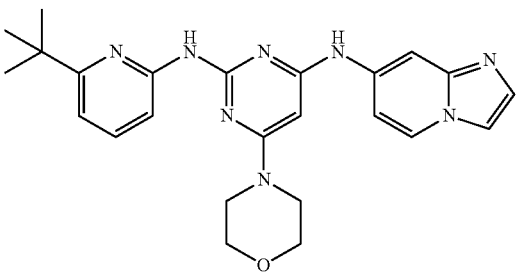 [SMILES: CC(C)(C)c1cccc(Nc2nc(Nc3ccn4ccnc4c3)cc(N3CCOCC3)n2)n1] | | N2-(6-(tert-butyl)pyridin-2-yl)-N4-(imidazo[1,2-a]pyridin-7-yl)-6-morpholinopyrimidine-2,4-diamine |
| 125 | 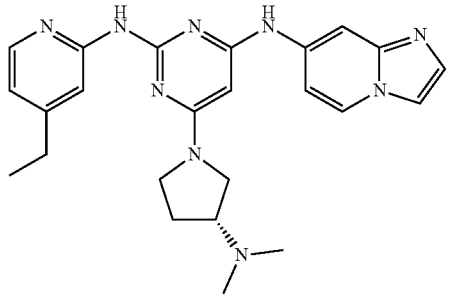 [SMILES: CCc1ccnc(Nc2nc(Nc3ccn4ccnc4c3)cc(N3CC[C@@H](N(C)C)C3)n2)c1] | | (R)-6-(3-(dimethylamino)pyrrolidin-1-yl)-N2-(4-ethylpyridin-2-yl)-N4-(imidazo[1,2-a]pyridin-7-yl)pyrimidine-2,4-diamine |
| 126 | 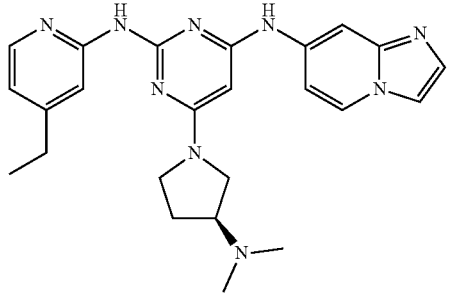 [SMILES: CCc1ccnc(Nc2nc(Nc3ccn4ccnc4c3)cc(N3CC[C@H](N(C)C)C3)n2)c1] | | (S)-6-(3-(dimethylamino)pyrrolidin-1-yl)-N2-(4-ethylpyridin-2-yl)-N4-(imidazo[1,2-a]pyridin-7-yl)pyrimidine-2,4-diamine |
| 127 | 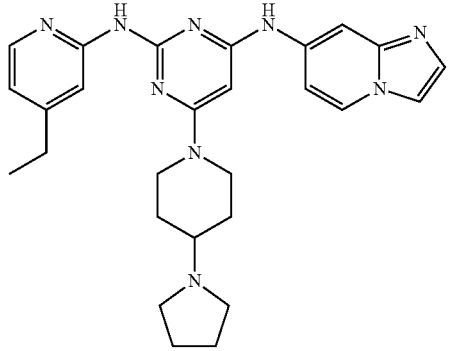 [SMILES: CCc1ccnc(Nc2nc(Nc3ccn4ccnc4c3)cc(N3CCC(N4CCCC4)CC3)n2)c1] | | N2-(4-ethylpyridin-2-yl)-N4-(imidazo[1,2-a]pyridin-7-yl)-6-(4-(pyrrolidin-1-yl)piperidin-1-yl)pyrimidine-2,4-diamine |

TABLE 1-22

| | | |
|---|---|---|
| 128 | | N4-(imidazo[1,2-a]pyridin-7-yl)-N2-(4-methoxypyridin-2-yl)-6-(pyrrolidin-1-yl)pyrimidine-2,4-diamine |
| 129 | | 6-(4-(dimethylamino)piperidin-1-yl)-N2-(4-ethylpyridin-2-yl)-N4-(imidazo[1,2-a]pyridin-7-yl)pyrimidine-2,4-diamine |
| 130 | | 1-(2-((4,6-dimethylpyridin-2-yl)amino)-6-(imidazo[1,2-a]pyridin-7-ylamino)pyrimidin-4-yl)piperidin-4-ol |
| 131 | | N2-(4,6-dimethylpyridin-2-yl)-N4-(imidazo[1,2-a]pyridin-7-yl)-6-(4-methoxypiperidin-1-yl)pyrimidine-2,4-diamine |
| 132 | | N2-(4,6-dimethylpyridin-2-yl)-N4-(imidazo[1,2-a]pyridin-7-yl)-6-(4-morpholinopiperidin-1-yl)pyrimidine-2,4-diamine |

TABLE 1-23

| | | |
|---|---|---|
| 133 | 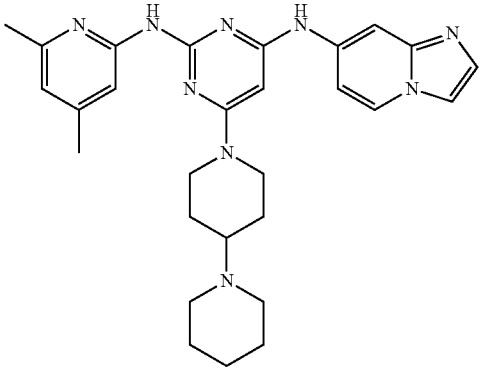 [SMILES: Cc1cc(C)nc(Nc2nc(Nc3ccn4ccnc4c3)cc(N3CCC(N4CCCCC4)CC3)n2)c1] | 6-([1,4'-bipiperidin]-1'-yl)-N2-(4,6-dimethylpyridin-2-yl)-N4-(imidazo[1,2-a]pyridin-7-yl)pyrimidine-2,4-diamine |
| 134 | 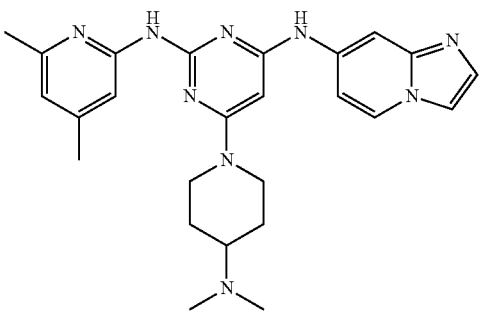 [SMILES: Cc1cc(C)nc(Nc2nc(Nc3ccn4ccnc4c3)cc(N3CCC(N(C)C)CC3)n2)c1] | 6-(4-(dimethylamino)piperidin-1-yl)-N2-(4,6-dimethylpyridin-2-yl)-N4-(imidazo[1,2-a]pyridin-7-yl)pyrimidine-2,4-diamine |
| 135 | 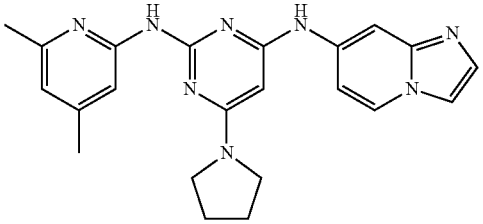 [SMILES: Cc1cc(C)nc(Nc2nc(Nc3ccn4ccnc4c3)cc(N3CCCC3)n2)c1] | N2-(4,6-dimethylpyridin-2-yl)-N4-(imidazo[1,2-a]pyridin-7-yl)-6-(pyrrolidin-1-yl)pyrimidine-2,4-diamine |
| 136 | 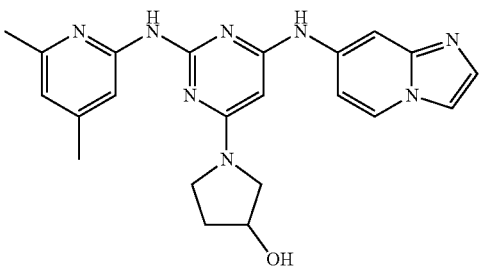 [SMILES: Cc1cc(C)nc(Nc2nc(Nc3ccn4ccnc4c3)cc(N3CCC(O)C3)n2)c1] | 1-(2-((4,6-dimethylpyridin-2-yl)amino)-6-(imidazo[1,2-a]pyridin-7-ylamino)pyrimidin-4-yl)pyrrolidin-3-ol |
| 137 | 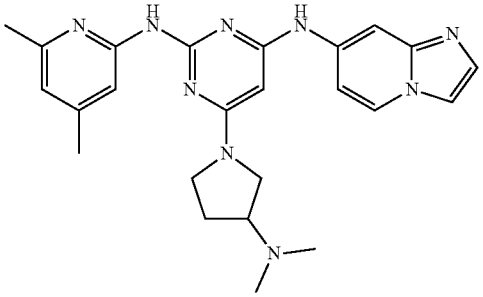 [SMILES: Cc1cc(C)nc(Nc2nc(Nc3ccn4ccnc4c3)cc(N3CCC(N(C)C)C3)n2)c1] | 6-(3-(dimethylamino)pyrrolidin-1-yl)-N2-(4,6-dimethylpyridin-2-yl)-N4-(imidazo[1,2-a]pyridin-7-yl)pyrimidine-2,4-diamine |

TABLE 1-24

| 138 | 6-(3,3-difluoropyrrolidin-1-yl)-N2-(4,6-dimethylpyridin-2-yl)-N4-(imidazo[1,2-a]pyridin-7-yl)pyrimidine-2,4-diamine |
| 139 | 6-(2,5-dihydro-1H-pyrrol-1-yl)-N2-(4,6-dimethylpyridin-2-yl)-N4-(imidazo[1,2-a]pyridin-7-yl)pyrimidine-2,4-diamine |
| 140 | N2-(4,6-dimethylpyridin-2-yl)-N4-(imidazo[1,2-a]pyridin-7-yl)-6-(3-methoxypyrrolidin-1-yl)pyrimidine-2,4-diamine |
| 141 | N2-(4-cyclopropyl-6-methylpyridin-2-yl)-N4-(imidazo[1,2-a]pyridin-7-yl)-6-(piperidin-1-yl)pyrimidine-2,4-diamine |
| 142 | N2-(4,6-dimethylpyridin-2-yl)-6-(3,3-dimethylpyrrolidin-1-yl)-N4-(imidazo[1,2-a]pyridin-7-yl)pyrimidine-2,4-diamine |

TABLE 1-25

| | | |
|---|---|---|
| 143 | 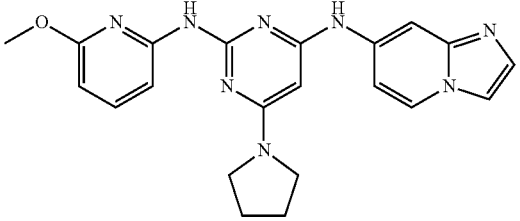 [SMILES: COc1cccc(Nc2nc(Nc3ccn4ccnc4c3)cc(N3CCCC3)n2)n1] | N4-(imidazo[1,2-a]pyridin-7-yl)-N2-(6-methoxypyridin-2-yl)-6-(pyrrolidin-1-yl)pyrimidine-2,4-diamine |
| 144 | 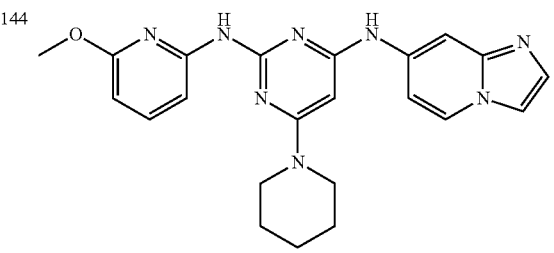 | N4-(imidazo[1,2-a]pyridin-7-yl)-N2-(6-methoxypyridin-2-yl)-6-(piperidin-1-yl)pyrimidine-2,4-diamine |
| 145 | 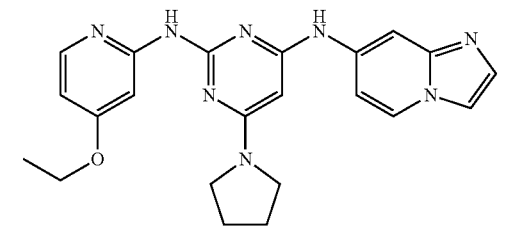 [SMILES: CCOc1ccnc(Nc2nc(Nc3ccn4ccnc4c3)cc(N3CCCC3)n2)c1] | N2-(4-ethoxypyridin-2-yl)-N4-(imidazo[1,2-a]pyridin-7-yl)-6-(pyrrolidin-1-yl)pyrimidine-2,4-diamine |
| 146 | 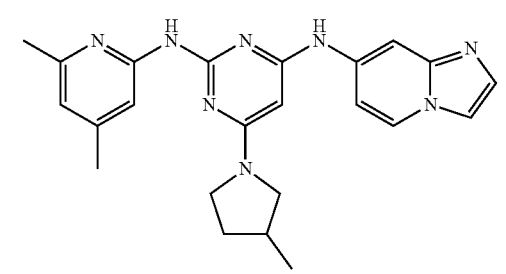 [SMILES: Cc1cc(C)nc(Nc2nc(Nc3ccn4ccnc4c3)cc(N3CCC(C)C3)n2)c1] | N2-(4,6-dimethylpyridin-2-yl)-N4-(imidazo[1,2-a]pyridin-7-yl)-6-(3-methylpyrrolidin-1-yl)pyrimidine-2,4-diamine |
| 147 | 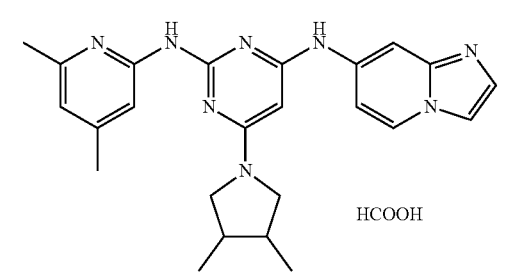 [SMILES: Cc1cc(C)nc(Nc2nc(Nc3ccn4ccnc4c3)cc(N3CC(C)C(C)C3)n2)c1 ; "HCOOH"] | N2-(4,6-dimethylpyridin-2-yl)-6-(3,4-dimethylpyrrolidin-1-yl)-N4-(imidazo[1,2-a]pyridin-7-yl)pyrimidine-2,4-diamine formate |

TABLE 1-26

| | | |
|---|---|---|
| 148 | | 6-([1,3'-bipyrrolidin]-1'-yl)-N2-(4,6-dimethylpyridin-2-yl)-N4-(imidazo[1,2-a]pyridin-7-yl)pyrimidine-2,4-diamine |
| 149 | | N2-(4,6-dimethylpyridin-2-yl)-N4-(imidazo[1,2-a]pyridin-7-yl)-6-(3-morpholinopyrrolidin-1-yl)pyrimidine-2,4-diamine |
| 150 | | N2-(6-ethoxypyridin-2-yl)-N4-(imidazo[1,2-a]pyridin-7-yl)-6-(pyrrolidin-1-yl)pyrimidine-2,4-diamine |
| 151 | | N4-(imidazo[1,2-a]pyridin-7-yl)-N2-(6-propoxypyridin-2-yl)-6-(pyrrolidin-1-yl)pyrimidine-2,4-diamine |
| 152 | | N4-(imidazo[1,2-a]pyridin-7-yl)-N2-[6-(2-methoxyethoxy)pyridin-2-yl]-6-(pyrrolidin-1-yl)pyrimidine-2,4-diamine |

TABLE 1-27

| | | |
|---|---|---|
| 153 | | N4-(imidazo[1,2-a]pyridin-7-yl)-N2-(6-isopropoxypyridin-2-yl)-6-(pyrrolidin-1-yl)pyrimidine-2,4-diamine |
| 154 | | N4-(imidazo[1,2-a]pyridin-7-yl)-N2-[6-(2-morpholinoethoxy)pyridin-2-yl]-6-(pyrrolidin-1-yl)pyrimidine-2,4-diamine |
| 155 | | N2-{6-[2-(dimethylamino)ethoxy]pyridin-2-yl}-N4-(imidazo[1,2-a]pyridin-7-yl)-6-(pyrrolidin-1-yl)pyrimidine-2,4-diamine |
| 156 | | N2-{6-[2-(tert-butoxy)ethoxy]pyridin-2-yl}-N4-(imidazo[1,2-a]pyridin-7-yl)-6-(pyrrolidin-1-yl)pyrimidine-2,4-diamine |
| 157 | | 2-[(6-{[4-(imidazo[1,2-a]pyridin-7-ylamino)-6-(pyrrolidin-1-yl)pyrimidin-2-yl]amino}pyridin-2-yl)oxy]ethanol |

TABLE 1-28

| | | |
|---|---|---|
| 158 | | N4-(imidazo[1,2-a]pyridin-7-yl)-N2-(6-isobutoxypyridin-2-yl)-6-(pyrrolidin-1-yl)pyrimidine-2,4-diamine |

TABLE 1-28-continued

| | Structure | Name |
|---|---|---|
| 159 | 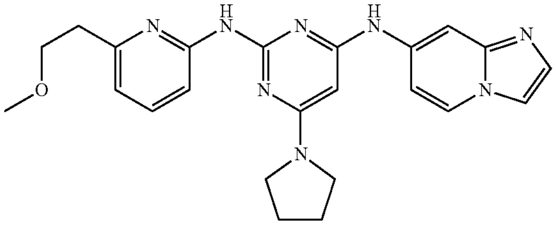 [SMILES: CCCOc1cccc(Nc2nc(Nc3ccn4ccnc4c3)cc(N3CCCC3)n2)n1] | N4-(imidazo[1,2-a]pyridin-7-yl)-N2-[6-(2-methoxyethyl)pyridin-2-yl]-6-(pyrrolidin-1-yl)pyrimidine-2,4-diamine |
| 160 | 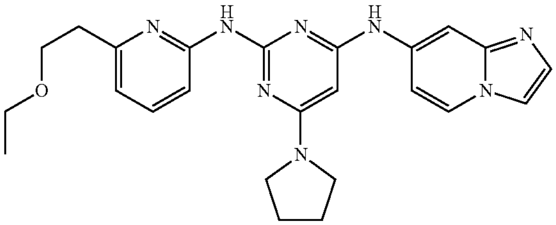 [SMILES: CCOCCc1cccc(Nc2nc(Nc3ccn4ccnc4c3)cc(N3CCCC3)n2)n1] | N2-[6-(2-ethoxyethyl)pyridin-2-yl]-N4-(imidazo[1,2-a]pyridin-7-yl)-6-(pyrrolidin-1-yl)pyrimidine-2,4-diamine |
| 161 | 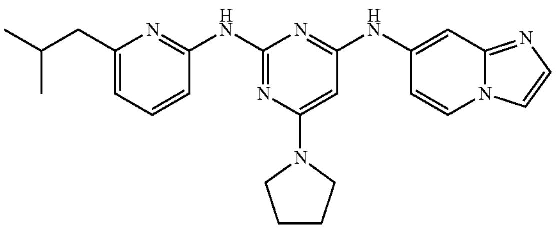 [SMILES: CC(C)Cc1cccc(Nc2nc(Nc3ccn4ccnc4c3)cc(N3CCCC3)n2)n1] | N4-(imidazo[1,2-a]pyridin-7-yl)-N2-(6-isobutylpyridin-2-yl)-6-(pyrrolidin-1-yl)pyrimidine-2,4-diamine |
| 162 | 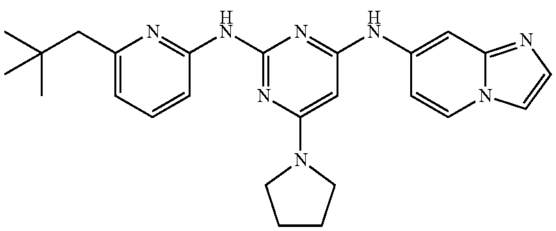 [SMILES: CC(C)(C)Cc1cccc(Nc2nc(Nc3ccn4ccnc4c3)cc(N3CCCC3)n2)n1] | N4-(imidazo[1,2-a]pyridin-7-yl)-N2-(6-neopentylpyridin-2-yl)-6-(pyrrolidin-1-yl)pyrimidine-2,4-diamine |

TABLE 1-29

| | Structure | Name |
|---|---|---|
| 163 | (3HCOOH) | N4-(imidazo[1,2-a]pyridin-7-yl)-6-(pyrrolidin-1-yl)-N2-{6-[2-(pyrrolidin-1-yl)ethyl]pyridin-2-yl}pyrimidine-2,4-diamine triformate |
| 164 | 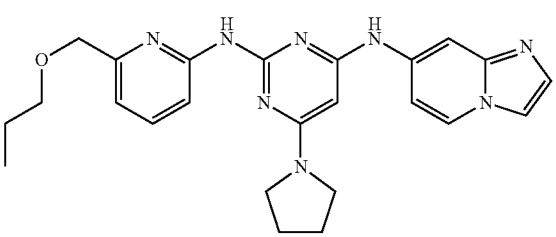 [SMILES: CCCOCc1cccc(Nc2nc(Nc3ccn4ccnc4c3)cc(N3CCCC3)n2)n1] | N4-(imidazo[1,2-a]pyridin-7-yl)-N2-[6-(propoxymethyl)pyridin-2-yl]-6-(pyrrolidin-1-yl)pyrimidine-2,4-diamine |

TABLE 1-29-continued

| | | |
|---|---|---|
| 165 | | N2-(6-butylpyridin-2-yl)-N4-(imidazo[1,2-a]pyridin-7-yl)-6-(pyrrolidin-1-yl)pyrimidine-2,4-diamine |
| 166 | | 6-(azetidin-1-yl)-N2-(4,6-dimethylpyridin-2-yl)-N4-(imidazo[1,2-a]pyridin-7-yl)pyrimidine-2,4-diamine |
| 167 | | 6-(azetidin-1-yl)-N2-(6-butylpyridin-2-yl)-N4-(imidazo[1,2-a]pyridin-7-yl)pyrimidine-2,4-diamine |

TABLE 1-30

| | | |
|---|---|---|
| 168 | | N2-(6-butylpyridin-2-yl)-6-(3,3-dimethylpyrrolidin-1-yl)-N4-(imidazo[1,2-a]pyridin-7-yl)pyrimidine-2,4-diamine |
| 169 | | N2-(6-butylpyridin-2-yl)-N4-(imidazo[1,2-a]pyridin-7-yl)-6-(8-oxa-2-azaspiro[4.5]decan-2-yl)pyrimidine-2,4-diamine |

TABLE 1-30-continued

| | | |
|---|---|---|
| 170 | | 6-(3,3-dimethylpyrrolidin-1-yl)-N2-(4-ethylpyridin-2-yl)-N4-(imidazo[1,2-a]pyridin-7-yl)pyrimidine-2,4-diamine |
| 171 | | N2-[6-(ethoxymethyl)pyridin-2-yl]-N4-(imidazo[1,2-a]pyridin-7-yl)-6-(pyrrolidin-1-yl)pyrimidine-2,4-diamine |
| 172 | | N2-{6-[2-(dimethylamino)ethyl]pyridin-2-yl}-N4-(imidazo[1,2-a]pyridin-7-yl)-6-(pyrrolidin-1-yl)pyrimidine-2,4-diamine |

TABLE 1-31

| | | |
|---|---|---|
| 173 | | N2-(6-butylpyridin-2-yl)-N4-(imidazo[1,2-a]pyridin-7-yl)-6-(2-azaspiro[4.4]nonan-2-yl)pyrimidine-2,4-diamine |
| 174 | | N2-(4,6-dimethylpyridin-2-yl)-N4-(imidazo[1,2-a]pyridin-7-yl)-6-(2-azaspiro[4.4]nonan-2-yl)pyrimidine-2,4-diamine |

TABLE 1-31-continued

| | | |
|---|---|---|
| 175 | | N2-(4,6-dimethylpyridin-2-yl)-N4-(imidazo[1,2-a]pyridin-7-yl)-6-(8-oxa-2-azaspiro[4.5]decan-2-yl)pyrimidine-2,4-diamine |
| 176 | | N2-(4,6-dimethylpyridin-2-yl)-6-[(3aR,6aS)-hexahydrocyclopenta[c]pyrrol-2(1H)-yl]-N4-(imidazo[1,2-a]pyridin-7-yl)pyrimidine-2,4-diamine |
| 177 | | 6-(3,3-dimethylazetidin-1-yl)-N2-(4,6-dimethylpyridin-2-yl)-N4-(imidazo[1,2-a]pyridin-7-yl)pyrimidine-2,4-diamine |

TABLE 1-32

| | | |
|---|---|---|
| 178 | | N2-(4,6-dimethylpyridin-2-yl)-N4-(imidazo[1,2-a]pyridin-7-yl)-6-(2-oxa-6-azaspiro[3.3]heptan-6-yl)pyrimidine-2,4-diamine |
| 179 | | N2-(6-butylpyridin-2-yl)-6-((3aR,6aS)-hexahydrocyclopenta[c]pyrrol-2(1H)-yl)-N4-(imidazo[1,2-a]pyridin-7-yl)pyrimidine-2,4-diamine |

TABLE 1-32-continued

| # | Structure | Name |
|---|---|---|
| 180 | 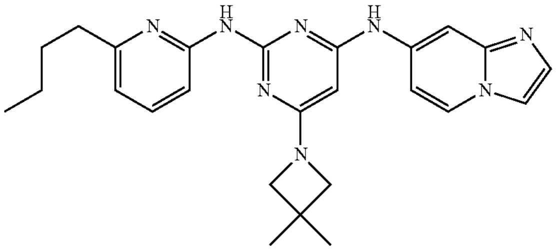 [SMILES: CCCCc1cccc(Nc2nc(Nc3ccn4ccnc4c3)cc(N3CC(C)(C)C3)n2)n1] | N2-(6-butylpyridin-2-yl)-6-(3,3-dimethylazetidin-1-yl)-N4-(imidazo[1,2-a]pyridin-7-yl)pyrimidine-2,4-diamine |
| 181 | 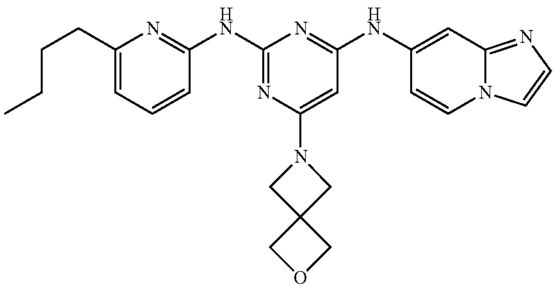 [SMILES: CCCCc1cccc(Nc2nc(Nc3ccn4ccnc4c3)cc(N3CC4(COC4)C3)n2)n1] | N2-(6-butylpyridin-2-yl)-N4-(imidazo[1,2-a]pyridin-7-yl)-6-(2-oxa-6-azaspiro[3.3]heptan-6-yl)pyrimidine-2,4-diamine |
| 182 | 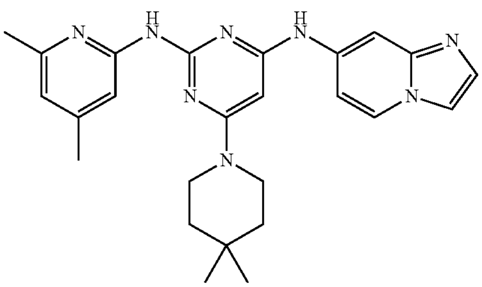 [SMILES: Cc1cc(C)nc(Nc2nc(Nc3ccn4ccnc4c3)cc(N3CCC(C)(C)CC3)n2)c1] | 6-(4,4-dimethylpiperidin-1-yl)-N2-(4,6-dimethylpyridin-2-yl)-N4-(imidazo[1,2-a]pyridine-7-yl)pyrimidine-2,4-diamine |

TABLE 1-33

| # | Structure | Name |
|---|---|---|
| 183 | 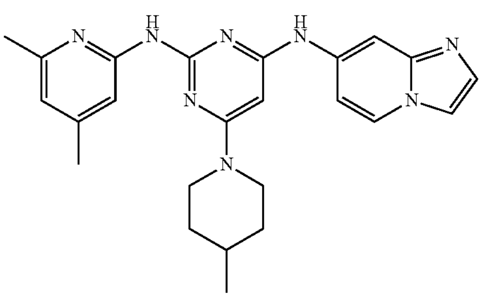 | N2-(4,6-dimethylpyridin-2-yl)-N4-(imidazo[1,2-a]pyridin-7-yl)-6-(4-methylpiperidin-1-yl)pyrimidine-2,4-diamine |
| 184 | 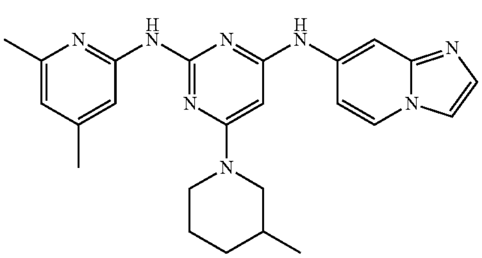 [SMILES: Cc1cc(C)nc(Nc2nc(Nc3ccn4ccnc4c3)cc(N3CCCC(C)C3)n2)c1] | N2-(4,6-dimethylpyridin-2-yl)-N4-(imidazo[1,2-a]pyridin-7-yl)-6-(3-methylpiperidin-1-yl)pyrimidine-2,4-diamine |

TABLE 1-33-continued

| | | |
|---|---|---|
| 185 | | (S)-N2-(4,6-dimethylpyridin-2-yl)-6-(3-fluoropyrrolidin-1-yl)-N4-(imidazo[1,2-a]pyridin-7-yl)pyrimidine-2,4-diamine |
| 186 | | (R)-N2-(4,6-dimethylpyridin-2-yl)-6-(3-fluoropyrrolidin-1-yl)-N4-(imidazo[1,2-a]pyridin-7-yl)pyrimidine-2,4-diamine |
| 187 | | N2-(6-butyl-4-methylpyridin-2-yl)-N4-(imidazo[1,2-a]pyridin-7-yl)-6-(piperidin-1-yl)pyrimidine-2,4-diamine |

TABLE 1-34

| | | |
|---|---|---|
| 188 | | N4-(imidazo[1,2-a]pyridin-7-yl)-N2-(6-isobutyl-4-methylpyridin-2-yl)-6-(piperidin-1-yl)pyrimidine-2,4-diamine |
| 189 | | N2-(6-ethyl-4-methylpyridin-2-yl)-N4-(imidazo[1,2-a]pyridin-7-yl)-6-(piperidin-1-yl)pyrimidine-2,4-diamine |

TABLE 1-34-continued

| 190 | 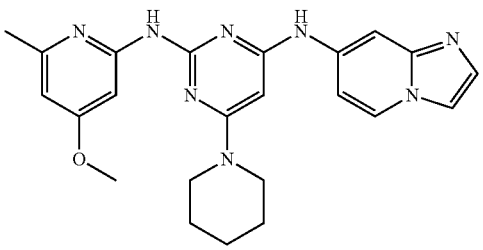 [SMILES: COc1cc(C)nc(Nc2nc(Nc3ccn4ccnc4c3)cc(N3CCCCC3)n2)c1] | N4-(imidazo[1,2-a]pyridin-7-yl)-N2-(4-methoxy-6-methyl pyridin-2-yl)-6-(piperidin-1-yl)pyrimidine-2,4-diamine |
| 191 | 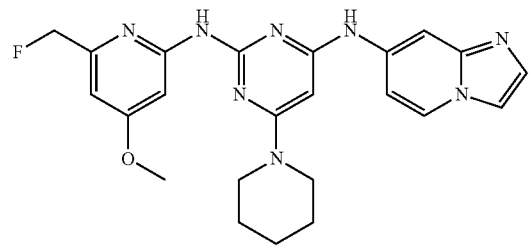 [SMILES: COc1cc(CF)nc(Nc2nc(Nc3ccn4ccnc4c3)cc(N3CCCCC3)n2)c1] | N2-(6-(fluoromethyl)-4-methoxypyridin-2-yl)-N4-(imidazo[1,2-a]pyridin-7-yl)-6-(piperidin-1-yl)pyrimidine-2,4-diamine |
| 192 | 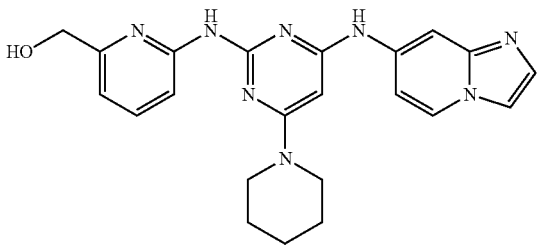 [SMILES: OCc1cccc(Nc2nc(Nc3ccn4ccnc4c3)cc(N3CCCCC3)n2)n1] | (6-{[4-(imidazo[1,2-a]pyridin-7-ylamino)-6-(piperidin-1-yl)pyrimidin-2-yl]amino}pyridin-2-yl)methanol |

TABLE 1-35

| 193 | 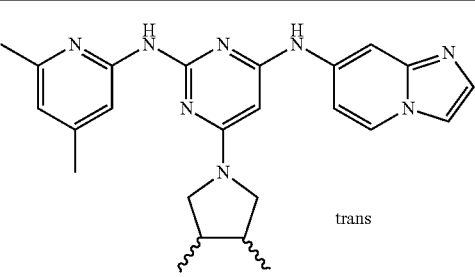 | N2-(4,6-dimethylpyridin-2-yl)-6-[trans-3,4-dimethylpyrrolidin-1-yl]-N4-(imidazo[1,2-a]pyridin-7-yl)pyrimidine-2,4-diamine |
| 194 | 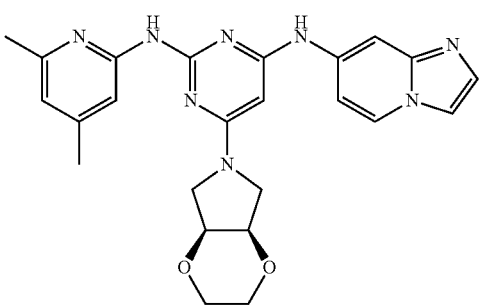 [SMILES: Cc1cc(C)nc(Nc2nc(Nc3ccn4ccnc4c3)cc(N3C[C@@H]4OCCO[C@@H]4C3)n2)c1] | N2-(4,6-dimethylpyridin-2-yl)-N4-(imidazo[1,2-a]pyridin-7-yl)-6-[(4aR,7aS)-tetrahydro-2H-[1,4]dioxino[2,3-c]pyrrol-6(3H)-yl]pyrimidine-2,4-diamine |

TABLE 1-35-continued

| | | |
|---|---|---|
| 195 | [structure] | N2-(4,6-dimethylpyridin-2-yl)-N4-(imidazo[1,2-a]pyridin-7-yl)-N6-phenylpyrimidine-2,4,6-triamine |
| 196 | [structure] | N4-benzyl-N2-(4,6-dimethylpyridin-2-yl)-N6-(imidazo[1,2-a]pyridin-7-yl)pyrimidine-2,4,6-triamine |
| 197 | [structure] | N2-(6-butyl-4-methoxypyridin-2-yl)-N4-(imidazo[1,2-a]pyridin-7-yl)-6-(piperidin-1-yl)pyrimidine-2,4-diamine |

TABLE 1-36

| | | |
|---|---|---|
| 198 | [structure] | N2-(4,6-dimethylpyridin-2-yl)-N4-(imidazo[1,2-a]pyridin-7-yl)-N6-(piperidin-1-yl)pyrimidine-2,4,6-triamine |
| 199 | [structure] | N2-(4,6-dimethylpyridin-2-yl)-N4-(imidazo[1,2-a]pyridin-7-yl)-N6-morpholinopyrimidine-2,4,6-triamine |

TABLE 1-36-continued

| | | |
|---|---|---|
| 200 | | N2-(4,6-dimethylpyridin-2-yl)-N4-(imidazo[1,2-a]pyridin-7-yl)-N6-(1H-pyrrol-1-yl)pyrimidine-2,4,6-triamine |
| 201 | | N2-(6-butyl-4-ethylpyridin-2-yl)-N4-(imidazo[1,2-a]pyridin-7-yl)-6-(piperidin-1-yl)pyrimidine-2,4-diamine |
| 202 | | N2-(5-fluoro-6-methylpyridin-2-yl)-N4-(imidazo[1,2-a]pyridin-7-yl)-6-(piperidin-1-yl)pyrimidine-2,4-diamine |

TABLE 1-37

| | | |
|---|---|---|
| 203 | | N2-(5-chloro-6-methylpyridin-2-yl)-N4-(imidazo[1,2-a]pyridin-7-yl)-6-(piperidin-1-yl)pyrimidine-2,4-diamine |
| 204 | | N2-(5-fluoro-4-methylpyridin-2-yl)-N4-(imidazo[1,2-a]pyridin-7-yl)-6-(piperidin-1-yl)pyrimidine-2,4-diamine |
| 205 | | N2-(4-chloro-6-methylpyridin-2-yl)-N4-(imidazo[1,2-a]pyridin-7-yl)-6-(piperidin-1-yl)pyrimidine-2,4-diamine |

TABLE 1-37-continued

| | | |
|---|---|---|
| 206 | | N2-(4,6-dimethylpyridin-2-yl)-N4-(imidazo[1,2-a]pyridin-7-yl)-N6-(pyrrolidin-1-yl)pyrimidine-2,4,6-triamine |
| 207 | | N4-(imidazo[1,2-a]pyridin-7-yl)-N2-(4-methoxypyridin-2-yl)-6-(2-azaspiro[4.4]nonan-2-yl)pyrimidine-2,4-diamine |

TABLE 1-38

| | | |
|---|---|---|
| 208 | | N2-(4-ethylpyridin-2-yl)-N4-(imidazo[1,2-a]pyridin-7-yl)-6-(2-azaspiro[4.4]nonan-2-yl)pyrimidine-2,4-diamine |
| 209 | | 6-(3,3-dimethylpyrrolidin-1-yl)-N4-(imidazo[1,2-a]pyridin-7-yl)-N2-(4-methoxypyridin-2-yl)pyrimidine-2,4-diamine |
| 210 | | N2-(6-chloro-4-methylpyridin-2-yl)-N4-(imidazo[1,2-a]pyridin-7-yl)-6-(piperidin-1-yl)pyrimidine-2,4-diamine |

TABLE 1-38-continued

| | | |
|---|---|---|
| 211 | 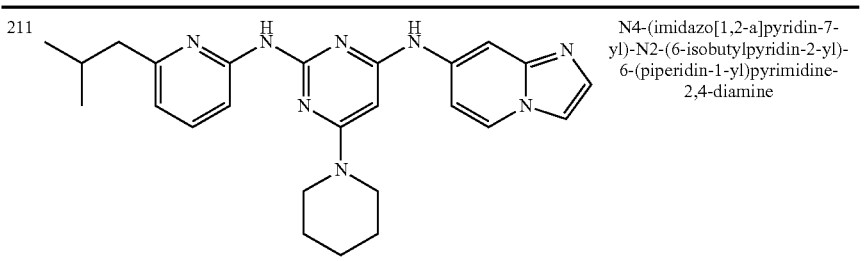 | N4-(imidazo[1,2-a]pyridin-7-yl)-N2-(6-isobutylpyridin-2-yl)-6-(piperidin-1-yl)pyrimidine-2,4-diamine |
| 212 | 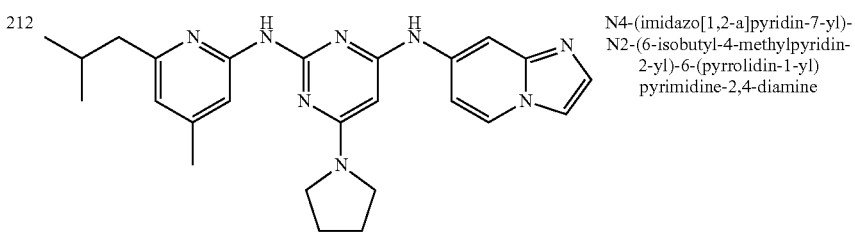 | N4-(imidazo[1,2-a]pyridin-7-yl)-N2-(6-isobutyl-4-methylpyridin-2-yl)-6-(pyrrolidin-1-yl)pyrimidine-2,4-diamine |

TABLE 1-39

| | | |
|---|---|---|
| 213 | 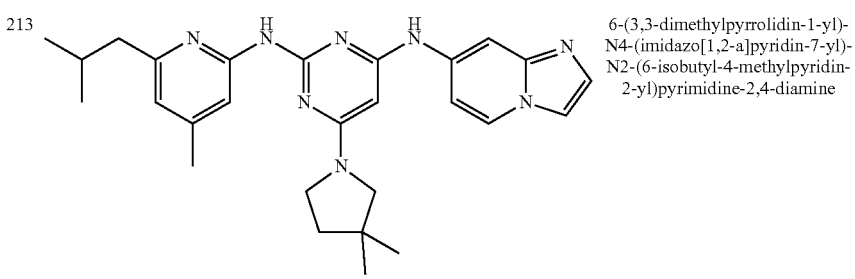 | 6-(3,3-dimethylpyrrolidin-1-yl)-N4-(imidazo[1,2-a]pyridin-7-yl)-N2-(6-isobutyl-4-methylpyridin-2-yl)pyrimidine-2,4-diamine |
| 214 | 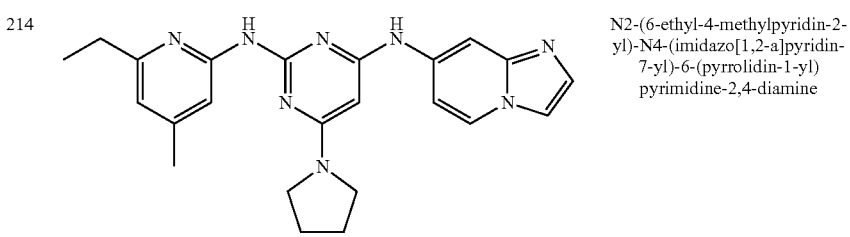 | N2-(6-ethyl-4-methylpyridin-2-yl)-N4-(imidazo[1,2-a]pyridin-7-yl)-6-(pyrrolidin-1-yl)pyrimidine-2,4-diamine |
| 215 | 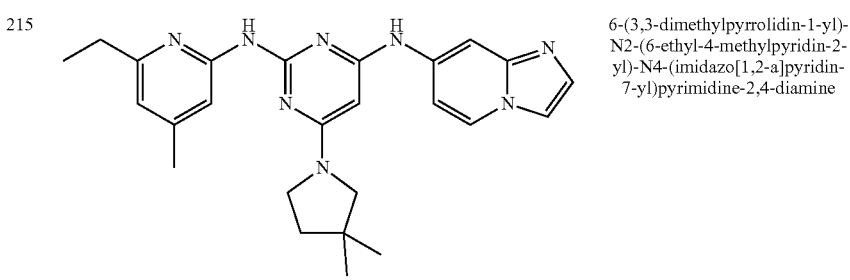 | 6-(3,3-dimethylpyrrolidin-1-yl)-N2-(6-ethyl-4-methylpyridin-2-yl)-N4-(imidazo[1,2-a]pyridin-7-yl)pyrimidine-2,4-diamine |

TABLE 1-39-continued

| | | |
|---|---|---|
| 216 | 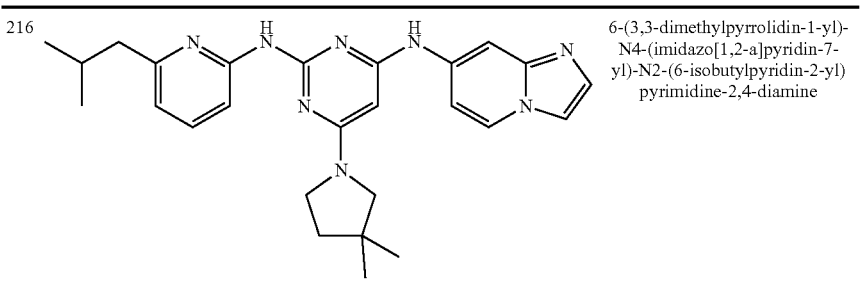 | 6-(3,3-dimethylpyrrolidin-1-yl)-N4-(imidazo[1,2-a]pyridin-7-yl)-N2-(6-isobutylpyridin-2-yl)pyrimidine-2,4-diamine |
| 217 | 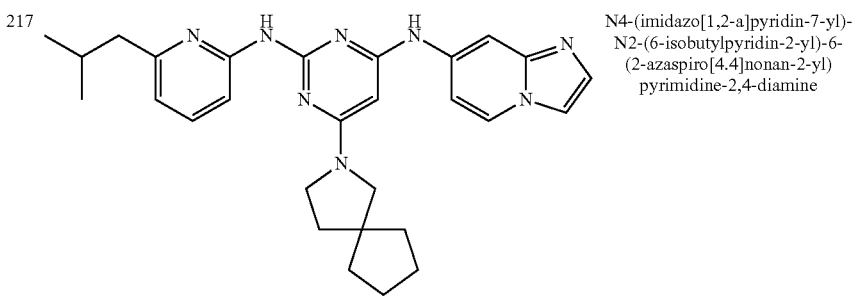 | N4-(imidazo[1,2-a]pyridin-7-yl)-N2-(6-isobutylpyridin-2-yl)-6-(2-azaspiro[4.4]nonan-2-yl)pyrimidine-2,4-diamine |

TABLE 1-40

| | | |
|---|---|---|
| 218 | 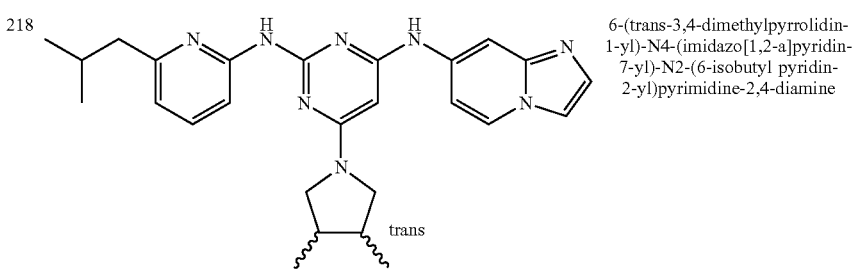 | 6-(trans-3,4-dimethylpyrrolidin-1-yl)-N4-(imidazo[1,2-a]pyridin-7-yl)-N2-(6-isobutyl pyridin-2-yl)pyrimidine-2,4-diamine |
| 219 | 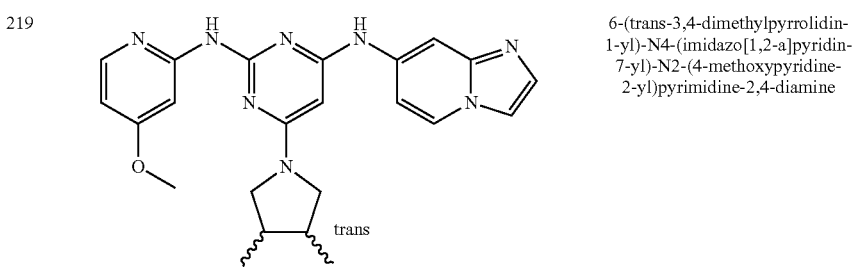 | 6-(trans-3,4-dimethylpyrrolidin-1-yl)-N4-(imidazo[1,2-a]pyridin-7-yl)-N2-(4-methoxypyridine-2-yl)pyrimidine-2,4-diamine |
| 220 | 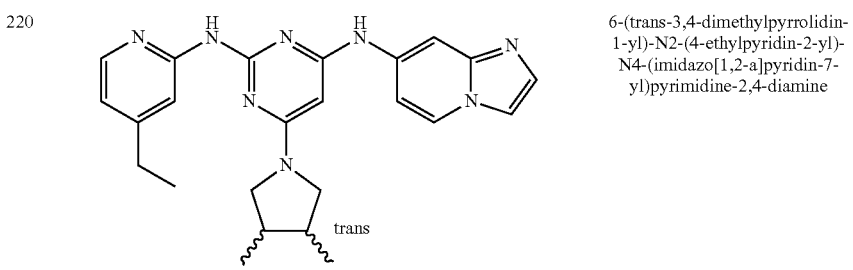 | 6-(trans-3,4-dimethylpyrrolidin-1-yl)-N2-(4-ethylpyridin-2-yl)-N4-(imidazo[1,2-a]pyridin-7-yl)pyrimidine-2,4-diamine |

TABLE 1-40-continued

| | | |
|---|---|---|
| 221 | [structure] | N4-(imidazo[1,2-a]pyridin-7-yl)-N2-(4-methoxy-6-methylpyridin-2-yl)-6-(pyrrolidin-1-yl)pyrimidine-2,4-diamine |
| 222 | [structure] | 6-(3,3-dimethylpyrrolidin-1-yl)-N4-(imidazo[1,2-a]pyridin-7-yl)-N2-(4-methoxy-6-methylpyridin-2-yl)pyrimidine-2,4-diamine carbonate |

TABLE 2-1

| Example No. | $^1$H-NMR δ (ppm) | LCMS m/z [M + H]$^+$ |
|---|---|---|
| 1 | (DMSO-d$_6$) δ 9.17 (s, 1H), 8.96 (s, 1H), 8.48-8.39 (m, 1H), 8.34 (d, J = 7.3 Hz, 1H), 8.15-8.05 (m, 1H), 8.03 (dd, J = 2.9, 8.8 Hz, 1H), 7.72 (s, 1H), 7.39 (s, 1H), 6.99 (dd, J = 2.0, 7.3 Hz, 1H), 6.75-6.70 (m, 1H), 5.55 (s, 1H), 3.82 (s, 3H), 3.75-3.65 (m, 4H), 3.50-3.49 (m, 4H). | 419.2 |
| 2 | (CDCl$_3$) δ 8.01 (dd, J = 7.3, 0.7 Hz, 1H), 7.97-7.92 (m, 1H), 7.92-7.90 (m, 1H), 7.57-7.54 (m, 1H), 7.50-7.47 (m, 2H), 7.11-7.06 (m, 1H), 6.92 (dd, J = 7.3, 2.1 Hz, 1H), 6.60-6.57 (m, 1H), 5.65 (s, 1H), 3.81-3.75 (m, 4H), 3.60-3.53 (m, 4H), 2.40-2.35 (m, 3H), 2.29-2.26 (m, 3H). | 417.0 |
| 3 | (DMSO-d$_6$) δ 14.85 (s, 1H), 11.02 (s, 1H), 9.33-9.26 (m, 2H), 9.02-8.96 (m, 2H), 8.75-8.69 (m, 1H), 8.60-8.55 (m, 1H), 8.17-8.12 (m, 1H), 8.05-8.00 (m, 1H), 7.46-7.39 (m, 1H), 7.17-7.11 (m, 2H), 6.35 (s, 1H), 3.79-3.71 (m, 4H), 3.71-3.62 (m, 4H). | 389.1 |
| 4 | (DMSO-d$_6$) δ 9.24 (br. s, 1H), 9.22 (br. s, 1H), 8.90-8.80 (m, 1H), 8.36 (d, J = 7.3 Hz, 1H), 8.18-8.09 (m, 3H), 7.74 (s, 1H), 7.42 (s, 1H), 7.28 (dd, J = 4.7, 8.1 Hz, 1H), 7.10-6.98 (m, 1H), 5.61 (s, 1H), 3.71-3.69 (m, 4H), 3.48-3.47 (m, 4H). | 389.3 |
| 5 | (DMSO-d$_6$) δ 9.24 (s, 1H), 8.47 (dd, J = 1.5, 7.8 Hz, 1H), 8.36 (d, J = 7.3 Hz, 1H), 8.00-7.95 (m, 1H), 7.79-7.73 (m, 2H), 7.55 (s, 1H), 7.41 (s, 1H), 7.00-6.95 (m, 2H), 5.62 (s, 1H), 3.97 (s, 3H), 3.73-3.67 (m, 4H), 3.55-3.40 (m, 4H). | 419.3 |
| 6 | (DMSO-d$_6$) δ 9.53 (s, 1H), 9.29 (s, 1H), 8.75-8.62 (m, 1H), 8.42-8.35 (m, 1H), 8.25-8.15 (m, 1H), 8.07 (d, J = 2.5 Hz, 1H), 8.05-8.00 (m, 1H), 7.75 (s, 1H), 7.41 (d, J = 1.5 Hz, 1H), 7.01 (dd, J = 2.0, 7.3 Hz, 1H), 5.65 (s, 1H), 3.72-3.70 (m, 4H), 3.49-3.47 (m, 4H). | 407.3 |
| 8 | (DMSO-d$_6$) δ 9.42 (s, 1H), 9.29 (s, 1H), 9.13-9.11 (m, 2H), 8.71 (s, 1H), 8.42-8.35 (m, 1H), 8.10-8.02 (m, 1H), 7.74 (s, 1H), 7.41 (s, 1H), 6.99 (dd, J = 2.0, 7.3 Hz, 1H), 5.65 (s, 1H), 3.71-3.70 (m, 4H), 3.48-3.47 (m, 4H). | 390.3 |

TABLE 2-2

| | | |
|---|---|---|
| 9 | (DMSO-d$_6$) δ 9.14 (br. s, 1H), 8.62 (s, 1H), 8.40-8.30 (m, 1H), 8.25 (d, J = 7.3 Hz, 1H), 8.08-7.98 (m, 1H), 7.67-7.63 (m, 2H), 7.36 (d, J = 0.9 Hz, 1H), 7.11 (dd, J = 4.9, 7.3 Hz, 1H), 7.05-6.95 (m, 1H), 5.23 (s, 1H), 3.66-3.64 (m, 4H), 3.40-3.37 (m, 4H), 2.22 (s, 3H). | 403.2 |
| 10 | (DMSO-d$_6$) δ 9.27 (s, 1H), 9.07 (s, 1H), 8.40-8.30 (m, 1H), 8.06-7.98 (m, 2H), 7.74 (s, 1H), 7.65-7.55 (m, 1H), 7.41 (s, 1H), 7.24-7.14 (m, 1H), 6.85-6.75 (m, 1H), 5.63 (s, 1H), 3.71-3.64 (m, 4H), 3.48-3.40 (m, 4H), 2.39 (s, 3H). | 403.2 |
| 11 | (DMSO-d$_6$) δ 9.23 (br. s, 1H), 8.71 (br. s, 1H), 8.42-8.38 (m, 1H), 8.36-8.30 (m, 1H), 8.05-7.95 (m, 1H), 7.90-7.80 (m, 1H), 7.65-7.75 (m, 1H), | 407.3 |

TABLE 2-2-continued

| | | |
|---|---|---|
| | 7.45-7.35 (m, 1H), 7.31-7.29 (m, 1H), 7.05-6.95 (m, 1H), 5.60 (s, 1H), 3.69-3.65 (m, 4H), 3.44-3.41 (m, 4H). | |
| 12 | (DMSO-$d_6$) δ 9.27 (br. s, 1H), 9.23 (br. s, 1H), 8.54-8.48 (m, 1H), 8.36 (d, J = 7.3 Hz, 1H), 8.32-8.22 (m, 1H), 8.15-8.02 (m, 1H), 7.73 (s, 1H), 7.40 (s, 1H), 7.09 (dd, J = 3.4, 8.8 Hz, 1H), 6.98 (dd, J = 2.0, 7.3 Hz, 1H), 5.60 (s, 1H), 3.74-3.69 (m, 4H), 3.47-3.46 (m, 4H). | 407.4 |
| 13 | (DMSO-$d_6$) δ 9.55 (br. s, 1H), 9.38 (br. s, 1H), 8.44-8.39 (m, 1H), 8.35-8.25 (m, 1H), 8.25-8.18 (m, 1H), 8.18-8.10 (m, 1H), 7.85-7.75 (m, 1H), 7.72-7.60 (m, 1H), 7.56-7.45 (m, 1H), 7.35-7.20 (m, 1H), 5.69 (s, 1H), 3.81-3.65 (m, 4H), 3.52-3.41 (m, 4H). | 407.2 |
| 14 | (DMSO-$d_6$) δ 9.68 (s, 1H), 9.30 (s, 1H), 8.40-8.35 (m, 1H), 8.11-8.07 (m, 2H), 7.88-7.82 (m, 1H), 7.74 (s, 1H), 7.41 (d, J = 1.0 Hz, 1H), 7.18 (dd, J = 2.0, 7.3 Hz, 1H), 6.63 (dd, J = 2.5, 7.8 Hz, 1H), 5.66 (s, 1H), 3.72-3.70 (m, 4H), 3.49-3.47 (m, 4H). | 407.2 |
| 15 | (DMSO-$d_6$) δ 9.16 (s, 1H), 8.92 (s, 1H), 8.36-8.33 (m, 2H), 8.14-8.02 (m, 1H), 8.01 (dd, J = 2.7, 9.1 Hz, 1H), 7.72 (s, 1H), 7.39 (d, J = 1.0 Hz, 1H), 7.03 (dd, J = 2.0, 7.3 Hz, 1H), 6.72-6.65 (m, 1H), 5.56 (s, 1H), 5.17 (dt, J = 6.1, 12.2 Hz, 1H), 3.70-3.67 (m, 4H), 3.46-3.44 (m, 4H), 1.27 (d, J = 5.9 Hz, 6H). | 447.3 |

TABLE 2-3

| | | |
|---|---|---|
| 16 | (DMSO-$d_6$) δ 9.58 (s, 1H), 9.38-9.29 (m, 2H), 8.85 (d, J = 4.4 Hz, 2H), 8.38-8.30 (m, 1H), 7.70 (s, 1H), 7.43 (s, 1H), 7.12-7.04 (m, 1H), 7.04-6.95 (m, 1H), 5.68 (s, 1H), 3.75-3.65 (m, 4H), 3.48-3.38 (m, 4H). | 390.4 |
| 17 | (DMSO-$d_6$) δ 9.33 (s, 1H), 9.01 (s, 1H), 8.45-8.35 (m, 1H), 8.13-8.10 (m, 2H), 8.01 (s, 1H), 7.76 (s, 1H), 7.43 (s, 1H), 7.18-7.10 (m, 1H), 6.85-6.75 (m, 1H), 5.64 (s, 1H), 3.72-3.70 (m, 4H), 3.50-3.49 (m, 4H), 2.26 (s, 3H). | 403.2 |
| 18 | (DMSO-$d_6$) δ 9.23 (s, 1H), 9.05 (s, 1H), 8.40-8.30 (m, 1H), 8.13-8.04 (m, 3H), 7.78-7.72 (m, 1H), 7.52 (dd, J = 2.2, 8.6 Hz, 1H), 7.40 (s, 1H), 7.20-7.10 (m, 1H), 5.61 (s, 1H), 3.70-3.69 (m, 4H), 3.48-3.47 (m, 4H), 2.23 (s, 3H). | 403.3 |
| 19 | (DMSO-$d_6$) δ 9.37 (br. s, 1H), 9.30 (br. s, 1H), 8.48-8.42 (m, 1H), 8.42-8.36 (m, 1H), 8.20-8.10 (m, 1H), 7.96-7.91 (m, 1H), 7.87-7.82 (m, 1H), 7.81-7.75 (m, 1H), 7.50-7.44 (m, 1H), 7.10 (dd, J = 1.5, 7.3 Hz, 1H), 5.64 (s, 1H), 3.75-3.70 (m, 7H), 3.50-3.49 (m, 4H). | 417.2 (M - H) |
| 20 | (DMSO-$d_6$) δ 9.19 (s, 1H), 9.12 (s, 1H), 8.32-8.27 (m, 2H), 8.17-8.10 (m, 1H), 7.73-7.68 (m, 2H), 7.38 (s, 1H), 7.28-7.20 (m, 1H), 6.96 (dd, J = 2.0, 7.3 Hz, 1H), 5.58 (s, 1H), 3.49-3.47 (m, 4H), 3.71-3.64 (m, 4H). | 407.3 |
| 21 | (DMSO-$d_6$) δ 9.68 (br. s, 1H), 9.38 (br. s, 1H), 8.38-8.31 (m, 2H), 8.08-8.00 (m, 2H), 7.85-7.70 (m, 1H), 7.50-7.35 (m, 1H), 7.25-7.10 (m, 1H), 6.95-6.75 (m, 1H), 5.69 (s, 1H), 3.75-3.61 (m, 4H), 3.50-3.46 (m, 4H). | 407.2 |
| 22 | (DMSO-$d_6$) δ 10.03 (s, 1H), 9.50 (br. s, 1H), 8.78 (s, 1H), 8.52-8.45 (m, 1H), 8.45-8.38 (m, 1H), 8.19 (s, 1H), 8.16-8.12 (m, 1H), 7.80 (s, 1H), 7.49 (s, 1H), 7.30-7.20 (m, 1H), 5.73 (s, 1H), 3.72-3.50 (m, 8H). | 390.3 |
| 23 | (DMSO-$d_6$) δ 9.20 (s, 1H), 8.98 (s, 1H), 8.37-8.30 (m, 1H), 8.20-8.12 (m, 1H), 7.93-7.88 (m, 1H), 7.78-7.73 (m, 1H), 7.73-7.70 (m, 1H), 7.38 (d, J = 1.2 Hz, 1H), 7.13-7.07 (m, 1H), 6.98 (dd, J = 2.0, 7.2 Hz, 1H), 5.57 (s, 1H), 3.92 (s, 3H), 3.69-3.67 (m, 4H), 3.45-3.44 (m, 4H). | 419.2 |

TABLE 2-4

| | | |
|---|---|---|
| 24 | (DMSO-$d_6$) δ 11.22 (s, 1H), 9.16 (br. s, 1H), 8.60 (br. s, 1H), 8.40-8.30 (m, 1H), 7.79-7.65 (m, 4H), 7.39 (s, 1H), 7.06-7.01 (m, 1H), 6.38-6.30 (m, 1H), 5.51 (s, 1H), 3.72-3.66 (m, 4H), 3.42-3.38 (m, 4H). | 403.1 (M - H) |
| 25 | (DMSO-$d_6$) δ 9.23 (s, 1H), 8.99 (s, 1H), 8.40-8.32 (m, 1H), 8.16-8.11 (m, 1H), 8.11-8.05 (m, 1H), 8.05-8.00 (m, 1H), 7.73 (s, 1H), 7.39 (s, 1H), 7.07 (dd, J = 2.0, 7.3 Hz, 1H), 6.82-6.72 (m, 1H), 5.63 (s, 1H), 3.53-3.51 (m, 4H), 2.41-2.36 (m, 4H), 2.26 (s, 3H), 2.22 (s, 3H). | 416.1 |
| 26 | (DMSO-$d_6$) δ 9.14 (s, 1H), 8.96 (s, 1H), 8.38-8.30 (m, 1H), 8.11-8.05 (m, 3H), 7.72 (s, 1H), 7.58-7.50 (m, 1H), 7.39 (br. s, 1H), 7.18-7.10 (m, 1H), 5.61 (s, 1H), 3.54-3.48 (m, 4H), 2.23 (s, 3H), 1.64-1.54 (m, 6H). | 399.2 (M - H) |
| 27 | (DMSO-$d_6$) δ 9.19 (br. s, 1H), 9.03 (br. s, 1H), 8.40-8.30 (m, 1H), 8.20-7.95 (m, 3H), 7.78-7.70 (m, 1H), 7.58-7.48 (m, 1H), 7.45-7.35 (m, 1H), 7.18-7.10 (m, 1H), 5.61 (s, 1H), 3.55-3.45 (m, 4H), 2.39-2.32 (m, 4H), 2.27 (s, 3H), 2.20 (s, 3H). | 416.1 |
| 28 | (DMSO-$d_6$) δ 9.15 (s, 1H), 8.97 (s, 1H), 8.38-8.30 (m, 1H), 8.03-7.99 (m, 2H), 7.78-7.70 (m, 1H), 7.65-7.52 (m, 1H), 7.39 (s, 1H), 7.16 (dd, J = 2.0, 7.3 Hz, 1H), 6.85-6.75 (m, 1H), 5.62 (s, 1H), 3.58-3.53 (m, 4H), 2.39 (s, 3H), 1.64-1.55 (m, 6H). | 401.2 |
| 29 | (DMSO-$d_6$) δ 9.56 (s, 1H), 9.45 (s, 1H), 8.42-8.33 (m, 1H), 8.15-8.08 (m, 1H), 8.06-7.98 (m, 1H), 7.80-7.72 (m, 1H), 7.68-7.58 (m, 1H), 7.46-7.38 (m, 1H), 7.17 (dd, J = 2.0, 7.3 Hz, 1H), 6.88-6.80 (m, 1H), 5.67 (s, 1H), 4.33 (q, J = 6.8 Hz, 2H), 2.41 (s, 3H), 1.34 (t, J = 7.1 Hz, 3H). | 362.2 |
| 30 | (DMSO-$d_6$) δ 9.22 (s, 1H), 8.88 (s, 1H), 8.38-8.31 (m, 1H), 8.06-8.01 (m, 1H), 7.91-7.84 (m, 1H), 7.81-7.71 (m, 1H), 7.42-7.37 (m, 1H), 7.16-7.09 (m, 1H), 6.69-6.62 (m, 1H), 5.62 (s, 1H), 3.56-3.48 (m, 4H), 2.44-2.37 (m, 4H), 2.34 (s, 3H), 2.26-2.20 (m, 6H). | 430.1 |

TABLE 2-5

| | | |
|---|---|---|
| 31 | (DMSO-$d_6$) δ 9.19 (s, 1H), 8.89 (s, 1H), 8.37-8.31 (m, 1H), 8.07-8.00 (m, 1H), 7.92-7.87 (m, 1H), 7.75-7.70 (m, 1H), 7.41-7.36 (m, 1H), 7.17-7.10 (m, 1H), 6.67-6.62 (m, 1H), 5.60 (s, 1H), 4.17-4.09 (m, 1H), 4.03-3.98 (m, 1H), 2.98 (d, J = 11.2 Hz, 2H), 2.89-2.78 (m, 1H), 2.76-2.68 (m, 2H), 2.34 (s, 3H), 2.24 (s, 3H), 1.05 (d, J = 6.2 Hz, 3H). | 430.2 |
| 32 | (DMSO-$d_6$) δ 9.34 (s, 1H), 8.79 (s, 1H), 8.42-8.36 (m, 1H), 8.13-8.08 (m, 1H), 7.94-7.87 (m, 1H), 7.82-7.77 (m, 1H), 7.51-7.46 (m, 1H), 7.25 (dd, J = 7.3, 2.2 Hz, 1H), 6.67-6.62 (m, 1H), 5.65 (s, 1H), 3.59-3.52 (m, 4H), 2.35 (s, 3H), 2.23 (s, 3H), 1.70-1.51 (m, 6H). | 415.2 |
| 33 | (DMSO-$d_6$) δ 9.46 (s, 1H), 9.35 (s, 1H), 8.41-8.35 (m, 1H), 8.11-8.05 (m, 1H), 7.91-7.86 (m, 1H), 7.79-7.74 (m, 1H), 7.46-7.40 (m, 1H), 7.16 (dd, J = 7.3, 2.2 Hz, 1H), 6.71-6.66 (m, 1H), 5.68 (s, 1H), 4.35 (q, J = 7.0 Hz, 2H), 2.36 (s, 3H), 2.24 (s, 3H), 1.35 (t, J = 7.0 Hz, 3H). | 376.2 |
| 34 | (DMSO-$d_6$) δ 9.18 (br. s, 1H), 8.91 (s, 1H), 8.38-8.31 (m, 1H), 8.12-8.05 (m, 3H), 7.73 (s, 1H), 7.39 (s, 1H), 7.14-7.05 (m, 1H), 6.80-6.75 (m, 1H), 5.63 (s, 1H), 3.62-3.56 (m, 4H), 2.25 (s, 3H), 1.70-1.56 (m, 6H). | 401.2 |
| 35 | (DMSO-$d_6$) δ 9.21 (br. s, 1H), 9.00 (br. s, 1H), 8.42-8.35 (m, 1H), 8.15-8.11 (m, 1H), 8.11-8.06 (m, 1H), 8.06-8.00 (m, 1H), 7.76-7.70 (m, 1H), 7.43-7.37 (m, 1H), 7.15-7.05 (m, 1H) 6.82-6.75 (m, 1H), 5.63 (s, 1H), 4.03-3.96 (m, 2H), 3.17-3.16 (m, 1H), 3.03-2.99 (m, 2H), 2.91-2.80 (m, 2H), 2.27 (s, 3H), 2.22 (s, 3H), 1.07 (d, J = 5.9 Hz, 3H). | 430.2 |

TABLE 2-5-continued

| | | |
|---|---|---|
| 36 | (DMSO-d$_6$) δ 9.50-9.40 (m, 2H), 8.42-8.32 (m, 1H), 8.18-8.14 (m, 2H), 8.05-8.00 (m, 1H), 7.75 (s, 1H), 7.41 (s, 1H), 7.09 (dd, J = 2.0, 7.3 Hz, 1H), 6.85-6.79 (m, 1H), 5.68 (s, 1H), 4.35 (q, J = 7.0 Hz, 2H), 2.28 (s, 3H), 1.34 (t, J = 7.1 Hz, 3H). | 362.2 |

TABLE 2-6

| | | |
|---|---|---|
| 37 | (DMSO-d$_6$) δ 9.18 (s, 1H), 8.99 (s, 1H), 8.38-8.31 (m, 1H), 8.14-8.09 (m, 1H), 8.09-8.02 (m, 2H), 7.75-7.70 (m, 1H), 7.53 (dd, J = 8.7, 2.4 Hz, 1H), 7.40 (s, 1H), 7.14 (dd, J = 7.5, 2.1 Hz, 1H), 5.62 (s, 1H), 4.00 (dd, J = 25.9, 12.9 Hz, 2H), 3.07-2.96 (m, 1H), 2.80 (dd, J = 8.6, 5.7 Hz, 1H), 2.67-2.59 (m, 1H), 2.23 (d, J = 8.3 Hz, 6H), 2.19-2.02 (m, 2H), 1.06 (d, J = 6.1 Hz, 3H). | 430.2 |
| 38 | (DMSO-d$_6$) δ 9.55-9.47 (br. s, 1H), 9.47-9.39 (br. s, 1H), 8.45-8.32 (m, 1H), 8.14 (d, J = 10.3 Hz, 2H), 8.06 (d, J = 8.3 Hz, 1H), 7.75 (s, 1H), 7.57-7.55 (m, 1H), 7.42 (s, 1H), 7.20-7.10 (m, 1H), 5.66 (s, 1H), 4.33 (q, J = 6.8 Hz, 2H), 2.24 (s, 3H), 1.33 (t, J = 7.1 Hz, 3H). | 362.2 |
| 39 | (DMSO-d$_6$) δ 9.19 (s, 1H), 9.00 (s, 1H), 8.38-8.30 (m, 1H), 8.07-8.01 (m, 1H), 8.01-7.95 (m, 1H), 7.72 (s, 1H), 7.65-7.55 (m, 1H), 7.39 (d, J = 1.5 Hz, 1H), 7.16 (dd, J = 2.2, 7.6 Hz, 1H), 6.85-6.75 (m, 1H), 5.62 (s, 1H), 3.55-3.48 (m, 4H), 2.42-2.38 (m, 7H), 2.22 (s, 3H). | 414.3 (M − H) |
| 40 | (DMSO-d$_6$) δ 9.19 (s, 1H), 8.99 (s, 1H), 8.39-8.30 (m, 1H), 8.08-8.01 (m, 1H), 8.01-7.94 (m, 1H), 7.73 (s, 1H), 7.65-7.55 (m, 1H), 7.40 (s, 1H), 7.17-7.16 (m, 1H), 6.85-6.75 (m, 1H), 5.62 (s, 1H), 4.05-3.94 (m, 2H), 3.09-2.95 (m, 1H), 2.82-2.80 (m, 1H), 2.66-2.59 (m, 1H), 2.39 (s, 3H), 2.21 (s, 3H), 2.16-2.06 (m, 2H), 1.05 (d, J = 6.4 Hz, 3H). | 430.2 |
| 41 | (DMSO-d$_6$) δ 9.98 (s, 1H), 9.90 (s, 1H), 8.51-8.47 (m, 1H), 8.47-8.39 (m, 1H), 8.28-8.20 (m, 1H), 8.02 (d, J = 8.3 Hz, 1H), 7.87-7.82 (m, 1H), 7.82-7.78 (m, 1H), 7.75-7.65 (m, 1H), 7.46 (s, 1H), 7.27-7.20 (m, 1H), 7.17 (s, 1H), 6.90 (d, J = 7.3 Hz, 1H), 6.48 (s, 1H), 2.44 (s, 3H). | 384.1 |
| 42 | (DMSO-d$_6$) δ 9.95 (s, 1H), 9.91 (s, 1H), 8.50-8.46 (m, 1H), 8.46-8.41 (m, 1H), 8.33-8.26 (m, 1H), 8.23 (d, J = 4.9 Hz, 11), 7.95 (s, 1H), 7.87-7.82 (m, 1H), 7.82-7.78 (m, 1H), 7.46 (s, 1H), 7.21-7.16 (m, 1H), 7.16-7.10 (m, 1H), 6.91-6.84 (m, 1H), 6.49 (s, 1H), 2.30 (s, 3H). | 384.2 |

TABLE 2-7

| | | |
|---|---|---|
| 43 | (DMSO-d$_6$) δ 9.96 (s, 1H), 9.90 (s, 1H), 8.52-8.46 (m, 1H), 8.46-8.44 (m, 1H), 8.33-8.27 (m, 1H), 8.21-8.20 (m, 1H), 8.04 (d, J = 8.3 Hz, 1H), 7.88-7.78 (m, 2H), 7.63 (dd, J = 2.2, 8.6 Hz, 1H), 7.50-7.43 (m, 1H), 7.21-7.17 (m, 2H), 6.47 (s, 1H), 2.27 (s, 3H). | 384.1 |
| 44 | (DMSO-d$_6$) δ 9.06 (br. s, 1H), 8.66 (br. s, 1H), 8.41-8.30 (m, 1H), 8.25 (d, J = 8.3 Hz, 1H), 8.08 (s, 1H), 7.95 (br. s, 1H), 7.72 (br. s, 1H), 7.49 (dd, J = 2.0, 8.8 Hz, 1H), 7.40 (br. s, 1H), 7.13 (d, J = 6.8 Hz, 1H), 6.33 (br. s, 2H), 5.49 (s, 1H), 2.23 (s, 3H). | 333.2 |
| 45 | (DMSO-d$_6$) δ 9.19 (s, 1H), 8.89 (s, 1H), 8.37-8.30 (m, 1H), 8.06-8.01 (m, 1H), 7.91-7.86 (m, 1H), 7.75-7.70 (m, 1H), 7.41-7.36 (m, 1H), 7.13 (dd, J = 7.4, 2.2 Hz, 1H), 6.67-6.62 (m, 1H), 5.62 (s, 1H), 4.12-3.94 (m, 2H), 3.08-2.97 (m, 1H), 2.86-2.77 (m, 1H), 2.67-2.59 (m, 1H), 2.35 (s, 3H), 2.24 (s, 3H), 2.22 (s, 3H), 2.08-2.02 (m, 2H), 1.05 (dd, J = 8.1, 6.4 Hz, 3H). | 444.2 |
| 46 | (DMSO-d$_6$) δ 9.95 (s, 1H), 9.80 (s, 1H), 8.48-8.46 (m, 1H), 8.45-8.41 (m, 1H), 8.21-8.16 (m, 1H), 7.86-7.78 (m, 3H), 7.48-7.43 (m, 1H), 7.21-7.14 (m, 2H), 6.77-6.72 (m, 1H), 6.50 (s, 1H), 2.39 (s, 3H), 2.28 (s, 3H). | 398.1 |
| 47 | (DMSO-d$_6$) δ 10.05 (s, 1H), 9.31 (s, 1H), 8.60-8.57 (m, 1H), 8.56-8.53 (m, 1H), 8.37-8.29 (m, 1H), 8.18-8.12 (m, 1H), 7.77-7.71 (m, 1H), 7.43-7.38 (m, 1H), 7.26-7.20 (m, 1H), 7.16 (dd, J = 7.4, 2.2 Hz, 1H), 5.68 (s, 1H), 3.75-3.68 (m, 4H), 3.53-3.46 (m, 4H). | 457.1 |
| 48 | (DMSO-d$_6$) δ 9.25 (s, 1H), 9.18 (s, 1H), 8.38-8.29 (m, 1H), 8.12-8.04 (m, 2H), 7.83 (d, J = 2.3 Hz, 1H), 7.76-7.70 (m, 1H), 7.42-7.37 (m, 1H), 7.20-7.13 (m, 1H), 6.53 (dd, J = 5.7, 2.4 Hz, 1H), 5.64 (s, 1H), 3.74 (s, 3H), 3.73-3.67 (m, 4H), 3.53-3.46 (m, 4H). | 419.0 |

TABLE 2-8

| | | |
|---|---|---|
| 49 | (DMSO-d$_6$) δ 10.30 (s, 1H), 9.40 (s, 1H), 9.08-9.03 (m, 1H), 8.65-8.59 (m, 1H), 8.39-8.33 (m, 1H), 8.23-8.18 (m, 1H), 7.78-7.73 (m, 1H), 7.65-7.58 (m, 1H), 7.45-7.40 (m, 1H), 7.18 (dd, J = 7.4, 2.2 Hz, 1H), 5.71 (s, 1H), 3.78-3.70 (m, 4H), 3.59-3.51 (m, 4H). | 434.0 |
| 50 | (DMSO-d$_6$) δ 9.08 (s, 1H), 8.57 (s, 1H), 8.39-8.30 (m, 1H), 8.20-8.11 (m, 1H), 8.11-8.05 (m, 1H), 8.20-7.92 (m, 1H), 7.72 (s, 1H), 7.38 (s, 1H), 7.12-7.02 (m, 1H), 6.70-6.60 (m, 1H), 6.34 (br. s, 2H), 5.49 (s, 1H), 2.27 (s, 3H). | 333.2 |
| 51 | (DMSO-d$_6$) δ 9.06 (s, 1H), 8.58 (s, 1H), 8.37-8.30 (m, 1H), 8.15-7.95 (m, 2H), 7.74-7.69 (m, 1H), 7.61-7.53 (m, 1H), 7.41-7.35 (m, 1H), 6.95 (dd, J = 7.4, 2.2 Hz, 1H), 6.41-6.33 (m, 1H), 5.52 (s, 1H), 3.85 (q, J = 7.1 Hz, 2H), 3.54-3.46 (m, 4H), 1.71-1.46 (m, 6H), 1.15 (t, J = 7.1 Hz, 3H). | 431.2 |
| 52 | (500 MHz, DMSO-d$_6$) δ 9.10 (s, 1H), 8.62 (s, 1H), 8.37-8.31 (m, 1H), 8.17-7.93 (m, 2H), 7.74-7.70 (m, 1H), 7.61-7.54 (m, 1H), 7.41-7.37 (m, 1H), 6.99-6.93 (m, 1H), 6.40-6.34 (m, 1H), 5.53 (s, 1H), 3.96-3.92 (m, 2H), 3.86 (q, J = 7.2 Hz, 2H), 3.03-2.94 (m, 1H), 2.83-2.77 (m, 1H), 2.63-2.57 (m, 1H), 2.22 (s, 3H), 2.16-2.09 (m, 1H), 2.07-2.03 (m, 1H), 1.17-1.13 (m, 3H), 1.04 (d, J = 6.2 Hz, 3H). | 460.4 |
| 53 | (DMSO-d$_6$) δ 9.36 (s, 1H), 9.16 (s, 1H), 8.42-8.30 (m, 1H), 8.15-8.03 (m, 1H), 7.78 (s, 1H), 7.66-7.54 (m, 1H), 7.46 (s, 1H), 7.33-7.21 (m, 1H), 5.61 (s, 1H), 3.72-3.71 (m, 4H), 3.50-3.48 (m, 4H), 2.35 (d, J = 2.8 Hz, 3H), 2.07-2.03 (m, 1H), 1.01-1.00 (m, 2H), 0.71-0.61 (m, 2H). | 461.2 |

TABLE 2-9

| | | |
|---|---|---|
| 54 | (500 MHz, DMSO-d$_6$) δ 9.05 (s, 1H), 8.64 (s, 1H), 8.33 (dd, J = 7.4, 0.8 Hz, 1H), 8.23-8.15 (m, 1H), 7.95-7.90 (m, 1H), 7.74-7.70 (m, 1H), 7.59-7.51 (m, 1H), 7.41-7.36 (m, 1H), 7.18-7.12 (m, 1H), 6.81-6.75 (m, 1H), 6.35 (s, 2H), 5.49 (s, 1H), 2.38 (s, 3H). | 333.0 |
| 55 | (500 MHz, DMSO-d$_6$) δ 9.11 (s, 1H), 8.60 (s, 1H), 8.37-8.32 (m, 1H), 8.23-7.98 (m, 2H), 7.75-7.71 (m, 1H), 7.60 (dd, J = 9.7, 2.9 Hz, 1H), 7.43-7.39 (m, 1H), 7.03-6.98 (m, 1H), 6.41-6.35 (m, 1H), 5.53 (s, 1H), 5.14-5.07 (m, 1H), 3.55-3.48 (m, 4H), 1.69-1.47 (m, 6H), 1.25 (d, J = 6.7 Hz, 6H). | 445.3 |
| 56 | (DMSO-d$_6$) δ 9.15-9.07 (m, 1H), 8.68-8.57 (m, 1H), 8.38-8.28 (m, 1H), 8.05-7.94 (m, 1H), 7.76-7.68 (m, 1H), 7.66-7.57 (m, 1H), 7.44-7.33 (m, 1H), 7.02-6.90 (m, 1H), 6.43-6.33 (m, 1H), 5.53 (s, 1H), 5.16-5.00 (m, 1H), 4.05-3.86 (m, 2H), 3.03-2.91 (m, 1H), 2.85-2.75 (m, 1H), 2.65-2.56 (m, 1H), 2.21 (s, 3H), 2.19-1.94 (m, 2H), 1.32-1.18 (m, 6H), 1.04 (d, J = 6.1 Hz, 3H). | 474.7 |
| 57 | (DMSO-d$_6$) δ 9.33 (s, 1H), 8.96 (s, 1H), 8.39-8.32 (m, 1H), 8.01-7.96 (m, 2H), 7.77-7.71 (m, 1H), 7.68-7.60 (m, 1H), 7.43-7.38 (m, 1H), 6.99-6.92 (m, 1H), 6.44-6.36 (m, 1H), 5.56 (s, 1H), 5.10-5.05 (m, 1H), 4.30 (q, J = 7.0 Hz, 2H), 1.30 (t, J = 7.0 Hz, 3H), 1.28-1.19 (m, 6H). | 406.4 |

TABLE 2-9-continued

| | | |
|---|---|---|
| 58 | (500 MHz, DMSO-$d_6$) δ 9.06 (s, 1H), 8.45 (s, 1H), 8.36-8.31 (m, 1H), 8.02-7.98 (m, 1H), 7.95-7.90 (m, 1H), 7.74-7.70 (m, 1H), 7.40-7.35 (m, 1H), 7.10 (dd, J = 7.4, 2.2 Hz, 1H), 6.64-6.60 (m, 1H), 6.34 (s, 2H), 5.48 (s, 1H), 2.33 (s, 3H), 2.23 (s, 3H). | 347.2 |
| 59 | (Methanol-$d_4$) δ 8.33-8.26 (m, 1H), 8.19-8.14 (m, 1H), 8.13-8.08 (m, 1H), 7.76-7.67 (m, 2H), 7.48 (s, 1H), 7.18-7.11 (m, 1H), 6.60-6.53 (m, 1H), 5.59 (s, 1H), 5.29-5.19 (m, 1H), 3.66-3.59 (m, 4H), 2.62-2.54 (m, 4H), 2.39 (s, 3H), 1.36 (d, J = 6.7 Hz, 6H). | 460.1 |

TABLE 2-10

| | | |
|---|---|---|
| 60 | (500 MHz, DMSO-$d_6$) δ 9.20 (s, 1H), 9.12 (s, 1H), 8.76-8.72 (m, 1H), 8.36 (dd, J = 7.3, 0.9 Hz, 1H), 8.11 (s, 1H), 8.02 (dd, J = 8.4, 2.7 Hz, 1H), 7.75-7.71 (m, 1H), 7.42-7.38 (m, 1H), 7.14 (d, J = 8.4 Hz, 1H), 7.01 (dd, J = 7.4, 2.2 Hz, 1H), 5.58 (s, 1H), 3.73-3.67 (m, 4H), 3.49-3.43 (m, 4H), 2.39 (s, 3H). | 403.1 |
| 61 | (DMSO-$d_6$) δ 9.17 (s, 1H), 8.94 (s, 1H), 8.40-8.37 (m, 1H), 8.36-8.32 (m, 1H), 8.12-8.05 (m, 1H), 8.02 (dd, J = 8.9, 2.7 Hz, 1H), 7.72 (s, 1H), 7.39 (s, 1H), 6.99 (dd, J = 7.4, 2.0 Hz, 1H), 6.75 (d, J = 8.9 Hz, 1H), 5.56 (s, 1H), 4.28 (t, J = 6.0 Hz, 2H), 3.73-3.65 (m, 4H), 3.48-3.41 (m, 4H), 2.60 (t, J = 5.9 Hz, 2H), 2.20 (s, 6H). | 476.1 |
| 62 | (DMSO-$d_6$) δ 9.13 (s, 1H), 8.91 (s, 1H), 8.39-8.35 (m, 1H), 8.35-8.28 (m, 1H), 8.08-8.03 (m, 1H), 7.99 (dd, J = 8.9, 2.7 Hz, 1H), 7.72-7.67 (m, 1H), 7.40-7.34 (m, 1H), 6.97 (dd, J = 7.4, 2.2 Hz, 1H), 6.76-6.68 (m, 1H), 5.53 (s, 1H), 4.18 (t, J = 6.6 Hz, 2H), 3.71-3.63 (m, 4H), 3.46-3.37 (m, 4H), 1.72-1.60 (m, 2H), 1.47-1.33 (m, 2H), 0.91 (t, J = 7.4 Hz, 3H). | 461.3 |
| 63 | (DMSO-$d_6$) δ 9.14 (s, 1H), 8.90 (s, 1H), 8.36-8.32 (m, 1H), 8.32-8.30 (m, 1H), 8.09-7.99 (m, 2H), 7.74-7.69 (m, 1H), 7.42-7.36 (m, 1H), 7.00 (dd, J = 7.4, 2.1 Hz, 1H), 6.68-6.61 (m, 1H), 5.55 (s, 1H), 3.72-3.65 (m, 4H), 3.48-3.41 (m, 4H), 1.50 (s, 9H). | 461.4 |
| 64 | (DMSO-$d_6$) δ 9.14 (s, 1H), 8.91 (s, 1H), 8.42-8.36 (m, 1H), 8.36-8.29 (m, 1H), 8.07 (s, 1H), 8.01 (dd, J = 8.9, 2.8 Hz, 1H), 7.75-7.69 (m, 1H), 7.42-7.37 (m, 1H), 7.00 (dd, J = 7.4, 2.2 Hz, 1H), 6.79-6.72 (m, 1H), 5.55 (s, 1H), 3.98 (d, J = 6.7 Hz, 2H), 3.73-3.65 (m, 4H), 3.48-3.41 (m, 4H), 2.06-1.97 (m, 1H), 0.97 (d, J = 6.7 Hz, 6H). | 461.3 |
| 65 | (DMSO-$d_6$) δ 9.14 (s, 1H), 8.92 (s, 1H), 8.44-8.37 (m, 1H), 8.34 (dd, J = 7.5, 0.8 Hz, 1H), 8.08 (s, 1H), 8.01 (dd, J = 8.9, 2.8 Hz, 1H), 7.74-7.69 (m, 1H), 7.42-7.36 (m, 1H), 7.00 (dd, J = 7.4, 2.2 Hz, 1H), 6.77 (d, J = 8.9 Hz, 1H), 5.55 (s, 1H), 3.90 (s, 2H), 3.73-3.66 (m, 4H), 3.48-3.41 (m, 4H), 0.99 (s, 9H). | 475.3 |

TABLE 2-11

| | | |
|---|---|---|
| 66 | (DMSO-$d_6$) δ 9.16 (s, 1H), 8.94 (s, 1H), 8.43-8.36 (m, 1H), 8.36-8.30 (m, 1H), 8.13-8.06 (m, 1H), 8.03 (dd, J = 8.9, 2.7 Hz, 1H), 7.74-7.69 (m, 1H), 7.42-7.37 (m, 1H), 6.99 (dd, J = 7.3, 2.1 Hz, 1H), 6.77 (d, J = 8.8 Hz, 1H), 5.55 (s, 1H), 4.33 (t, J = 4.7 Hz, 2H), 3.74-3.67 (m, 4H), 3.65 (t, J = 4.8 Hz, 2H), 3.48-3.39 (m, 4H), 3.30 (s, 3H). | 463.4 |
| 67 | (DMSO-$d_6$) δ 9.24 (s, 1H), 9.18 (s, 1H), 8.33 (dd, J = 7.7, 1.0 Hz, 1H), 8.19-8.17 (m, 1H), 8.17 (dd, J = 1.8, 0.7 Hz, 1H), 8.13-8.11 (m, 1H), 7.77-7.69 (m, 1H), 7.43-7.35 (m, 1H), 7.17 (dd, J = 7.4, 2.2 Hz, 1H), 6.97 (dd, J = 5.3, 1.8 Hz, 1H), 5.62 (s, 1H), 3.74-3.67 (m, 4H), 3.57-3.49 (m, 4H), 1.23 (s, 9H). | 445.1 |

TABLE 2-11-continued

| | | |
|---|---|---|
| 68 | (DMSO-$d_6$) δ 9.26 (s, 1H), 9.10 (s, 1H), 8.35 (dd, J = 7.3, 0.8 Hz, 1H), 8.15 (dd, J = 5.1, 0.7 Hz, 1H), 8.07 (s, 2H), 7.76-7.71 (m, 1H), 7.40 (d, J = 1.2 Hz, 1H), 7.12 (dd, J = 7.4, 2.2 Hz, 1H), 6.80 (dd, J = 5.1, 1.5 Hz, 1H), 5.63 (s, 1H), 3.75-3.65 (m, 4H), 3.58-3.43 (m, 4H), 2.58 (q, J = 7.6 Hz, 2H), 1.10 (t, J = 7.6 Hz, 3H). | 417.1 |
| 69 | (DMSO-$d_6$) δ 9.16 (s, 1H), 8.95 (s, 1H), 8.43-8.37 (m, 1H), 8.37-8.31 (m, 1H), 8.09 (s, 1H), 8.01 (dd, J = 8.9, 2.8 Hz, 1H), 7.75-7.70 (m, 1H), 7.42-7.36 (m, 1H), 6.99 (dd, J = 7.5, 2.2 Hz, 1H), 6.75 (d, J = 8.9 Hz, 1H), 5.55 (s, 1H), 4.15 (t, J = 6.7 Hz, 2H), 3.73-3.66 (m, 4H), 3.48-3.41 (m, 4H), 1.72 (h, J = 7.2 Hz, 2H), 0.97 (t, J = 7.4 Hz, 3H). | 447.3 |
| 70 | (DMSO-$d_6$) δ 9.25 (s, 1H), 9.16 (s, 1H), 8.34 (dd, J = 7.3, 0.8 Hz, 1H), 8.16 (dd, J = 5.2, 0.7 Hz, 1H), 8.09 (dd, J = 2.0, 0.9 Hz, 1H), 8.08-8.06 (m, 1H), 7.77-7.68 (m, 1H), 7.41-7.36 (m, 1H), 7.15 (dd, J = 7.4, 2.2 Hz, 1H), 6.83 (dd, J = 5.3, 1.5 Hz, 1H), 5.63 (s, 1H), 3.71 (dd, J = 5.9, 3.8 Hz, 4H), 3.56-3.46 (m, 4H), 2.89-2.74 (m, 1H), 1.16 (d, J = 6.9 Hz, 6H). | 431.0 |
| 71 | (DMSO-$d_6$) δ 9.16 (s, 1H), 9.01 (s, 1H), 8.34 (dd, J = 7.4, 0.8 Hz, 1H), 8.14 (dd, J = 5.1, 0.7 Hz, 1H), 8.10 (dd, J = 1.6, 0.8 Hz, 1H), 8.08-8.05 (m, 1H), 7.76-7.69 (m, 1H), 7.43-7.35 (m, 1H), 7.13 (dd, J = 7.4, 2.2 Hz, 1H), 6.79 (dd, J = 5.1, 1.5 Hz, 1H), 5.63 (s, 1H), 3.61-3.51 (m, 4H), 2.58 (q, J = 7.6 Hz, 2H), 1.70-1.51 (m, 6H), 1.13 (t, J = 7.6 Hz, 3H). | 415.1 |

TABLE 2-12

| | | |
|---|---|---|
| 72 | (DMSO-$d_6$) δ 9.15 (s, 1H), 9.08 (s, 1H), 8.32 (dd, J = 7.4, 0.8 Hz, 1H), 8.23 (dd, J = 1.8, 0.8 Hz, 1H), 8.17 (dd, J = 5.3, 0.7 Hz, 1H), 8.13-8.07 (m, 1H), 7.75-7.69 (m, 1H), 7.41-7.34 (m, 1H), 7.18 (dd, J = 7.4, 2.2 Hz, 1H), 6.96 (dd, J = 5.4, 1.8 Hz, 1H), 5.62 (s, 1H), 3.64-3.53 (m, 4H), 1.71-1.51 (m, 6H), 1.25 (s, 9H). | 443.0 |
| 73 | (DMSO-$d_6$) δ 9.15 (s, 1H), 9.06 (s, 1H), 8.33 (dd, J = 7.4, 0.8 Hz, 1H), 8.15 (dd, J = 5.1, 0.7 Hz, 1H), 8.14-8.12 (m, 1H), 8.11-8.04 (m, 1H), 7.76-7.70 (m, 1H), 7.41-7.36 (m, 1H), 7.16 (dd, J = 7.4, 2.2 Hz, 1H), 6.82 (dd, J = 5.2, 1.5 Hz, 1H), 5.63 (s, 1H), 3.63-3.52 (m, 4H), 2.89-2.76 (m, 1H), 1.72-1.51 (m, 6H), 1.18 (d, J = 6.9 Hz, 6H). | 429.0 |
| 74 | (DMSO-$d_6$) δ 9.26 (s, 1H), 9.09 (s, 1H), 8.35 (dd, J = 7.4, 0.8 Hz, 1H), 8.14 (dd, J = 5.1, 0.7 Hz, 1H), 8.07 (dd, J = 1.9, 0.9 Hz, 1H), 8.05 (dd, J = 1.6, 0.8 Hz, 1H), 7.77-7.70 (m, 1H), 7.44-7.37 (m, 1H), 7.11 (dd, J = 7.4, 2.2 Hz, 1H), 6.78 (dd, J = 5.1, 1.5 Hz, 1H), 5.62 (s, 1H), 3.76-3.66 (m, 4H), 3.56-3.45 (m, 4H), 2.55-2.51 (m, 2H), 1.60-1.46 (m, 2H), 0.82 (t, J = 7.3 Hz, 3H). | 431.2 |
| 75 | (DMSO-$d_6$) δ 9.16 (s, 1H), 9.01 (s, 1H), 8.34 (dd, J = 7.4, 0.8 Hz, 1H), 8.13 (dd, J = 5.1, 0.7 Hz, 1H), 8.10 (dd, J = 1.7, 0.8 Hz, 1H), 8.08-8.06 (m, 1H), 7.77-7.69 (m, 1H), 7.44-7.35 (m, 1H), 7.12 (dd, J = 7.4, 2.2 Hz, 1H), 6.77 (dd, J = 5.1, 1.5 Hz, 1H), 5.63 (s, 1H), 3.61-3.52 (m, 4H), 2.55-2.52 (m, 2H), 1.73-1.48 (m, 8H), 0.83 (t, J = 7.3 Hz, 3H). | 429.2 |
| 76 | (DMSO-$d_6$) δ 9.15 (s, 1H), 8.69 (s, 1H), 8.34 (d, J = 7.3 Hz, 1H), 8.12-8.07 (m, 1H), 8.05-8.00 (m, 1H), 7.75-7.70 (m, 1H), 7.59 (dd, J = 9.6, 2.9 Hz, 1H), 7.39 (d, J = 1.2 Hz, 1H), 6.95 (dd, J = 7.5, 2.2 Hz, 1H), 6.42 (d, J = 9.6 Hz, 1H), 5.94-5.80 (m, 1H), 5.51 (s, 1H), 5.17-5.09 (m, 1H), 5.04-4.95 (m, 1H), 4.51 (d, J = 5.8 Hz, 2H), 3.72-3.64 (m, 4H), 3.46-3.38 (m, 4H). | 445.3 |
| 77 | (DMSO-$d_6$) δ 9.18 (s, 1H), 9.07 (s, 1H), 8.50-8.44 (m, 1H), 8.35 (d, J = 7.3 Hz, 1H), 8.11 (dd, J = 8.9, 2.7 Hz, 1H), 8.09-8.04 (m, 1H), 7.75-7.70 (m, 1H), 7.42-7.36 (m, 1H), 6.98 (dd, J = 7.3, 2.2 Hz, 1H), 6.93 (d, J = 8.9 Hz, 1H), 5.57 (s, 1H), 4.95 (q, J = 9.2 Hz, 2H), 3.70 (t, J = 5.1 Hz, 4H), 3.49-3.42 (m, 4H). | 487.3 |

TABLE 2-13

| | | |
|---|---|---|
| 78 | (DMSO-d$_6$) δ 9.22 (s, 2H), 8.58-8.52 (m, 1H), 8.39-8.32 (m, 1H), 8.22 (dd, J = 8.8, 2.8 Hz, 1H), 8.10-8.05 (m, 1H), 7.75-7.70 (m, 1H), 7.42-7.37 (m, 1H), 7.03 (d, J = 8.8 Hz, 1H), 6.97 (dd, J = 7.4, 2.2 Hz, 1H), 5.60 (s, 1H), 3.74-3.67 (m, 4H), 3.50-3.42 (m, 4H), 3.36 (s, 1H). | 455.3 |
| 79 | (DMSO-d$_6$) δ 9.11 (s, 1H), 9.05 (s, 1H), 8.80-8.73 (m, 1H), 8.35 (d, J = 7.3, 0.8 Hz, 1H), 8.12-8.06 (m, 1H), 8.03 (dd, J = 8.4, 2.7 Hz, 1H), 7.76-7.69 (m, 1H), 7.42-7.36 (m, 1H), 7.18-7.07 (m, 1H), 7.00 (dd, J = 7.4, 2.2 Hz, 1H), 5.58 (s, 1H), 3.57-3.48 (m, 4H), 2.39 (s, 3H), 1.71-1.49 (m, 6H). | 401.3 |
| 80 | (DMSO-d$_6$) δ 9.15 (s, 1H), 8.92 (s, 1H), 8.34 (dd, J = 5.0, 2.4 Hz, 2H), 8.09-7.99 (m, 2H), 7.74-7.69 (m, 1H), 7.42-7.36 (m, 1H), 7.03-6.95 (m, 1H), 6.71 (d, J = 8.9 Hz, 1H), 5.55 (s, 1H), 5.08 (p, J = 7.4 Hz, 1H), 3.73-3.65 (m, 4H), 3.48-3.40 (m, 4H), 2.44-2.32 (m, 2H), 2.10-1.95 (m, 2H), 1.83-1.56 (m, 2H). | 459.2 |
| 81 | (DMSO-d$_6$) δ 9.16 (s, 1H), 8.92 (s, 1H), 8.36-8.35 (m, 1H), 8.35-8.33 (m, 1H), 8.10-8.05 (m, 1H), 8.01 (dd, J = 8.9, 2.8 Hz, 1H), 7.75-7.69 (m, 1H), 7.42-7.36 (m, 1H), 6.99 (dd, J = 7.4, 2.2 Hz, 1H), 6.70 (d, J = 8.8 Hz, H), 5.55 (s, 1H), 4.96-4.85 (m, 1H), 3.73-3.65 (m, 4H), 3.48-3.40 (m, 4H), 2.00-1.91 (m, 2H), 1.77-1.69 (m, 2H), 1.63-1.13 (m, 6H). | 487.5 |
| 82 | (DMSO-d$_6$) δ 9.16 (s, 1H), 8.94 (s, 1H), 8.40-8.36 (m, 1H), 8.36-8.32 (m, 1H), 8.11-8.05 (m, 1H), 8.02 (dd, J = 8.9, 2.8 Hz, 1H), 7.74-7.69 (m, 1H), 7.41-7.36 (m, 1H), 6.97 (dd, J = 7.4, 2.2 Hz, 1H), 6.74 (d, J = 8.8 Hz, 1H), 5.55 (s, 1H), 5.15-5.06 (m, 1H), 3.91-3.81 (m, 2l), 3.73-3.65 (m, 4H), 3.54-3.41 (m, 6l), 2.04-1.96 (m, 2l), 1.68-1.54 (m, 2l). | 489.4 |
| 83 | (DMSO-d$_6$) δ 9.12 (s, 1H), 9.05 (s, 1H), 8.83-8.75 (m, 1H), 8.34 (d, J = 7.4, 0.8 Hz, 1H), 8.14-8.09 (m, 2H), 7.75-7.69 (m, 1H), 7.44-7.36 (m, 1H), 7.18-7.08 (m, 1H), 7.02 (d, J = 7.4, 2.2 Hz, 1H), 5.46 (s, 1H), 3.03 (s, 6H), 2.39 (s, 3H). | 360.9 |

TABLE 2-14

| | | |
|---|---|---|
| 84 | (DMSO-d$_6$) δ 9.18 (s, 1H), 8.79 (s, 1H), 8.33 (dd, J = 7.4, 0.8 Hz, 1H), 8.06-8.01 (m, 1H), 8.01-7.96 (m, 1H), 7.76-7.68 (m, 1H), 7.42-7.36 (m, 1H), 7.17 (dd, J = 7.4, 2.2 Hz, 1H), 6.67-6.61 (m, 1H), 5.50 (s, 1H), 3.05 (s, 6H), 2.34 (s, 3H), 2.24 (s, 3H). | 375.1 |
| 85 | (DMSO-d$_6$) δ 8.99 (s, 1H), 8.91 (s, 1H), 8.74 (dd, J = 2.7, 0.7 Hz, 1H), 8.34 (dd, J = 7.4, 0.8 Hz, 1H), 8.20 (dd, J = 8.4, 2.6 Hz, 1H), 8.00-7.93 (m, 1H), 7.77-7.68 (m, 1H), 7.42-7.34 (m, 1H), 7.13-7.07 (m, 1H), 7.02 (dd, J = 7.4, 2.2 Hz, 1H), 6.26 (s, 2H), 5.45 (s, 1H), 2.39 (s, 3H). | 332.9 |
| 86 | (DMSO-d$_6$) δ 9.46 (s, 1H), 9.42 (s, 1H), 8.37 (dd, J = 7.4, 0.8 Hz, 1H), 8.12-8.04 (m, 1H), 7.95-7.87 (m, 1H), 7.79-7.71 (m, 1H), 7.46-7.37 (m, 1H), 7.13 (dd, J = 7.4, 2.2 Hz, 1H), 6.74-6.64 (m, 1H), 5.70 (s, 1H), 3.89 (s, 3H), 2.37 (s, 3H), 2.25 (s, 3H). | 361.9 |
| 87 | (DMSO-d$_6$) δ 9.22 (s, 1H), 8.91 (s, 1H), 8.34 (dd, J = 7.4, 0.8 Hz, 1H), 8.04-8.00 (m, 1H), 7.94-7.87 (m, 1H), 7.75-7.71 (m, 1H), 7.46-7.41 (m, 1H), 7.41-7.38 (m, 1H), 7.19 (dd, J = 7.4, 2.2 Hz, 1H), 5.60 (s, 1H), 3.74-3.66 (m, 4H), 3.51-3.44 (m, 4H), 2.35 (s, 3H), 2.19 (s, 3H). | 417.2 |
| 88 | (DMSO-d$_6$) δ 9.13 (s, 1H), 8.79 (s, 1H), 8.35-8.32 (m, 1H), 8.03-7.99 (m, 1H), 7.95-7.88 (m, 1H), 7.75-7.71 (m, 1H), 7.47-7.40 (m, 1H), 7.40-7.37 (m, 1H), 7.18 (dd, J = 7.4, 2.2 Hz, 1H), 5.60 (s, 1H), 3.59-3.46 (m, 4H), 2.35 (s, 3H), 2.19 (s, 3H), 1.69-1.48 (m, 6H). | 415.0 |

TABLE 2-14-continued

| | | |
|---|---|---|
| 89 | (DMSO-d$_6$) δ 9.16 (s, 1H), 8.92 (s, 1H), 8.38-8.30 (m, 2H), 8.07 (s, 1H), 8.01 (dd, J = 8.8, 2.8 Hz, 1H), 7.74-7.69 (m, 1H), 7.41-7.34 (m, 1H), 6.98 (dd, J = 7.4, 2.1 Hz, 1H), 6.72 (d, J = 8.9 Hz, 1H), 5.55 (s, 1H), 4.95-4.84 (m, 1H), 3.73-3.65 (m, 4H), 3.48-3.37 (m, 4H), 2.68-2.58 (m, 2H), 2.22-2.09 (m, 5H), 2.04-1.87 (m, 2H), 1.64 (dtd, J = 12.9, 9.1, 3.7 Hz, 2H). | 502.4 |

TABLE 2-15

| | | |
|---|---|---|
| 90 | (DMSO-d$_6$) δ 9.19 (s, 1H), 9.14 (s, 1H), 8.46 (d, J = 2.8 Hz, 1H), 8.38-8.31 (m, H), 8.20 (dd, J = 8.8, 2.8 Hz, 1H), 8.12-8.07 (m, 1H), 7.72 (s, 1H), 7.44-7.35 (m, 3H), 7.20-7.13 (m, 1H), 7.13-7.07 (m, 2H), 6.98 (dd, J = 8.1, 2.6 Hz, 2H), 5.58 (s, 1H), 3.73-3.66 (m, 4H), 3.49-3.41 (m, 4H). | 481.4 |
| 91 | (DMSO-d$_6$) δ 9.18 (s, 1H), 8.97 (s, 1H), 8.45-8.40 (m, 1H), 8.39-8.31 (m, 1H), 8.10-8.02 (m, 1H), 7.75-7.70 (m, 1H), 7.49-7.27 (m, 6H), 7.01 (dd, J = 7.3, 2.1 Hz, 1H), 6.84 (d, J = 8.8 Hz, 1H), 5.56 (s, 1H), 5.31 (s, 2H), 3.73-3.66 (m, 4H), 3.49-3.41 (m, 4H). | 495.4 |
| 92 | (DMSO-d$_6$) δ 9.14 (s, 1H), 8.97 (s, 1H), 8.33 (dd, J = 7.4, 0.8 Hz, 1H), 8.22-8.18 (m, 1H), 8.15-8.12 (m, 1H), 8.10-8.06 (m, 1H), 7.75-7.69 (m, 1H), 7.41-7.36 (m, 1H), 7.17 (dd, J = 7.4, 2.2 Hz, 1H), 6.79 (dd, J = 5.1, 1.5 Hz, 1H), 5.52 (s, 1H), 3.90-3.42 (m, 4H), 2.58 (q, J = 7.6 Hz, 2H), 1.81-1.72 (m, 4H), 1.58-1.47 (m, 4H), 1.15 (t, J = 7.6 Hz, 3H). | 429.1 |
| 93 | (DMSO-d$_6$) δ 9.16 (s, 1H), 9.08 (s, 1H), 8.33 (dd, J = 7.3, 0.8 Hz, 1H), 8.09-8.03 (m, 2H), 7.91-7.85 (m, 1H), 7.75-7.70 (m, 1H), 7.41-7.36 (m, 1H), 7.17 (dd, J = 7.4, 2.2 Hz, 1H), 6.52 (dd, J = 5.8, 2.4 Hz, 1H), 5.64 (s, 1H), 3.76 (s, 3H), 3.60-3.53 (m, 4H), 1.70-1.50 (m, 6H). | 417.1 |
| 94 | (DMSO-d$_6$) δ 9.16 (s, 1H), 8.91 (s, 1H), 8.33 (dd, J = 7.4, 0.8 Hz, 1H), 8.30-8.28 (m, 1H), 8.16-8.10 (m, 1H), 8.09-8.04 (m, 1H), 7.75-7.69 (m, 1H), 7.41-7.36 (m, 1H), 7.18 (dd, J = 7.5, 2.2 Hz, 1H), 6.79 (dd, J = 5.1, 1.5 Hz, 1H), 5.37 (s, 1H), 3.47-3.42 (m, 4H), 2.59 (q, J = 7.6 Hz, 2H), 2.00-1.92 (m, 4H), 1.16 (t, J = 7.6 Hz, 3H). | 401.2 |

TABLE 2-16

| | | |
|---|---|---|
| 95 | (500 MHz, DMSO-d$_6$) δ 9.16 (s, 1H), 8.88 (s, 1H), 8.34 (dd, J = 7.4, 0.8 Hz, 1H), 8.06-8.04 (m, 1H), 8.03-8.00 (m, 1H), 7.75-7.70 (m, 1H), 7.65-7.58 (m, 1H), 7.42-7.36 (m, 1H), 7.15 (dd, J = 7.4, 2.2 Hz, 1H), 6.81 (d, J = 7.3 Hz, 1H), 5.63 (s, 1H), 3.57-3.51 (m, 4H), 2.66 (q, J = 7.6 Hz, 2H), 1.69-1.60 (m, 2H), 1.60-1.51 (m, 4H), 1.24 (t, J = 7.6 Hz, 3H). | 415.2 |
| 96 | (500 MHz, DMSO-d$_6$) δ 9.16 (s, 1H), 8.66 (s, 1H), 8.37-8.32 (m, 1H), 8.07-8.03 (m, 1H), 7.95 (dd, J = 8.4, 0.9 Hz, 1H), 7.75-7.70 (m, 1H), 7.58-7.51 (m, 1H), 7.39 (d, J = 1.3 Hz, 1H), 7.10 (dd, J = 7.4, 2.1 Hz, 1H), 6.83 (dd, J = 7.4, 0.9 Hz, 1H), 5.62 (s, 1H), 3.57-3.50 (m, 4H), 2.04-1.95 (m, 1H), 1.68-1.51 (m, 6H), 0.98-0.86 (m, 4H). | 427.2 |
| 97 | (DMSO-d$_6$) δ 9.17 (s, 1H), 9.04 (s, 1H), 8.34 (dd, J = 7.4, 0.8 Hz, 1H), 8.14 (d, J = 5.1, 0.7 Hz, 1H), 8.11-8.08 (m, 1H), 8.08-8.06 (m, 1H), 7.75-7.70 (m, 1H), 7.41-7.36 (m, 1H), 7.13 (dd, J = 7.4, 2.2 Hz, 1H), 6.80 (dd, J = 5.1, 1.5 Hz, 1H), 5.61 (s, 1H), 4.15-4.07 (m, 1H), 4.05-3.97 (m, 1H), 2.95 (dt, J = 11.7, 2.4 Hz, 1H), 2.81 (td, J = 11.9, 3.0 Hz, 1H), 2.74-2.63 (m, 2H), 2.59 (q, J = 7.6 Hz, 2H), 2.48-2.34 (m, 2H), 1.14 (t, J = 7.6 Hz, 3H), 1.03 (d, J = 6.2 Hz, 3H). | 430.1 |

TABLE 2-16-continued

| | | |
|---|---|---|
| 98 | (DMSO-$d_6$) δ 9.15 (s, 1H), 8.99 (s, 1H), 8.34 (dd, J = 7.4, 0.8 Hz, 1H), 8.14 (dd, J = 5.0, 0.7 Hz, 1H), 8.11-8.09 (m, 1H), 8.07-8.05 (m, 1H), 7.75-7.70 (m, 1H), 7.39 (d, J = 1.2 Hz, 1H), 7.13 (dd, J = 7.4, 2.2 Hz, 1H), 6.79 (dd, J = 5.1, 1.5 Hz, 1H), 5.64 (s, 1H), 4.28-4.20 (m, 2H), 2.95-2.83 (m, 2H), 2.59 (q, J = 7.6 Hz, 2H), 1.72-1.60 (m, 3H), 1.19-1.03 (m, 5H), 0.93 (d, J = 6.0 Hz, 3H). | 429.1 |
| 99 | (DMSO-$d_6$) δ 9.16 (s, 1H), 9.02 (s, 1H), 8.37-8.29 (m, 1H), 8.14 (dd, J = 5.1, 0.7 Hz, 1H), 8.12-8.09 (m, 1H), 8.09-8.06 (m, 1H), 7.75-7.70 (m, 1H), 7.41-7.36 (m, 1H), 7.13 (dd, J = 7.4, 2.2 Hz, 1H), 6.79 (dd, J = 5.1, 1.5 Hz, 1H), 5.64 (s, 1H), 3.61-3.53 (m, 4H), 2.58 (q, J = 7.6 Hz, 2H), 1.42-1.34 (m, 4H), 1.13 (t, J = 7.6 Hz, 3H), 0.99 (s, 6H). | 443.1 |

TABLE 2-17

| | | |
|---|---|---|
| 100 | (DMSO-$d_6$) δ 9.24 (s, 1H), 9.06 (s, 1H), 8.34 (dd, J = 7.4, 0.8 Hz, 1H), 8.15 (dd, J = 5.0, 0.7 Hz, 1H), 8.10-8.04 (m, 2H), 7.76-7.70 (m, 1H), 7.42-7.37 (m, 1H), 7.13 (dd, J = 7.4, 2.2 Hz, 1H), 6.81 (dd, J = 5.2, 1.5 Hz, 1H), 5.60 (s, 1H), 4.25-4.16 (m, 1H), 4.09-3.96 (m, 2H), 3.85-3.75 (m, 1H), 3.31-3.27 (m, 1H), 3.25-3.14 (m, 1H), 3.10-2.98 (m, 1H), 2.60 (q, J = 7.6 Hz, 2H), 1.43 (s, 9H), 1.17-1.08 (m, 6H). | 530.1 |
| 101 | (DMSO-$d_6$) δ 9.20 (s, 1H), 9.07 (s, 1H), 8.34 (dd, J = 7.4, 0.8 Hz, 1H), 8.15 (dd, J = 5.0, 0.7 Hz, 1H), 8.11-8.05 (m, 2H), 7.76-7.70 (m, 1H), 7.43-7.36 (m, 1H), 7.13 (dd, J = 7.4, 2.2 Hz, 1H), 6.80 (dd, J = 5.1, 1.5 Hz, 1H), 5.63 (s, 1H), 4.04 (d, J = 10.6 Hz, 2H), 3.09-2.97 (m, 1H), 2.86-2.77 (m, 1H), 2.65 (dd, J = 12.7, 10.1 Hz, 1H), 2.59 (q, J = 7.6 Hz, 2H), 2.22 (s, 3H), 2.20-2.10 (m, 1H), 2.10-2.01 (m, 1H), 1.13 (t, J = 7.6 Hz, 3H), 1.06 (d, J = 6.1 Hz, 3H). | 444.1 |
| 102 | (DMSO-$d_6$) δ 9.17 (s, 1H), 9.04 (s, 1H), 8.34 (dd, J = 7.4, 0.8 Hz, 1H), 8.16-8.12 (m, 1H), 8.11-8.08 (m, 1H), 8.08-8.06 (m, 1H), 7.75-7.70 (m, 1H), 7.41-7.36 (m, 1H), 7.13 (dd, J = 7.4, 2.2 Hz, 1H), 6.80 (dd, J = 5.2, 1.5 Hz, 1H), 5.61 (s, 1H), 4.15-4.05 (m, 1H), 4.05-3.97 (m, 1H), 2.99-2.90 (m, 1H), 2.87-2.75 (m, 1H), 2.73-2.63 (m, 2H), 2.59 (q, J = 7.6 Hz, 2H), 2.45 (dd, J = 12.3, 10.3 Hz, 1H), 2.40-2.30 (m, 1H), 1.14 (t, J = 7.6 Hz, 3H), 1.03 (d, J = 6.2 Hz, 3H). | 430.2 |
| 103 | (DMSO-$d_6$) δ 9.24 (s, 1H), 9.06 (s, 1H), 8.34 (dd, J = 7.4, 0.8 Hz, 1H), 8.15 (dd, J = 5.1, 0.8 Hz, 1H), 8.10-8.04 (m, 2H), 7.76-7.70 (m, 1H), 7.42-7.37 (m, 1H), 7.13 (dd, J = 7.4, 2.2 Hz, 1H), 6.81 (dd, J = 5.1, 1.5 Hz, 1H), 5.60 (s, 1H), 4.25-4.16 (m, 1H), 4.09-3.96 (m, 2H), 3.85-3.75 (m, 1H), 3.31-3.27 (m, 1H), 3.25-3.16 (m, 1H), 3.10-2.98 (m, 1H), 2.60 (q, J = 7.6 Hz, 2H), 1.43 (s, 9H), 1.17-1.08 (m, 6H). | 530.2 |

TABLE 2-18

| | | |
|---|---|---|
| 104 | (DMSO-$d_6$) δ 9.20 (s, 1H), 9.07 (s, 1H), 8.34 (dd, J = 7.4, 0.8 Hz, 1H), 8.15 (dd, J = 5.0, 0.7 Hz, 1H), 8.10-8.05 (m, 2H), 7.76-7.70 (m, 1H), 7.43-7.36 (m, 1H), 7.13 (dd, J = 7.4, 2.2 Hz, 1H), 6.80 (dd, J = 5.1, 1.5 Hz, 1H), 5.63 (s, 1H), 4.07-3.97 (m, 2H), 3.03 (td, J = 11.8, 3.1 Hz, 1H), 2.86-2.77 (m, 1H), 2.66 (dd, J = 12.7, 10.1 Hz, 1H), 2.59 (q, J = 7.6 Hz, 2H), 2.22 (s, 3H), 2.19-2.11 (m, 1H), 2.11-2.01 (m, 1H), 1.13 (t, J = 7.6 Hz, 3H), 1.06 (d, J = 6.1 Hz, 3H). | 444.1 |
| 105 | (DMSO-$d_6$) δ 9.15 (s, 1H), 8.86 (s, 1H), 8.37-8.30 (m, 1H), 8.07-7.98 (m, 2H), 7.73 (s, 1H), 7.65-7.56 (m, 1H), 7.42-7.37 (m, 1H), 7.16 (dd, J = 7.3, 2.2 Hz, 1H), 6.79 (d, J = 7.3 Hz, 1H), 5.63 (s, 1H), 3.58-3.45 (m, 4H), 2.66-2.57 (m, 2H), 1.77-1.50 (m, 8H), 0.92 (t, J = 7.4 Hz, 3H). | 429.2 |

TABLE 2-18-continued

| | | |
|---|---|---|
| 106 | (DMSO-$d_6$) δ 9.15 (s, 1H), 8.86 (s, 1H), 8.34 (d, J = 7.3 Hz, 1H), 8.06-8.03 (m, 1H), 8.03-7.99 (m, 1H), 7.72 (s, 1H), 7.64-7.55 (m, 1H), 7.42-7.37 (m, 1H), 7.16 (dd, J = 7.5, 2.1 Hz, 1H), 6.79 (d, J = 7.3 Hz, 1H), 5.63 (s, 1H), 3.58-3.50 (m, 4H), 2.64 (t, J = 7.7 Hz, 2H), 1.72-1.50 (m, 8H), 1.41-1.26 (m, 2H), 0.91 (t, J = 7.3 Hz, 3H). | 443.2 |
| 107 | (500 MHz, DMSO-$d_6$) δ 9.26 (s, 1H), 9.00 (s, 1H), 8.38-8.32 (m, 1H), 8.09-8.04 (m, 1H), 8.04-7.98 (m, 1H), 7.76-7.72 (m, 1H), 7.62 (t, J = 7.8 Hz, 1H), 7.43-7.39 (m, 1H), 7.17 (dd, J = 7.5, 2.2 Hz, 1H), 6.82 (d, J = 7.3 Hz, 1H), 5.62 (s, 1H), 3.74-3.68 (m, 4H), 3.51-3.45 (m, 4H), 2.67 (q, J = 7.6 Hz, 2H), 1.23 (t, J = 7.6 Hz, 3H). | 417.1 |
| 108 | (DMSO-$d_6$) δ 9.24 (s, 1H), 8.98 (s, 1H), 8.34 (d, J = 7.3 Hz, 1H), 8.08-8.04 (m, 1H), 8.01 (d, J = 8.3 Hz, 1H), 7.76-7.71 (m, 1H), 7.61 (t, J = 7.9 Hz, 1H), 7.43-7.37 (m, 1H), 7.16 (dd, J = 7.3, 2.2 Hz, 1H), 6.80 (d, J = 7.3 Hz, 1H), 5.62 (s, 1H), 3.74-3.67 (m, 4H), 3.52-3.44 (m, 4H), 2.62 (t, J = 7.6 Hz, 2H), 1.70 (h, J = 7.4 Hz, 2H), 0.92 (t, J = 7.3 Hz, 3H). | 431.2 |

TABLE 2-19

| | | |
|---|---|---|
| 109 | (DMSO-$d_6$) δ 9.22 (s, 1H), 8.97 (s, 1H), 8.36-8.29 (m, 1H), 8.07-8.02 (m, 1H), 7.98 (d, J = 8.3 Hz, 1H), 7.74-7.69 (m, 1H), 7.59 (t, J = 7.8 Hz, 1H), 7.41-7.36 (m, 1H), 7.14 (dd, J = 7.5, 2.1 Hz, 1H), 6.78 (d, J = 7.3 Hz, 1H), 5.60 (s, 1H), 3.73-3.65 (m, 4H), 3.50-3.42 (m, 4H), 2.66-2.58 (m, 2H), 1.71-1.59 (m, 2H), 1.32 (h, J = 7.4 Hz, 2H), 0.89 (t, J = 7.4 Hz, 3H). | 445.2 |
| 110 | (500 MHz, DMSO-$d_6$) δ 9.43 (s, 1H), 8.78 (s, 1H), 8.43-8.36 (m, 1H), 8.17-8.11 (m, 1H), 7.93 (d, J = 8.3 Hz, 1H), 7.82-7.75 (m, 1H), 7.56 (t, J = 7.9 Hz, 1H), 7.52-7.48 (m, 1H), 7.26-7.20 (m, 1H), 6.84 (d, J = 7.4 Hz, 1H), 5.64 (s, 1H), 3.74-3.68 (m, 4H), 3.51-3.45 (m, 4H), 2.05-1.96 (m, 1H), 0.98-0.86 (m, 4H). | 429.1 |
| 111 | (DMSO-$d_6$) δ 9.17 (s, 1H), 9.02 (s, 1H), 8.34 (dd, J = 7.4, 0.8 Hz, 1H), 8.14 (dd, J = 5.0, 0.7 Hz, 1H), 8.11-8.03 (m, 2H), 7.75-7.70 (m, 1H), 7.41-7.36 (m, 1H), 7.13 (dd, J = 7.4, 2.2 Hz, 1H), 6.79 (dd, J = 5.1, 1.5 Hz, 1H), 5.65 (s, 1H), 4.78-4.73 (m, 1H), 4.02-3.92 (m, 2H), 3.81-3.70 (m, 1H), 3.25-3.13 (m, 2H), 2.59 (q, J = 7.6 Hz, 2H), 1.86-1.75 (m, 2H), 1.45-1.28 (m, 2H), 1.13 (t, J = 7.6 Hz, 3H). | 431.1 |
| 112 | (DMSO-$d_6$) δ 9.18 (s, 1H), 9.03 (s, 1H), 8.34 (dd, J = 7.4, 0.8 Hz, 1H), 8.14 (dd, J = 5.1, 0.7 Hz, 1H), 8.11-8.08 (m, 1H), 8.08-8.04 (m, 1H), 7.75-7.70 (m, 1H), 7.41-7.36 (m, 1H), 7.12 (dd, J = 7.4, 2.2 Hz, 1H), 6.79 (dd, J = 5.1, 1.5 Hz, 1H), 5.65 (s, 1H), 4.26 (s, 2H), 3.60-3.53 (m, 5H), 2.98-2.85 (m, 2H), 2.59 (q, J = 7.5 Hz, 2H), 2.49-2.40 (m, 4H), 1.89-1.81 (m, 2H), 1.46-1.31 (m, 2H), 1.13 (t, J = 7.6 Hz, 3H). | 500.4 |
| 113 | (DMSO-$d_6$) δ 9.17 (s, 1H), 9.01 (s, 1H), 8.34 (dd, J = 7.3, 0.8 Hz, 1H), 8.14 (dd, J = 5.0, 0.7 Hz, 1H), 8.11-8.08 (m, 1H), 8.08-8.05 (m, 1H), 7.75-7.70 (m, 1H), 7.41-7.36 (m, 1H), 7.12 (dd, J = 7.4, 2.2 Hz, 1H), 6.79 (dd, J = 5.1, 1.5 Hz, 1H), 5.65 (s, 1H), 4.33-4.25 (m, 2H), 2.92-2.81 (m, 2H), 2.59 (q, J = 7.6 Hz, 2H), 2.48-2.42 (m, 5H), 1.83-1.74 (m, 2H), 1.53-1.32 (m, 8H), 1.13 (t, J = 7.6 Hz, 3H). | 498.1 |

TABLE 2-20

| | | |
|---|---|---|
| 114 | (DMSO-$d_6$) δ 9.18 (s, 1H), 9.03 (s, 1H), 8.34 (dd, J = 7.4, 0.8 Hz, 1H), 8.14 (dd, J = 5.2, 0.7 Hz, 1H), 8.11-8.04 (m, 2H), 7.77-7.68 (m, 1H), 7.42-7.36 (m, 1H), 7.12 (dd, J = 7.4, 2.2 Hz, 1H), 6.83-6.76 (m, 1H), 5.66 (s, 1H), 3.95-3.85 (m, 2H), | 445.1 |

TABLE 2-20-continued

| | | |
|---|---|---|
| | 3.53-3.40 (m, 1H), 3.29 (s, 3H), 3.28-3.22 (m, 2H), 2.59 (q, J = 7.6 Hz, 2H), 1.97-1.85 (m, 2H), 1.52-1.38 (m, 2H), 1.13 (t, J = 7.6 Hz, 3H). | |
| 115 | (DMSO-d$_6$) δ 9.19 (s, 1H), 9.05 (s, 1H), 8.33 (dd, J = 7.4, 0.8 Hz, 1H), 8.26-8.20 (m, 1H), 8.16-8.11 (m, 1H), 8.10-8.05 (m, 1H), 7.75-7.70 (m, 1H), 7.41-7.36 (m, 1H), 7.15 (dd, J = 7.4, 2.2 Hz, 1H), 6.82-6.76 (m, 1H), 5.74 (d, J = 6.3 Hz, 1H), 5.27 (s, 1H), 4.65-4.58 (m, 1H), 4.26-4.17 (m, 2H), 3.75 (dd, J = 8.7, 4.5 Hz, 2H), 2.59 (q, J = 7.6 Hz, 2H), 1.15 (t, J = 7.6 Hz, 3H). | 403.1 |
| 116 | (DMSO-d$_6$) δ 9.16 (s, 1H), 8.93 (s, 1H), 8.33 (dd, J = 7.4, 0.8 Hz, 1H), 8.31-8.27 (m, 1H), 8.16-8.09 (m, 1H), 8.09-8.03 (m, 1H), 7.75-7.69 (m, 1H), 7.41-7.36 (m, 1H), 7.18 (dd, J = 7.4, 2.2 Hz, 1H), 6.82-6.76 (m, 1H), 5.39-5.34 (m, 1H), 5.04-4.98 (m, 1H), 4.43-4.38 (m, 1H), 3.65-3.43 (m, 4H), 2.60 (q, J = 7.6 Hz, 2H), 2.11-1.83 (m, 2H), 1.16 (t, J = 7.6 Hz, 3H). | 417.0 |
| 117 | (DMSO-d$_6$) δ 9.16 (s, 1H), 8.93 (s, 1H), 8.33 (dd, J = 7.4, 0.8 Hz, 1H), 8.29 (dd, J = 1.7, 0.9 Hz, 1H), 8.16-8.09 (m, 1H), 8.09-8.03 (m, 1H), 7.75-7.69 (m, 1H), 7.41-7.36 (m, 1H), 7.18 (dd, J = 7.5, 2.2 Hz, 1H), 6.79 (dd, J = 5.1, 1.4 Hz, 1H), 5.39-5.34 (m, 1H), 5.04-4.98 (m, 1H), 4.43-4.38 (m, 1H), 3.72-3.39 (m, 4H), 2.60 (q, J = 7.6 Hz, 2H), 2.13-1.84 (m, 2H), 1.16 (t, J = 7.6 Hz, 3H). | 417.1 |
| 118 | (DMSO-d$_6$) δ 9.19 (s, 1H), 9.00 (s, 1H), 8.33 (dd, J = 7.4, 0.8 Hz, 1H), 8.26-8.21 (m, 1H), 8.14 (dd, J = 5.1, 0.8 Hz, 1H), 8.10-8.04 (m, 1H), 7.75-7.70 (m, 1H), 7.41-7.36 (m, 1H), 7.15 (dd, J = 7.4, 2.2 Hz, 1H), 6.79 (dd, J = 5.1, 1.5 Hz, 1H), 5.25 (s, 1H), 4.02 (t, J = 7.4 Hz, 4H), 2.58 (q, J = 7.6 Hz, 2H), 2.43-2.33 (m, 2H), 1.14 (t, J = 7.6 Hz, 3H). | 387.1 |

TABLE 2-21

| | | |
|---|---|---|
| 119 | (DMSO-d$_6$) δ 9.15 (s, 1H), 9.00 (s, 1H), 8.33 (dd, J = 7.4, 0.8 Hz, 1H), 8.14 (dd, J = 5.0, 0.7 Hz, 1H), 8.12-8.09 (m, 1H), 8.08-8.04 (m, 1H), 7.75-7.70 (m, 1H), 7.41-7.36 (m, 1H), 7.13 (dd, J = 7.4, 2.2 Hz, 1H), 6.79 (dd, J = 5.1, 1.5 Hz, 1H), 5.64 (s, 1H), 4.49 (t, J = 5.3 Hz, 1H), 4.27 (d, J = 12.7 Hz, 2H), 3.31-3.26 (m, 2H), 2.96-2.84 (m, 2H), 2.59 (q, J = 7.6 Hz, 2H), 1.77-1.62 (m, 3H), 1.22-1.07 (m, 5H). | 445.1 |
| 120 | (DMSO-d$_6$) δ 9.15 (s, 1H), 8.95 (s, 1H), 8.36-8.29 (m, 1H), 8.17-8.10 (m, 2H), 8.09-8.02 (m, 1H), 7.74-7.69 (m, 1H), 7.41-7.36 (m, 1H), 7.15 (dd, J = 7.5, 2.2 Hz, 1H), 6.80 (dd, J = 5.1, 1.5 Hz, 1H), 5.59 (s, 1H), 3.90-3.51 (m, 16H), 2.58 (q, J = 7.6 Hz, 2H), 1.14 (t, J = 7.6 Hz, 3H). | 505.3 |
| 121 | (DMSO-d$_6$) δ 9.15 (s, 1H), 8.75 (s, 1H), 8.37-8.31 (m, 1H), 8.08-8.04 (m, 1H), 8.04-7.98 (m, 1H), 7.75-7.70 (m, 1H), 7.67-7.58 (m, 1H), 7.42-7.37 (m, 1H), 7.13 (dd, J = 7.3, 2.1 Hz, 1H), 6.82 (d, J = 7.4 Hz, 1H), 5.63 (s, 1H), 3.58-3.50 (m, 4H), 2.99-2.84 (m, 1H), 1.69-1.50 (m, 6H), 1.24 (d, J = 6.9 Hz, 6H). | 429.4 |
| 122 | (DMSO-d$_6$) δ 9.16 (s, 1H), 8.60 (s, 1H), 8.35 (d, J = 7.3 Hz, 1H), 8.11-8.03 (m, 1H), 8.03-7.96 (m, 1H), 7.73 (s, 1H), 7.68-7.59 (m, 1H), 7.42-7.37 (m, 1H), 7.09 (dd, J = 7.4, 2.2 Hz, 1H), 6.96 (d, J = 7.6 Hz, 1H), 5.63 (s, 1H), 3.58-3.51 (m, 4H), 1.69-1.50 (m, 6H), 1.32 (s, 9H). | 443.2 |
| 123 | (DMSO-d$_6$) δ 9.29 (s, 1H), 8.89 (s, 1H), 8.40-8.34 (m, 1H), 8.27-8.22 (m, 2H), 8.14-8.08 (m, 1H), 8.01 (d, J = 8.3 Hz, 1H), 7.78-7.73 (m, 1H), 7.63 (t, J = 7.9 Hz, 1H), 7.45-7.40 (m, 1H), 7.15 (d, J = 7.2 Hz, 1H), 6.83 (d, J = 7.4 Hz, 1H), 5.64 (s, 1H), 3.80-3.59 (m, 4H), 3.56-3.45 (m, 4H), 3.00-2.84 (m, 1H), 1.24 (d, J = 6.9 Hz, 6H). | 431.3 |

TABLE 2-22

| | | |
|---|---|---|
| 124 | (DMSO-d$_6$) δ 9.27 (s, 1H), 8.72 (s, 1H), 8.40-8.33 (m, 1H), 8.11-8.05 (m, 1H), 7.99 (d, J = 8.2 Hz, 1H), 7.76-7.71 (m, 1H), 7.64 (t, J = 7.9 Hz, 1H), 7.43-7.38 (m, 1H), 7.11 (dd, J = 7.4, 2.1 Hz, 1H), 6.97 (d, J = 7.5 Hz, 1H), 5.63 (s, 1H), 3.75-3.67 (m, 4H), 3.52-3.45 (m, 4H), 1.32 (s, 9H). | 445.2 |
| 125 | (DMSO-d$_6$) δ 9.16 (s, 1H), 8.98 (s, 1H), 8.32 (dd, J = 7.4, 0.8 Hz, 1H), 8.31-8.27 (m, 1H), 8.13 (dd, J = 5.1, 0.7 Hz, 1H), 8.09-8.04 (m, 1H), 7.75-7.69 (m, 1H), 7.41-7.36 (m, 1H), 7.19 (dd, J = 7.4, 2.2 Hz, 1H), 6.79 (dd, J = 5.1, 1.5 Hz, 1H), 5.37 (s, 1H), 4.03-3.35 (m, 3H), 3.25-3.08 (m, 1H), 2.87-2.69 (m, 1H), 2.59 (q, J = 7.6 Hz, 2H), 2.26-2.14 (m, 7H), 1.90-1.75 (m, 1H), 1.16 (t, J = 7.6 Hz, 3H). | 444.1 |
| 126 | (DMSO-d$_6$) δ 9.17 (s, 1H), 8.99 (s, 1H), 8.33 (dd, J = 7.4, 0.8 Hz, 1H), 8.31-8.27 (m, 1H), 8.16-8.11 (m, 1H), 8.10-8.06 (m, 1H), 7.75-7.69 (m, 1H), 7.41-7.36 (m, 1H), 7.19 (dd, J = 7.5, 2.2 Hz, 1H), 6.79 (dd, J = 5.1, 1.5 Hz, 1H), 5.37 (s, 1H), 3.25-3.10 (m, 2H), 2.88-2.71 (m, 1H), 2.59 (q, J = 7.6 Hz, 2H), 2.26-2.13 (m, 7H), 1.92-1.75 (m, 2H), 1.16 (t, J = 7.6 Hz, 3H). | 444.0 |
| 127 | (DMSO-d$_6$) δ 9.17 (s, 1H), 9.00 (s, 1H), 8.34 (dd, J = 7.4, 0.8 Hz, 1H), 8.14 (dd, J = 5.1, 0.8 Hz, 1H), 8.10-8.08 (m, 1H), 8.07-8.05 (m, 1H), 7.75-7.70 (m, 1H), 7.41-7.36 (m, 1H), 7.12 (dd, J = 7.4, 2.2 Hz, 1H), 6.79 (dd, J = 5.1, 1.5 Hz, 1H), 5.65 (s, 1H), 4.17-4.09 (m, 2H), 3.08-2.97 (m, 2H), 2.59 (q, J = 7.6 Hz, 2H), 2.53-2.51 (m, 4H), 2.32-2.20 (m, 1H), 1.95-1.86 (m, 2H), 1.74-1.63 (m, 4H), 1.47-1.33 (m, 2H), 1.13 (t, J = 7.6 Hz, 3H). | 484.4 |
| 128 | (DMSO-d$_6$) δ 9.17 (s, 1H), 9.02 (s, 1H), 8.32 (dd, J = 7.3, 0.8 Hz, 1H), 8.13-8.10 (m, 1H), 8.09-8.06 (m, 1H), 8.06-8.03 (m, 1H), 7.75-7.69 (m, 1H), 7.41-7.36 (m, 1H), 7.23 (dd, J = 7.4, 2.2 Hz, 1H), 6.52 (dd, J = 5.7, 2.4 Hz, 1H), 5.38 (s, 1H), 3.80 (s, 3H), 3.59-3.39 (m, 4H), 2.00-1.92 (m, 4H). | 403.0 |

TABLE 2-23

| | | |
|---|---|---|
| 129 | (DMSO-d$_6$) δ 9.18 (s, 1H), 9.02 (s, 1H), 8.34 (dd, J = 7.4, 0.8 Hz, 1H), 8.14 (dd, J = 5.1, 0.8 Hz, 1H), 8.11-8.08 (m, 1H), 8.08-8.06 (m, 1H), 7.75-7.70 (m, 1H), 7.41-7.36 (m, 1H), 7.12 (dd, J = 7.4, 2.2 Hz, 1H), 6.80 (dd, J = 5.1, 1.5 Hz, 1H), 5.65 (s, 1H), 4.30-4.21 (m, 2H), 2.97-2.85 (m, 2H), 2.59 (q, J = 7.6 Hz, 2H), 2.43-2.32 (m, 1H), 2.18 (s, 6H), 1.86-1.78 (m, 2H), 1.43-1.28 (m, 2H), 1.13 (t, J = 7.6 Hz, 3H). | 458.2 |
| 130 | (DMSO-d$_6$) δ 9.16 (s, 1H), 8.80 (s, 1H), 8.37-8.30 (m, 1H), 8.04-7.99 (m, 1H), 7.90-7.85 (m, 1H), 7.75-7.70 (m, 1H), 7.41-7.36 (m, 1H), 7.12 (dd, J = 7.4, 2.1 Hz, 1H), 6.69-6.62 (m, 1H), 5.64 (s, 1H), 4.73 (d, J = 4.3 Hz, 1H), 4.01-3.90 (m, 2H), 3.80-3.69 (m, 1H), 3.25-3.09 (m, 2H), 2.34 (s, 3H), 2.23 (s, 3H), 1.85-1.76 (m, 2H), 1.44-1.30 (m, 2H). | 431.4 |
| 131 | (DMSO-d$_6$) δ 9.19 (s, 1H), 8.82 (s, 1H), 8.38-8.31 (m, 1H), 8.05-8.00 (m, 1H), 7.90-7.85 (m, 1H), 7.76-7.71 (m, 1H), 7.42-7.37 (m, 1H), 7.13 (dd, J = 7.3, 2.2 Hz, 1H), 6.67-6.62 (m, 1H), 5.65 (s, 1H), 3.94-3.84 (m, 2H), 3.51-3.40 (m, 1H), 3.27 (d, J = 16.2 Hz, 5H), 2.34 (s, 3H), 2.23 (s, 3H), 1.97-1.86 (m, 2H), 1.44 (dtd, J = 12.8, 8.9, 3.7 Hz, 2H). | 445.4 |
| 132 | (DMSO-d$_6$) δ 9.18 (s, 1H), 8.81 (s, 1H), 8.38-8.31 (m, 1H), 8.05-7.99 (m, 1H), 7.90-7.85 (m, 1H), 7.75-7.70 (m, 1H), 7.42-7.37 (m, 1H), 7.13 (dd, J = 7.4, 2.1 Hz, 1H), 6.69-6.62 (m, 1H), 5.65 (s, 1H), 4.29-4.20 (m, 2H), 3.60-3.53 (m, 4H), 2.96-2.84 (m, 2H), 2.48-2.39 (m, 5H), 2.34 (s, 3H), 2.24 (s, 3H), 1.91-1.82 (m, 2H), 1.45-1.30 (m, 2H). | 500.5 |
| 133 | (DMSO-d$_6$) δ 9.17 (s, 1H), 8.80 (s, 1H), 8.34 (d, J = 7.4 Hz, 1H), 8.04-7.99 (m, 1H), 7.91-7.86 (m, 1H), 7.75-7.70 (m, 1H), 7.42-7.34 (m, 1H), | 498.5 |

TABLE 2-23-continued

| | | |
|---|---|---|
| | 7.12 (dd, J = 7.4, 2.2 Hz, 1H), 6.67-6.62 (m, 1H), 5.64 (s, 1H), 4.31-4.23 (m, 2H), 2.93-2.79 (m, 2H), 2.48-2.41 (m, 5H), 2.34 (s, 3H), 2.24 (s, 3H), 1.83-1.75 (m, 2H), 1.52-1.31 (m, 8H). | |

TABLE 2-24

| | | |
|---|---|---|
| 134 | (DMSO-d$_6$) δ 9.16 (s, 1H), 8.81 (s, 1H), 8.34 (d, J = 7.4 Hz, 1H), 8.04-7.99 (m, 1H), 7.91-7.86 (m, 1H), 7.75-7.70 (m, 1H), 7.41-7.36 (m, 1H), 7.12 (dd, J = 7.4, 2.2 Hz, 1H), 6.67-6.62 (m, 1H), 5.64 (s, 1H), 4.28-4.19 (m, 2H), 2.96-2.84 (m, 2H), 2.43-2.32 (m, 4H), 2.24 (s, 6H), 2.19 (s, 3H), 1.87-1.78 (m, 2H), 1.43-1.28 (m, 2H). | 458.4 |
| 135 | (DMSO-d$_6$) δ 9.15 (s, 1H), 8.69 (s, 1H), 8.32 (d, J = 7.3 Hz, 1H), 8.10-8.05 (m, 1H), 8.05-7.99 (m, 1H), 7.74-7.69 (m, 1H), 7.40-7.35 (m, 1H), 7.19 (dd, J = 7.5, 2.2 Hz, 1H), 6.65-6.60 (m, 1H), 5.36 (s, 1H), 3.53-3.37 (m, 4H), 2.34 (s, 3H), 2.24 (s, 3H), 2.04-1.86 (m, 4H). | 401.2 |
| 136 | (DMSO-d$_6$) δ 9.15 (s, 1H), 8.72 (s, 1H), 8.36-8.29 (m, 1H), 8.10-8.05 (m, 1H), 8.05-7.99 (m, 1H), 7.74-7.69 (m, 1H), 7.41-7.34 (m, 1H), 7.20 (dd, J = 7.4, 2.2 Hz, 1H), 6.66-6.61 (m, 1H), 5.35 (s, 1H), 5.03-4.97 (m, 1H), 4.43-4.38 (m, 1H), 4.13-4.04 (m, 1H), 3.68-3.40 (m, 3H), 2.34 (s, 3H), 2.25 (s, 3H), 2.09-1.97 (m, 1H), 1.95-1.90 (m, 1H). | 417.4 |
| 137 | (DMSO-d$_6$) δ 9.16 (s, 1H), 8.77 (s, 1H), 8.36-8.29 (m, 1H), 8.12-8.06 (m, 1H), 8.06-8.00 (m, 1H), 7.74-7.69 (m, 1H), 7.41-7.36 (m, 1H), 7.20 (dd, J = 7.4, 2.2 Hz, 1H), 6.66-6.61 (m, 1H), 5.36 (s, 1H), 4.04-3.07 (m, 4H), 2.88-2.70 (m, 1H), 2.34 (s, 3H), 2.28-2.12 (m, 10H), 1.89-1.74 (m, 1H). | 444.4 |
| 138 | (DMSO-d$_6$) δ 9.28 (s, 1H), 8.91 (s, 1H), 8.38-8.31 (m, 1H), 8.07-7.99 (m, 1H), 7.99-7.94 (m, 1H), 7.76-7.71 (m, 1H), 7.42-7.37 (m, 1H), 7.18 (dd, J = 7.4, 2.1 Hz, 1H), 6.69-6.63 (m, 1H), 5.41 (s, 1H), 3.94-3.82 (m, 2H), 3.71-3.62 (m, 2H), 2.65-2.51 (m, 2H), 2.35 (s, 3H), 2.25 (s, 3H). | 437.4 |

TABLE 2-25

| | | |
|---|---|---|
| 139 | (DMSO-d$_6$) δ 9.21 (s, 1H), 8.79 (s, 1H), 8.37-8.30 (m, 1H), 8.10-8.05 (m, 1H), 8.05-8.02 (m, 1H), 7.75-7.70 (m, 1H), 7.41-7.36 (m, 1H), 7.21 (dd, J = 7.4, 2.1 Hz, 1H), 6.67-6.62 (m, 1H), 6.05 (s, 2H), 5.37 (s, 1H), 4.43-4.06 (m, 4H), 2.35 (s, 3H), 2.26 (s, 3H). | 399.3 |
| 140 | (DMSO-d$_6$) δ 9.17 (s, 1H), 8.74 (s, 1H), 8.36-8.29 (m, 1H), 8.09-8.03 (m, 1H), 8.05-7.98 (m, 1H), 7.74-7.69 (m, 1H), 7.41-7.35 (m, 1H), 7.19 (dd, J = 7.5, 2.2 Hz, 1H), 6.64 (s, 1H), 5.36 (s, 1H), 4.16-4.02 (m, 1H), 3.67-3.34 (m, 4H), 3.29 (s, 3H), 2.34 (s, 3H), 2.25 (s, 3H), 2.12-2.04 (m, 2H). | 431.2 |
| 141 | (DMSO-d$_6$) δ 9.17 (s, 1H), 8.84 (s, 1H), 8.36-8.30 (m, 1H), 8.05-8.00 (m, 1H), 7.77-7.71 (m, 2H), 7.43-7.38 (m, 1H), 7.25 (dd, J = 7.4, 2.1 Hz, 1H), 6.61-6.56 (m, 1H), 5.61 (s, 1H), 3.59-3.52 (m, 4H), 2.33 (s, 3H), 1.87-1.77 (m, 1H), 1.71-1.52 (m, 6H), 1.03-0.93 (m, 2H), 0.77-0.65 (m, 2H). | 441.3 |
| 142 | (500 MHz, DMSO-d$_6$) δ 9.23 (s, 1H), 8.71 (s, 1H), 8.37-8.32 (m, 1H), 8.09-8.03 (m, 2H), 7.77-7.73 (m, 1H), 7.46-7.40 (m, 1H), 7.23 (dd, J = 7.4, 2.2 Hz, 1H), 6.66-6.62 (m, 1H), 5.35 (s, 1H), 3.79-3.04 (m, 4H), 2.34 (s, 3H), 2.24 (s, 3H), 1.81-1.75 (m, 2H), 1.12 (s, 6H). | 429.4 |

TABLE 2-26

| | | |
|---|---|---|
| 143 | (400 MHz, DMSO-d$_6$) δ 9.17 (s, 1H), 8.75 (s, 1H), 8.37-8.29 (m, 1H), 8.14-8.09 (m, 1H), 8.02-7.95 (m, 1H), 7.75-7.69 (m, 1H), 7.61 (t, J = 8.0 Hz, 1H), 7.42-7.36 (m, 1H), 7.13 (dd, J = 7.4, 2.2 Hz, 1H), 6.33 (dd, J = 7.9, 0.7 Hz, 1H), 5.37 (s, 1H), 3.86 (s, 3H), 3.53-3.36 (m, 4H), 2.00-1.92 (m, 4H). | 403.2 |
| 144 | (400 MHz, DMSO-d$_6$) δ 9.17 (s, 1H), 8.81 (s, 1H), 8.35 (dd, J = 7.4, 0.8 Hz, 1H), 8.11-8.05 (m, 1H), 7.82-7.76 (m, 1H), 7.75-7.70 (m, 1H), 7.61 (t, J = 7.9 Hz, 1H), 7.42-7.37 (m, 1H), 7.09 (dd, J = 7.4, 2.2 Hz, 1H), 6.34 (dd, J = 8.0, 0.7 Hz, 1H), 5.64 (s, 1H), 3.85 (s, 3H), 3.59-3.51 (m, 4H), 1.70-1.51 (m, 6H). | 417.2 |
| 145 | (400 MHz, DMSO-d$_6$) δ 9.16 (s, 1H), 8.96 (s, 1H), 8.32 (dd, J = 7.4, 0.8 Hz, 1H), 8.10-8.07 (m, 1H), 8.06-8.01 (m, 2H), 7.75-7.69 (m, 1H), 7.41-7.36 (m, 1H), 7.21 (dd, J = 7.4, 2.2 Hz, 1H), 6.52-6.45 (m, 1H), 5.37 (s, 1H), 4.06 (q, J = 7.0 Hz, 2H), 3.47-3.42 (m, 4H), 2.00-1.92 (m, 4H), 1.28 (t, J = 6.9 Hz, 3H). | 417.2 |
| 146 | (500 MHz, DMSO-d$_6$) δ 9.15 (s, 1H), 8.71 (s, 1H), 8.36-8.30 (m, 1H), 8.09-8.05 (m, 1H), 8.06-8.00 (m, 1H), 7.74-7.70 (m, 1H), 7.42-7.35 (m, 1H), 7.19 (dd, J = 7.5, 2.2 Hz, 1H), 6.66-6.61 (m, 1H), 5.34 (s, 1H), 3.97-2.84 (m, 4H), 2.39-2.30 (m, 4H), 2.24 (s, 3H), 2.15-2.05 (m, 1H), 1.65-1.54 (m, 1H), 1.09 (d, J = 6.6 Hz, 3H). | 415.2 |
| 147 | (500 MHz, DMSO-d$_6$) δ 9.19-9.15 (m, 1H), 8.73-8.67 (m, 1H), 8.36-8.32 (m, 1H), 8.18-8.14 (m, 1H), 8.10-8.06 (m, 1H), 8.06-7.98 (m, 1H), 7.75-7.71 (m, 1H), 7.42-7.38 (m, 1H), 7.23-7.17 (m, 1H), 6.67-6.61 (m, 1H), 5.36-5.32 (m, 1H), 3.87-2.83 (m, 4H), 2.39-2.32 (m, 4H), 2.24 (s, 3H), 1.87-1.83 (m, 1H), 1.14-0.90 (m, 6H). | 429.2 |

TABLE 2-27

| | | |
|---|---|---|
| 148 | (400 MHz, DMSO-d$_6$) δ 9.15 (s, 1H), 8.76 (s, 1H), 8.36-8.29 (m, 1H), 8.10-8.05 (m, 1H), 8.05-8.00 (m, 1H), 7.74-7.69 (m, 1H), 7.41-7.35 (m, 1H), 7.20 (dd, J = 7.4, 2.2 Hz, 1H), 6.66-6.61 (m, 1H), 5.35 (s, 1H), 4.06-3.12 (m, 9H), 2.86-2.81 (m, 1H), 2.60-2.52 (m, 3H), 2.34 (s, 3H), 2.24 (s, 3H), 2.21-2.13 (m, 1H), 1.95-1.86 (m, 1H). | 470.2 |
| 149 | (400 MHz, DMSO-d$_6$) δ 9.16 (s, 1H), 8.75 (s, 1H), 8.36-8.29 (m, 1H), 8.10-8.04 (m, 1H), 8.04-7.98 (m, 1H), 7.74-7.69 (m, 1H), 7.41-7.35 (m, 1H), 7.19 (dd, J = 7.5, 2.2 Hz, 1H), 6.66-6.61 (m, 1H), 5.36 (s, 1H), 4.03-3.45 (m, 8H), 3.24-3.18 (m, 1H), 2.95-2.90 (m, 1H), 2.59-2.38 (m, 3H), 2.34 (s, 3H), 2.23 (s, 3H), 2.22-2.14 (m, 1H), 1.89-1.76 (m, 1H). | 486.2 |
| 150 | (400 MHz, DMSO-d$_6$) δ 9.16 (s, 1H), 8.66 (s, 1H), 8.37-8.30 (m, 1H), 8.13-8.07 (m, 1H), 7.99-7.92 (m, 1H), 7.75-7.69 (m, 1H), 7.60 (t, J = 8.0 Hz, 1H), 7.42-7.36 (m, 1H), 7.13 (dd, J = 7.4, 2.2 Hz, 1H), 6.34-6.24 (m, 1H), 5.37 (s, 1H), 4.32 (q, J = 7.0 Hz, 2H), 3.58-3.35 (m, 4H), 2.00-1.92 (m, 4H), 1.32 (t, J = 7.0 Hz, 3H). | 417.1 |
| 151 | (400 MHz, DMSO-d$_6$) δ 9.16 (s, 1H), 8.70 (s, 1H), 8.40-8.30 (m, 1H), 8.13-8.07 (m, 1H), 7.99-7.92 (m, 1H), 7.74-7.69 (m, 1H), 7.60 (t, J = 8.0 Hz, 1H), 7.41-7.36 (m, 1H), 7.13 (dd, J = 7.4, 2.2 Hz, 1H), 6.34-6.27 (m, 1H), 5.37 (s, 1H), 4.22 (t, J = 6.7 Hz, 2H), 3.46-3.41 (m, 4H), 2.00-1.92 (m, 4H), 1.80-1.66 (m, 2H), 0.98 (t, J = 7.4 Hz, 3H). | 431.4 |
| 152 | (400 MHz, DMSO-d$_6$) δ 9.17 (s, 1H), 8.73 (s, 1H), 8.37-8.30 (m, 1H), 8.13-8.08 (m, 1H), 8.00-7.93 (m, 1H), 7.74-7.69 (m, 1H), 7.61 (t, J = 8.0 Hz, 1H), 7.42-7.34 (m, 1H), 7.13 (dd, J = 7.6, 2.1 Hz, 1H), 6.36-6.29 (m, 1H), 5.38 (s, 1H), 4.44-4.36 (m, 2H), 3.66 (t, J = 4.8 Hz, 2H), 3.58-3.38 (m, 4H), 3.31 (s, 3H), 2.00-1.92 (m, 4H). | 447.3 |

TABLE 2-28

| | | |
|---|---|---|
| 153 | (400 MHz, DMSO-$d_6$) δ 9.16 (s, 1H), 8.66 (s, 1H), 8.37-8.30 (m, 1H), 8.14-8.09 (m, 1H), 7.97-7.90 (m, 1H), 7.74-7.69 (m, 1H), 7.57 (t, J = 7.9 Hz, 1H), 7.41-7.36 (m, 1H), 7.11 (dd, J = 7.4, 2.2 Hz, 1H), 6.29-6.22 (m, 1H), 5.37 (s, 1H), 5.36-5.22 (m, 1H), 3.61-3.39 (m, 4H), 2.00-1.92 (m, 4H), 1.29 (d, J = 6.2 Hz, 6H). | 431.1 |
| 154 | (400 MHz, DMSO-$d_6$) δ 9.15 (s, 1H), 8.74 (s, 1H), 8.37-8.30 (m, 1H), 8.13-8.07 (m, 1H), 7.99-7.92 (m, 1H), 7.74-7.69 (m, 1H), 7.60 (t, J = 8.0 Hz, 1H), 7.41-7.36 (m, 1H), 7.12 (dd, J = 7.4, 2.2 Hz, 1H), 6.35-6.28 (m, 1H), 5.37 (s, 1H), 4.39 (t, J = 5.9 Hz, 2H), 3.61-3.54 (m, 4H), 3.51-3.36 (m, 4H), 2.68 (t, J = 5.9 Hz, 2H), 2.51-2.43 (m, 4H), 2.00-1.92 (m, 4H). | 502.1 |
| 155 | (400 MHz, DMSO-$d_6$) δ 9.16 (s, 1H), 8.74 (s, 1H), 8.37-8.30 (m, 1H), 8.12-8.07 (m, 1H), 7.99-7.92 (m, 1H), 7.74-7.69 (m, 1H), 7.60 (t, J = 8.0 Hz, 1H), 7.41-7.36 (m, 1H), 7.13 (dd, J = 7.5, 2.2 Hz, 1H), 6.34-6.27 (m, 1H), 5.38 (s, 1H), 4.35 (t, J = 5.9 Hz, 2H), 3.56-3.37 (m, 4H), 2.62 (t, J = 5.9 Hz, 2H), 2.22 (s, 6H), 2.00-1.90 (m, 4H). | 460.2 |
| 156 | (400 MHz, DMSO-$d_6$) δ 9.16 (s, 1H), 8.71 (s, 1H), 8.37-8.30 (m, 1H), 8.11-8.06 (m, 1H), 8.00-7.93 (m, 1H), 7.74-7.69 (m, 1H), 7.60 (t, J = 8.0 Hz, 1H), 7.42-7.36 (m, 1H), 7.14 (dd, J = 7.4, 2.2 Hz, 1H), 6.36-6.29 (m, 1H), 5.38 (s, 1H), 4.32 (t, J = 5.1 Hz, 2H), 3.64 (t, J = 5.1 Hz, 2H), 3.58-3.38 (m, 4H), 2.00-1.92 (m, 4H), 1.16 (s, 9H). | 489.1 |
| 157 | (500 MHz, DMSO-$d_6$) δ 9.19-9.15 (m, 1H), 8.71 (s, 1H), 8.37-8.31 (m, 1H), 8.12-8.08 (m, 1H), 8.00-7.93 (m, 1H), 7.74-7.70 (m, 1H), 7.64-7.57 (m, 1H), 7.41-7.37 (m, 1H), 7.13 (dd, J = 7.4, 2.2 Hz, 1H), 6.36-6.30 (m, 1H), 5.37 (s, 1H), 4.82-4.76 (m, 1H), 4.29 (t, J = 5.2 Hz, 2H), 3.75-3.68 (m, 2H), 3.62-3.35 (m, 4H), 1.99-1.93 (m, 4H). | 433.2 |

TABLE 2-29

| | | |
|---|---|---|
| 158 | (400 MHz, DMSO-$d_6$) δ 9.16 (s, 1H), 8.74 (s, 1H), 8.37-8.30 (m, 1H), 8.14-8.09 (m, 1H), 7.99-7.92 (m, 1H), 7.74-7.69 (m, 1H), 7.60 (t, J = 8.0 Hz, 1H), 7.42-7.36 (m, 1H), 7.14 (dd, J = 7.4, 2.2 Hz, 1H), 6.35-6.28 (m, 1H), 5.37 (s, 1H), 4.05 (d, J = 6.7 Hz, 2H), 3.64-3.35 (m, 4H), 2.12-1.86 (m, 5H), 0.98 (d, J = 6.7 Hz, 6H). | 445.3 |
| 159 | (500 MHz, DMSO-$d_6$) δ 9.16 (s, 1H), 8.87 (s, 1H), 8.33 (dd, J = 7.4, 0.8 Hz, 1H), 8.26-8.20 (m, 1H), 8.09-8.05 (m, 1H), 7.74-7.70 (m, 1H), 7.65-7.58 (m, 1H), 7.41-7.37 (m, 1H), 7.21 (dd, J = 7.4, 2.2 Hz, 1H), 6.85-6.79 (m, 1H), 5.36 (s, 1H), 3.70 (t, J = 6.8 Hz, 2H), 3.56-3.38 (m, 4H), 3.25 (s, 3H), 2.87 (t, J = 6.8 Hz, 2H), 1.99-1.93 (m, 4H). | 431.1 |
| 160 | (500 MHz, DMSO-$d_6$) δ 9.30 (s, 1H), 8.86 (s, 1H), 8.39-8.34 (m, 1H), 8.26-8.21 (m, 1H), 8.16-8.12 (m, 1H), 7.80-7.75 (m, 1H), 7.67-7.58 (m, 1H), 7.48-7.44 (m, 1H), 7.29 (dd, J = 7.6, 2.2 Hz, 1H), 6.86-6.81 (m, 1H), 5.38 (s, 1H), 3.72 (t, J = 7.0 Hz, 2H), 3.63-3.37 (m, 6H), 2.87 (t, J = 6.9 Hz, 2H), 2.01-1.93 (m, 4H), 1.09 (t, J = 7.0 Hz, 3H). | 445.1 |
| 161 | (500 MHz, DMSO-$d_6$) δ 9.35 (s, 1H), 8.81 (s, 1H), 8.40-8.35 (m, 1H), 8.26-8.20 (m, 1H), 8.18-8.14 (m, 1H), 7.81-7.77 (m, 1H), 7.65-7.58 (m, 1H), 7.51-7.47 (m, 1H), 7.34 (dd, J = 7.5, 2.2 Hz, 1H), 6.78-6.73 (m, 1H), 5.39 (s, 1H), 3.55-3.37 (m, 4H), 2.53-2.49 (m, 2H), 2.14-2.02 (m, 1H), 2.00-1.93 (m, 4H), 0.90 (d, J = 6.6 Hz, 6H). | 429.3 |
| 162 | (500 MHz, DMSO-$d_6$) δ 9.16 (s, 1H), 8.65 (s, 1H), 8.37-8.30 (m, 1H), 8.29-8.22 (m, 1H), 8.10-8.05 (m, 1H), 7.74-7.70 (m, 1H), 7.66-7.57 (m, 1H), 7.41-7.37 (m, 1H), 7.19 (dd, J = 7.4, 2.2 Hz, 1H), 6.74 (dd, J = 7.5, 0.9 Hz, 1H), 5.36 (s, 1H), 3.60-3.37 (m, 4H), 2.54 (s, 2H), 2.01-1.88 (m, 4H), 0.95 (s, 9H). | 443.4 |

TABLE 2-30

| | | |
|---|---|---|
| 163 | (500 MHz, DMSO-$d_6$) δ 9.18 (s, 1H), 8.90 (s, 1H), 8.36-8.30 (m, 1H), 8.26-8.19 (m, 4H), 8.11-8.07 (m, 1H), 7.74-7.70 (m, 1H), 7.65-7.58 (m, 1H), 7.41-7.37 (m, 1H), 7.18 (dd, J = 7.4, 2.1 Hz, 1H), 6.86-6.81 (m, 1H), 5.37 (s, 1H), 3.79-3.05 (m, 4H), 2.96-2.83 (m, 4H), 2.69-2.63 (m, 4H), 1.99-1.93 (m, 4H), 1.79-1.70 (m, 4H). | 470.6 |
| 164 | (400 MHz, DMSO-$d_6$) δ 9.12 (s, 1H), 8.60 (dd, J = 4.9, 1.9 Hz, 1H), 8.55 (s, 1H), 8.46-8.40 (m, 1H), 8.30-8.22 (m, 1H), 7.77-7.72 (m, 1H), 7.70-7.64 (m, 1H), 7.40-7.35 (m, 1H), 7.16-7.08 (m, 1H), 7.01 (dd, J = 7.4, 2.2 Hz, 1H), 5.34 (s, 1H), 4.51 (s, 2H), 3.39 (t, J = 6.3 Hz, 3.36-3.27 (m, 4H), 1.94-1.88 (m, 4H), 1.63-1.49 (m, 2H), 0.91 (t, J = 7.4 Hz, 3H). | 445.3 |
| 165 | (400 MHz, DMSO-$d_6$) δ 9.16 (s, 1H), 8.85 (s, 1H), 8.32 (dd, J = 7.4, 0.8 Hz, 1H), 8.25-8.18 (m, 1H), 8.10-8.04 (m, 1H), 7.75-7.69 (m, 1H), 7.65-7.56 (m, 1H), 7.41-7.36 (m, 1H), 7.26-7.19 (m, 1H), 6.78 (dd, J = 7.4, 0.9 Hz, 1H), 5.36 (s, 1H), 3.55-3.36 (m, 4H), 2.67-2.60 (m, 2H), 2.00-1.92 (m, 4H), 1.73-1.60 (m, 2H), 1.41-1.27 (m, 2H), 0.91 (t, J = 7.4 Hz, 3H). | 429.3 |
| 166 | (400 MHz, DMSO-$d_6$) δ 9.19 (s, 1H), 8.83 (s, 1H), 8.33 (dd, J = 7.4, 0.8 Hz, 1H), 8.05-7.99 (m, 2H), 7.75-7.69 (m, 1H), 7.41-7.36 (m, 1H), 7.20-7.12 (m, 1H), 6.66-6.61 (m, 1H), 5.24 (s, 1H), 4.05-3.96 (m, 4H), 2.42-2.31 (m, 5H), 2.23 (s, 3H). | 387.2 |
| 167 | (400 MHz, DMSO-$d_6$) δ 9.19 (s, 1H), 8.92 (s, 1H), 8.33 (dd, J = 7.4, 0.8 Hz, 1H), 8.20-8.13 (m, 1H), 8.08-8.02 (m, 1H), 7.75-7.70 (m, 1H), 7.62-7.53 (m, 1H), 7.42-7.37 (m, 1H), 7.22-7.15 (m, 1H), 6.78 (dd, J = 7.4, 0.9 Hz, 1H), 5.24 (s, 1H), 4.04-3.95 (m, 4H), 2.68-2.59 (m, 2H), 2.42-2.29 (m, 2H), 1.72-1.59 (m, 2H), 1.33 (h, J = 7.3 Hz, 2H), 0.91 (t, J = 7.3 Hz, 3H). | 415.3 |

TABLE 2-31

| | | |
|---|---|---|
| 168 | (400 MHz, DMSO-$d_6$) δ 9.15 (s, 1H), 8.81 (s, 1H), 8.36-8.29 (m, 1H), 8.23-8.16 (m, 1H), 8.08-8.02 (m, 1H), 7.75-7.70 (m, 1H), 7.65-7.56 (m, 1H), 7.42-7.36 (m, 1H), 7.21 (dd, J = 7.4, 2.2 Hz, 1H), 6.78 (dd, J = 7.4, 0.9 Hz, 1H), 5.34 (s, 1H), 3.80-2.95 (m, 4H), 2.68-2.59 (m, 2H), 1.82-1.73 (m, 2H), 1.73-1.60 (m, 2H), 1.41-1.27 (m, 2H), 1.12 (s, 6H), 0.91 (t, J = 7.3 Hz, 3H). | 457.3 |
| 169 | (400 MHz, DMSO-$d_6$) δ 9.16 (s, 1H), 8.84 (s, 1H), 8.33 (dd, J = 7.2, 0.9 Hz, 1H), 8.23-8.16 (m, 1H), 8.09-8.03 (m, 1H), 7.75-7.69 (m, 1H), 7.65-7.56 (m, 1H), 7.43-7.36 (m, 1H), 7.21 (dd, J = 7.4, 2.2 Hz, 1H), 6.78 (dd, J = 7.4, 0.9 Hz, 1H), 5.37 (s, 1H), 3.71-3.51 (m, 4H), 3.51-3.19 (m, 4H), 2.68-2.59 (m, 2H), 1.95-1.86 (m, 2H), 1.71-1.62 (m, 2H), 1.62-1.49 (m, 4H), 1.41-1.27 (m, 2H), 0.91 (t, J = 7.3 Hz, 3H). | 499.3 |
| 170 | (400 MHz, DMSO-$d_6$) δ 9.15 (s, 1H), 8.92 (s, 1H), 8.36-8.27 (m, 2H), 8.12 (dd, J = 5.0, 0.7 Hz, 1H), 8.08-8.03 (m, 1H), 7.75-7.69 (m, 1H), 7.41-7.36 (m, 1H), 7.18 (dd, J = 7.4, 2.2 Hz, 1H), 6.82-6.75 (m, 1H), 5.35 (s, 1H), 3.75-3.07 (m, 4H), 2.60 (q, J = 7.6 Hz, 2H), 1.83-1.75 (m, 2H), 1.17 (t, J = 7.6 Hz, 3H), 1.12 (s, 6H). | 429.3 |
| 171 | (400 MHz, DMSO-$d_6$) δ 9.13 (s, 1H), 8.59-8.53 (m, 2H), 8.36-8.33 (m, 1H), 8.29-8.23 (m, 1H), 7.79-7.72 (m, 1H), 7.70-7.64 (m, 1H), 7.40-7.35 (m, 1H), 7.18-7.10 (m, 1H), 7.06-6.99 (m, 1H), 5.33 (s, 1H), 4.51 (s, 2H), 3.48 (q, J = 7.0 Hz, 2H), 3.33 (s, 4H), 1.95-1.87 (m, 4H), 1.16 (t, J = 7.0 Hz, 3H). | 431.3 |

TABLE 2-31-continued

| 172 | (500 MHz, DMSO-d$_6$) δ 9.16 (s, 1H), 8.85 (s, 1H), 8.35-8.30 (m, 1H), 8.24-8.19 (m, 1H), 8.10-8.05 (m, 1H), 7.74-7.70 (m, 1H), 7.63-7.56 (m, 1H), 7.41-7.36 (m, 1H), 7.21 (dd, J = 7.4, 2.2 Hz, 1H), 6.84-6.79 (m, 1H), 5.36 (s, 1H), 3.61-3.37 (m, 4H), 2.80-2.73 (m, 2H), 2.63-2.56 (m, 2H), 2.18 (s, 6H), 1.99-1.93 (m, 4H). | 444.4 |

TABLE 2-32

| 173 | (400 MHz, DMSO-d$_6$) δ 9.14 (s, 1H), 8.81 (s, 1H), 8.32 (dd, J = 7.4, 0.8 Hz, 1H), 8.22-8.15 (m, 1H), 8.08-8.02 (m, 1H), 7.75-7.69 (m, 1H), 7.64-7.56 (m, 1H), 7.41-7.36 (m, 1H), 7.21 (dd, J = 7.5, 2.2 Hz, 1H), 6.78 (dd, J = 7.4, 0.8 Hz, 1H), 5.34 (s, 1H), 3.76-3.03 (m, 4H), 2.68-2.59 (m, 2H), 1.90-1.82 (m, 2H), 1.73-1.52 (m, 10H), 1.41-1.27 (m, 2H), 0.91 (t, J = 7.4 Hz, 3H). | 483.3 |
| 174 | (400 MHz, DMSO-d$_6$) δ 9.14 (s, 1H), 8.73 (s, 1H), 8.32 (dd, J = 7.4, 0.8 Hz, 1H), 8.10-8.05 (m, 1H), 8.05-7.99 (m, 1H), 7.74-7.69 (m, 1H), 7.41-7.35 (m, 1H), 7.19 (dd, J = 7.4, 2.2 Hz, 1H), 6.66-6.60 (m, 1H), 5.34 (s, 1H), 3.68-3.10 (m, 4H), 2.34 (s, 3H), 2.24 (s, 3H), 1.92-1.83 (m, 2H), 1.72-1.55 (m, 8H). | 455.3 |
| 175 | (400 MHz, DMSO-d$_6$) δ 9.17 (s, 1H), 8.77 (s, 1H), 8.33 (dd, J = 7.3, 0.8 Hz, 1H), 8.12-8.07 (m, 1H), 8.06-8.01 (m, 1H), 7.75-7.69 (m, 1H), 7.41-7.36 (m, 1H), 7.20 (dd, J = 7.5, 2.2 Hz, 1H), 6.67-6.61 (m, 1H), 5.37 (s, 1H), 3.73-3.63 (m, 2H), 3.60-3.51 (m, 2H), 3.50-3.22 (m, 4H), 2.34 (s, 3H), 2.25 (s, 3H), 1.95-1.87 (m, 2H), 1.61-1.53 (m, 4H). | 471.2 |
| 176 | (400 MHz, DMSO-d$_6$) δ 9.16 (s, 1H), 8.73 (s, 1H), 8.33 (dd, J = 7.4, 0.8 Hz, 1H), 8.05-8.03 (m, 1H), 8.02-8.01 (m, 1H), 7.75-7.69 (m, 1H), 7.41-7.35 (m, 1H), 7.18 (dd, J = 7.4, 2.2 Hz, 1H), 6.66-6.60 (m, 1H), 5.36 (s, 1H), 3.67-3.62 (m, 2H), 3.25-3.15 (m, 2H), 2.80-2.71 (m, 2H), 2.34 (s, 3H), 2.24 (s, 3H), 1.90-1.43 (m, 6H). | 441.3 |
| 177 | (400 MHz, DMSO-d$_6$) δ 9.21 (s, 1H), 8.81 (s, 1H), 8.37-8.30 (m, 1H), 8.07-7.99 (m, 2H), 7.76-7.70 (m, 1H), 7.43-7.36 (m, 1H), 7.17 (dd, J = 7.4, 2.2 Hz, 1H), 6.67-6.61 (m, 1H), 5.25 (s, 1H), 3.70 (s, 4H), 2.34 (s, 3H), 2.24 (s, 3H), 1.31 (s, 6H). | 415.2 |

TABLE 2-33

| 178 | (400 MHz, DMSO-d$_6$) δ 9.22 (s, 1H), 8.89 (s, 1H), 8.33 (d, J = 7.4, 0.8 Hz, 1H), 8.06-7.98 (m, 2H), 7.75-7.70 (m, 1H), 7.41-7.36 (m, 1H), 7.16 (dd, J = 7.4, 2.2 Hz, 1H), 6.67-6.62 (m, 1H), 5.26 (s, 1H), 4.75 (s, 4H), 4.17 (s, 4H), 2.34 (s, 3H), 2.26 (s, 3H). | 429.3 |
| 179 | (400 MHz, DMSO-d$_6$) δ 9.15 (s, 1H), 8.81 (s, 1H), 8.36-8.29 (m, 1H), 8.21-8.14 (m, 1H), 8.08-8.02 (m, 1H), 7.75-7.70 (m, 1H), 7.65-7.57 (m, 1H), 7.41-7.36 (m, 1H), 7.21 (dd, J = 7.5, 2.2 Hz, 1H), 6.81-6.74 (m, 1H), 5.36 (s, 1H), 3.69-3.60 (m, 2H), 3.21 (d, J = 10.8 Hz, 2H), 2.83-2.71 (m, 2H), 2.68-2.56 (m, 2H), 1.92-1.28 (m, 10H), 0.91 (t, J = 7.3 Hz, 3H). | 469.4 |
| 180 | (400 MHz, DMSO-d$_6$) δ 9.19 (s, 1H), 8.91 (s, 1H), 8.33 (dd, J = 7.4, 0.8 Hz, 1H), 8.20-8.13 (m, 1H), 8.08-8.03 (m, 1H), 7.75-7.70 (m, 1H), 7.63-7.54 (m, 1H), 7.42-7.36 (m, 1H), 7.20 (dd, J = 7.4, 2.2 Hz, 1H), 6.78 (dd, J = 7.4, 0.8 Hz, 1H), 5.25 (s, 1H), 3.70 (s, 4H), 2.68-2.59 (m, 2H), 1.72-1.60 (m, 2H), 1.41-1.26 (m, 8H), 0.91 (t, J = 7.3 Hz, 3H). | 443.3 |
| 181 | (400 MHz, DMSO-d$_6$) δ 9.22 (s, 1H), 8.98 (s, 1H), 8.33 (dd, J = 7.5, 0.9 Hz, 1H), 8.20-8.13 (m, 1H), 8.09-8.04 (m, 1H), 7.75-7.70 (m, 1H), 7.64-7.55 (m, 1H), 7.42-7.37 (m, 1H), 7.19 (dd, J = 7.4, 2.2 Hz, 1H), 6.83-6.76 (m, 1H), 5.29-5.24 (m, | 457.3 |

TABLE 2-33-continued

|  | 1H), 4.74 (s, 4H), 4.17 (s, 4H), 2.68-2.59 (m, 2H), 1.72-1.60 (m, 2H), 1.41-1.26 (m, 2H), 0.91 (t, J = 7.3 Hz, 3H). | |
| 182 | (400 MHz, DMSO-d$_6$) δ 9.15 (s, 1H), 8.82 (s, 1H), 8.37-8.29 (m, 1H), 8.06-8.00 (m, 1H), 7.92-7.86 (m, 1H), 7.75-7.69 (m, 1H), 7.41-7.36 (m, 1H), 7.13 (dd, J = 7.4, 2.2 Hz, 1H), 6.67-6.61 (m, 1H), 5.63 (s, 1H), 3.59-3.51 (m, 4H), 2.34 (s, 3H), 2.23 (s, 3H), 1.41-1.33 (m, 4H), 0.99 (s, 6H). | 443.3 |

TABLE 2-34

| 183 | (400 MHz, DMSO-d$_6$) δ 9.15 (s, 1H), 8.82 (s, 1H), 8.37-8.29 (m, 1H), 8.05-7.99 (m, 1H), 7.91-7.86 (m, 1H), 7.75-7.70 (m, 1H), 7.41-7.36 (m, 1H), 7.12 (dd, J = 7.4, 2.2 Hz, 1H), 6.67-6.61 (m, 1H), 5.63 (s, 1H), 4.27-4.18 (m, 1H), 2.94-2.82 (m, 2H), 2.34 (s, 3H), 2.23 (s, 3H), 1.73-1.59 (m, 3H), 1.18-1.04 (m, 2H), 0.93 (d, J = 6.0 Hz, 3H). | 429.3 |
| 184 | (400 MHz, DMSO-d$_6$) δ 9.15 (s, 1H), 8.85 (s, 1H), 8.37-8.29 (m, 1H), 8.07-8.01 (m, 1H), 7.93-7.88 (m, 1H), 7.75-7.69 (m, 1H), 7.41-7.36 (m, 1H), 7.14 (dd, J = 7.4, 2.2 Hz, 1H), 6.67-6.62 (m, 1H), 5.62 (s, 1H), 4.22-4.06 (m, 2H), 2.93-2.81 (m, 1H), 2.61-2.52 (m, 1H), 2.34 (s, 3H), 2.24 (s, 3H), 1.87-1.37 (m, 4H), 1.26-1.10 (m, 1H), 0.93 (d, J = 6.6 Hz, 3H). | 429.3 |
| 185 | (400 MHz, DMSO-d$_6$) δ 9.22 (s, 1H), 8.83 (s, 1H), 8.37-8.30 (m, 1H), 8.07-8.01 (m, 2H), 7.75-7.70 (m, 1H), 7.43-7.34 (m, 1H), 7.23-7.16 (m, 1H), 6.67-6.62 (m, 1H), 5.58-5.33 (m, 2H), 3.84-3.41 (m, 4H), 2.35 (s, 3H), 2.32-2.07 (m, 5H). | 419.5 |
| 186 | (400 MHz, DMSO-d$_6$) δ 9.22 (s, 1H), 8.84 (s, 1H), 8.34 (dd, J = 7.3, 0.8 Hz, 1H), 8.07-8.01 (m, 2H), 7.75-7.70 (m, 1H), 7.42-7.36 (m, 1H), 7.20 (dd, J = 7.4, 2.2 Hz, 1H), 6.67-6.62 (m, 1H), 5.57-5.34 (m, 2H), 3.88-3.39 (m, 4H), 2.39-2.07 (m, 8H). | 419.4 |
| 187 | (500 MHz, DMSO-d$_6$) δ 9.36 (s, 1H), 8.74 (s, 1H), 8.42-8.37 (m, 1H), 8.15-8.11 (m, 1H), 7.93-7.89 (m, 1H), 7.82-7.78 (m, 1H), 7.53-7.47 (m, 1H), 7.28-7.22 (m, 1H), 6.68-6.62 (m, 1H), 5.65 (s, 1H), 3.59-3.49 (m, 4H), 2.59 (t, J = 7.7 Hz, 2H), 2.24 (s, 3H), 1.72-1.52 (m, 8H), 1.39-1.28 (m, 2H), 0.91 (t, J = 7.4 Hz, 3H). | 457.1 |

TABLE 2-35

| 188 | (500 MHz, DMSO-d$_6$) δ 9.20 (s, 1H), 8.73 (s, 1H), 8.38-8.33 (m, 1H), 8.08-8.04 (m, 1H), 7.98-7.90 (m, 1H), 7.77-7.72 (m, 1H), 7.44-7.39 (m, 1H), 7.16 (dd, J = 7.5, 2.2 Hz, 1H), 6.64-6.58 (m, 1H), 5.63 (s, 1H), 3.58-3.49 (m, 4H), 2.46 (d, J = 7.1 Hz, 2H), 2.25 (s, 3H), 2.13-2.01 (m, 1H), 1.70-1.52 (m, 6H), 0.90 (d, J = 6.6 Hz, 6H). | 457.2 |
| 189 | (500 MHz, DMSO-d$_6$) δ 9.38 (s, 1H), 8.74 (s, 1H), 8.44-8.37 (m, 1H), 8.15-8.10 (m, 1H), 7.93-7.89 (m, 1H), 7.82-7.76 (m, 1H), 7.51-7.47 (m, 1H), 7.25 (dd, J = 7.4, 2.1 Hz, 1H), 6.66 (s, 1H), 5.66 (s, 1H), 3.59-3.53 (m, 4H), 2.62 (q, J = 7.6 Hz, 2H), 2.25 (s, 3H), 1.70-1.52 (m, 6H), 1.22 (t, J = 7.5 Hz, 3H). | 429.1 |
| 190 | (500 MHz, DMSO-d$_6$) δ 9.78 (s, 1H), 8.92 (s, 1H), 8.51-8.47 (m, 1H), 8.33-8.29 (m, 1H), 7.95-7.91 (m, 1H), 7.75-7.71 (m, 1H), 7.70-7.66 (m, 1H), 7.58-7.52 (m, 1H), 6.46-6.41 (m, 1H), 5.72 (s, 1H), 3.77 (s, 3H), 3.61-3.55 (m, 4H), 2.33 (s, 3H), 1.70-1.50 (m, 6H). | 431.0 |
| 191 | (500 MHz, DMSO-d$_6$) δ 9.91 (s, 1H), 9.14 (s, 1H), 8.70-7.58 (m, 6H), 6.68-6.63 (m, 1H), 5.75 (s, 1H), 5.34 (d, J = 47.0 Hz, 2H), 3.83 (s, 3H), 3.63-3.57 (m, 4H), 1.71-1.52 (m, 6H). | 449.0 |
| 192 | (400 MHz, Chloroform-d) δ 9.43 (s, 1H), 8.76 (s, 1H), 8.35-8.28 (m, 1H), 8.04-7.96 (m, 1H), 7.88-7.81 (m, 1H), 7.57-7.49 (m, 2H), 7.50-7.42 (m, | 417.3 |

TABLE 2-35-continued

| | | |
|---|---|---|
| | 1H), 7.10 (dd, J = 7.5, 4.9 Hz, 1H), 6.86 (dd, J = 7.3, 2.2 Hz, 1H), 5.67 (s, 1H), 4.67 (s, 2H), 3.43-3.35 (m, 4H), 1.60-1.45 (m, 6H). | |

TABLE 2-36

| | | |
|---|---|---|
| 193 | (500 MHz, DMSO-$d_6$) δ 9.13 (s, 1H), 8.70 (s, 1H), 8.33 (dd, J = 7.4, 0.8 Hz, 1H), 8.10-8.06 (m, 1H), 8.03-7.99 (m, 1H), 7.74-7.70 (m, 1H), 7.41-7.36 (m, 1H), 7.18 (dd, J = 7.3, 2.2 Hz, 1H), 6.65-6.61 (m, 1H), 5.33 (s, 1H), 3.12-2.81 (m, 4H), 2.34 (s, 3H), 2.24 (s, 3H), 1.87-1.83 (m, 2H), 1.08 (d, J = 5.8 Hz, 6H). | 429.1 |
| 194 | (500 MHz, DMSO-$d_6$) δ 9.19 (s, 1H), 8.76 (s, 1H), 8.36-8.31 (m, 1H), 8.05-8.00 (m, 2H), 7.75-7.70 (m, 1H), 7.41-7.37 (m, 1H), 7.19 (dd, J = 7.4, 2.2 Hz, 1H), 6.66-6.62 (m, 1H), 5.37 (s, 1H), 4.41-4.17 (m, 2H), 3.91-3.39 (m, 8H), 2.34 (s, 3H), 2.24 (s, 3H). | 459.0 |
| 195 | (500 MHz, DMSO-$d_6$) δ 9.27 (s, 1H), 9.11 (s, 1H), 9.04 (s, 1H), 8.39-8.34 (m, 1H), 8.01-7.97 (m, 1H), 7.94-7.90 (m, 1H), 7.74 (s, 1H), 7.68-7.62 (m, 2H), 7.42-7.38 (m, 1H), 7.35-7.26 (m, 2H), 7.15 (dd, J = 7.4, 2.1 Hz, 1H), 7.02-6.95 (m, 1H), 6.65 (s, 1H), 5.82 (s, 1H), 2.36 (s, 3H), 2.20 (s, 3H). | 423.0 |
| 196 | (500 MHz, DMSO-$d_6$) δ 9.08 (s, 1H), 8.64 (s, 1H), 8.32 (dd, J = 7.3, 0.9 Hz, 1H), 7.97-7.91 (m, 2H), 7.73-7.69 (m, 1H), 7.48-7.44 (m, 1H), 7.40-7.30 (m, 5H), 7.27-7.19 (m, 1H), 7.14 (dd, J = 7.5, 2.2 Hz, 1H), 6.62-6.58 (m, 1H), 5.51 (s, 1H), 4.53 (s, 2H), 2.32 (s, 3H), 2.14 (s, 3H). | 437.1 |
| 197 | (500 MHz, DMSO-$d_6$) δ 9.49 (s, 1H), 8.89 (s, 1H), 8.45-8.40 (m, 1H), 8.25-8.21 (m, 1H), 7.88-7.84 (m, 1H), 7.77-7.72 (m, 1H), 7.59-7.55 (m, 1H), 7.42-7.38 (m, 1H), 6.42-6.38 (m, 1H), 5.67 (s, 1H), 3.76 (s, 3H), 3.63-3.55 (m, 4H), 2.60-2.53 (m, 2H), 1.70-1.52 (m, 8H), 1.39-1.27 (m, 2H), 0.91 (t, J = 7.4 Hz, 3H). | 473.1 |

TABLE 2-37

| | | |
|---|---|---|
| 198 | (500 MHz, DMSO-$d_6$) δ 9.24 (s, 1H), 8.58 (s, 1H), 8.33 (dd, J = 7.4, 0.8 Hz, 1H), 8.05-8.01 (m, 1H), 8.01-7.95 (m, 1H), 7.74-7.69 (m, 1H), 7.69-7.63 (m, 1H), 7.40-7.35 (m, 1H), 7.16 (dd, J = 7.4, 2.2 Hz, 1H), 6.66-6.60 (m, 1H), 5.83 (s, 1H), 3.04-2.40 (m, 4H), 2.34 (s, 3H), 2.26 (s, 3H), 1.74-1.52 (m, 6H). | 430.1 |
| 199 | (500 MHz, DMSO-$d_6$) δ 9.27 (s, 1H), 8.66 (s, 1H), 8.33 (dd, J = 7.4, 0.8 Hz, 1H), 8.06-8.02 (m, 1H), 8.00-7.96 (m, 1H), 7.82-7.78 (m, 1H), 7.74-7.69 (m, 1H), 7.40-7.36 (m, 1H), 7.16 (dd, J = 7.5, 2.2 Hz, 1H), 6.67-6.61 (m, 1H), 5.88 (s, 1H), 3.69 (s, 4H), 2.82-2.78 (m, 4H), 2.34 (s, 3H), 2.26 (s, 3H). | 432.1 |
| 200 | (500 MHz, DMSO-$d_6$) δ 10.00 (s, 1H), 9.31 (s, 1H), 9.09-9.05 (m, 1H), 8.34-8.29 (m, 1H), 8.09-8.04 (m, 1H), 7.93-7.89 (m, 1H), 7.74-7.70 (m, 1H), 7.41-7.37 (m, 1H), 7.14 (dd, J = 7.4, 2.2 Hz, 1H), 6.91-6.85 (m, 2H), 6.66-6.62 (m, 1H), 6.16-6.11 (m, 2H), 5.06 (s, 1H), 2.34 (s, 3H), 2.23 (s, 3H). | 411.9 |
| 201 | (500 MHz, DMSO-$d_6$) δ 9.14 (s, 1H), 8.81 (s, 1H), 8.37-8.30 (m, 1H), 8.06-8.01 (m, 1H), 7.97-7.88 (m, 1H), 7.75-7.71 (m, 1H), 7.40-7.36 (m, 1H), 7.17 (dd, J = 7.5, 2.2 Hz, 1H), 6.69-6.61 (m, 1H), 5.61 (s, 1H), 3.59-3.49 (m, 4H), 2.64-2.52 (m, 4H), 1.70-1.51 (m, 8H), 1.41-1.28 (m, 2H), 1.12 (t, J = 7.6 Hz, 3H), 0.91 (t, J = 7.5 Hz, 3H). | 471.1 |

TABLE 2-37-continued

| | | |
|---|---|---|
| 202 | (500 MHz, DMSO-$d_6$) δ 9.21 (s, 1H), 9.15 (s, 1H), 8.38-8.32 (m, 1H), 8.08-8.04 (m, 1H), 8.04-7.97 (m, 1H), 7.76-7.72 (m, 1H), 7.59-7.52 (m, 1H), 7.45-7.40 (m, 1H), 7.18 (dd, J = 7.6, 2.3 Hz, 1H), 5.63 (s, 1H), 3.56-3.50 (m, 4H), 2.38 (d, J = 2.9 Hz, 3H), 1.70-1.48 (m, 6H). | 419.0 |

TABLE 2-38

| | | |
|---|---|---|
| 203 | (500 MHz, DMSO-$d_6$) δ 9.31 (s, 1H), 9.22 (s, 1H), 8.38-8.33 (m, 1H), 8.09-8.03 (m, 2H), 7.77-7.74 (m, 1H), 7.74-7.70 (m, 1H), 7.43 (s, 1H), 7.21-7.16 (m, 1H), 5.65 (s, 1H), 3.56-3.50 (m, 4H), 2.47 (s, 3H), 1.71-1.50 (m, 6H). | 434.9 |
| 204 | (400 MHz, DMSO-$d_6$) δ 9.36 (s, 1H), 9.12 (s, 1H), 8.43-8.36 (m, 1H), 8.18-8.15 (m, 1H), 8.15-8.12 (m, 1H), 8.11-8.07 (m, 1H), 7.81-7.76 (m, 1H), 7.53-7.46 (m, 1H), 7.22-7.14 (m, 1H), 5.66 (s, 1H), 3.61-3.51 (m, 4H), 2.24 (s, 3H), 1.74-1.50 (m, 6H). | 419.0 |
| 205 | (500 MHz, DMSO-$d_6$) δ 9.50 (s, 1H), 9.20 (s, 1H), 8.36-8.31 (m, 1H), 8.21-8.17 (m, 1H), 8.00-7.95 (m, 1H), 7.75-7.71 (m, 1H), 7.41-7.37 (m, 1H), 7.22 (dd, J = 7.4, 2.1 Hz, 1H), 6.93-6.89 (m, 1H), 5.65 (s, 1H), 3.58-3.49 (m, 4H), 2.39 (s, 3H), 1.71-1.50 (m, 6H). | 435.1 |
| 206 | (500 MHz, DMSO-$d_6$) δ 9.32 (s, 1H), 8.60 (s, 1H), 8.38-8.33 (m, 1H), 8.10-8.06 (m, 1H), 8.04-7.97 (m, 1H), 7.77-7.70 (m, 1H), 7.69-7.65 (m, 1H), 7.45-7.41 (m, 1H), 7.22-7.16 (m, 1H), 6.63 (s, 1H), 5.88 (s, 1H), 2.88-2.84 (m, 4H), 2.34 (s, 3H), 2.26 (s, 3H), 1.81-1.75 (m, 4H). | 416.1 |
| 207 | (400 MHz, DMSO-$d_6$) δ 9.16 (s, 1H), 9.05 (s, 1H), 8.32 (dd, J = 7.5, 0.8 Hz, 1H), 8.17-8.11 (m, 1H), 8.08-8.06 (m, 1H), 8.06-8.02 (m, 1H), 7.75-7.69 (m, 1H), 7.41-7.36 (m, 1H), 7.22 (dd, J = 7.4, 2.2 Hz, 1H), 6.50 (dd, J = 5.7, 2.4 Hz, 1H), 5.36 (s, 1H), 3.81 (s, 3H), 3.66-3.21 (m, 4H), 1.97-1.50 (m, 10H). | 457.5 |

TABLE 2-39

| | | |
|---|---|---|
| 208 | (400 MHz, DMSO-$d_6$) δ 9.19 (s, 1H), 8.92 (s, 1H), 8.36-8.32 (m, 1H), 8.32-8.28 (m, 1H), 8.15-8.10 (m, 1H), 8.10-8.06 (m, 1H), 7.76-7.71 (m, 1H), 7.43-7.38 (m, 1H), 7.21 (dd, J = 7.5, 2.2 Hz, 1H), 6.79 (dd, J = 5.1, 1.5 Hz, 1H), 5.36 (s, 1H), 3.64-3.19 (m, 4H), 2.60 (q, J = 7.6 Hz, 2H), 1.95-1.51 (m, 10H), 1.17 (t, J = 7.6 Hz, 3H). | 455.5 |
| 209 | (400 MHz, DMSO-$d_6$) δ 9.18 (s, 1H), 9.02 (s, 1H), 8.35-8.28 (m, 1H), 8.16-8.10 (m, 1H), 8.07-8.05 (m, 1H), 8.05-8.03 (m, 1H), 7.75-7.69 (m, 1H), 7.41-7.36 (m, 1H), 7.22 (dd, J = 7.4, 2.2 Hz, 1H), 6.51 (dd, J = 5.8, 2.4 Hz, 1H), 5.36 (s, 1H), 3.81 (s, 3H), 3.67-3.19 (m, 4H), 1.82-1.74 (m, 2H), 1.11 (s, 6H). | 431.4 |
| 210 | (500 MHz, DMSO-$d_6$) δ 9.56 (s, 1H), 9.20 (s, 1H), 8.37-8.31 (m, 1H), 8.09-8.05 (m, 1H), 8.04-8.02 (m, 1H), 7.75-7.71 (m, 1H), 7.41-7.37 (m, 1H), 7.11 (dd, J = 7.4, 2.1 Hz, 1H), 6.87-6.83 (m, 1H), 5.65 (s, 1H), 3.58-3.52 (m, 4H), 2.27 (s, 3H), 1.73-1.46 (m, 6H). | 434.9 |
| 211 | (400 MHz, DMSO-$d_6$) δ 9.15 (s, 1H), 8.90 (s, 1H), 8.34 (dd, J = 7.4, 0.8 Hz, 1H), 8.08-7.99 (m, 2H), 7.75-7.70 (m, 1H), 7.65-7.56 (m, 1H), 7.42-7.37 (m, 1H), 7.16 (dd, J = 7.4, 2.2 Hz, 1H), 6.76 (dd, J = 7.4, 0.8 Hz, 1H), 5.62 (s, 1H), 3.58-3.50 (m, 4H), 2.55-2.49 (m, 2H), 2.16-2.01 (m, 1H), 1.69-1.50 (m, 6H), 0.90 (d, J = 6.6 Hz, 6H). | 443.5 |

TABLE 2-39-continued

| | | |
|---|---|---|
| 212 | (500 MHz, DMSO-$d_6$) δ 9.62 (s, 1H), 8.67 (s, 1H), 8.48-8.43 (m, 1H), 8.31-8.27 (m, 1H), 8.14-8.10 (m, 1H), 7.91-7.87 (m, 1H), 7.65-7.61 (m, 1H), 7.48-7.42 (m, 1H), 6.65-6.61 (m, 1H), 5.42 (s, 1H), 3.75-3.08 (m, 4H), 2.46 (d, J = 7.2 Hz, 2H), 2.27 (s, 3H), 2.11-2.02 (m, 1H), 2.01-1.96 (m, 4H), 0.90 (d, J = 6.6 Hz, 6H). | 443.3 |

TABLE 2-40

| | | |
|---|---|---|
| 213 | (500 MHz, DMSO-$d_6$) δ 9.61 (s, 1H), 8.66 (s, 1H), 8.48-8.43 (m, 1H), 8.30-8.26 (m, 1H), 8.13-8.09 (m, 1H), 7.90-7.86 (m, 1H), 7.64-7.60 (m, 1H), 7.47-7.41 (m, 1H), 6.65-6.61 (m, 1H), 5.40 (s, 1H), 3.92-2.96 (m, 4H), 2.46 (d, J = 7.2 Hz, 2H), 2.27 (s, 3H), 2.11-2.02 (m, 1H), 1.83-1.76 (m, 2H), 1.13 (s, 6H), 0.90 (d, J = 6.6 Hz, 6H). | 471.4 |
| 214 | (500 MHz, DMSO-$d_6$) δ 9.44 (s, 1H), 8.67 (s, 1H), 8.43-8.38 (m, 1H), 8.21-8.17 (m, 1H), 8.12-8.08 (m, 1H), 7.84-7.80 (m, 1H), 7.55-7.51 (m, 1H), 7.37-7.31 (m, 1H), 6.68-6.64 (m, 1H), 5.40 (s, 1H), 3.69-3.21 (m, 4H), 2.62 (q, J = 7.5 Hz, 2H), 2.26 (s, 3H), 2.00-1.94 (m, 4H), 1.22 (t, J = 7.6 Hz, 3H). | 415.3 |
| 215 | (500 MHz, DMSO-$d_6$) δ 9.46 (s, 1H), 8.65 (s, 1H), 8.44-8.39 (m, 1H), 8.21-8.17 (m, 1H), 8.11-8.07 (m, 1H), 7.85-7.81 (m, 1H), 7.56-7.52 (m, 1H), 7.40-7.28 (m, 1H), 6.69-6.65 (m, 1H), 5.38 (s, 1H), 3.78-3.10 (m, 4H), 2.62 (q, J = 7.5 Hz, 2H), 2.26 (s, 3H), 1.82-1.76 (m, 2H), 1.22 (t, J = 7.6 Hz, 3H), 1.12 (s, 6H). | 443.3 |
| 216 | (400 MHz, DMSO-$d_6$) δ 9.15 (s, 1H), 8.81 (s, 1H), 8.32 (dd, J = 7.4, 0.8 Hz, 1H), 8.24-8.17 (m, 1H), 8.07-8.02 (m, 1H), 7.75-7.69 (m, 1H), 7.65-7.56 (m, 1H), 7.41-7.36 (m, 1H), 7.22 (dd, J = 7.4, 2.2 Hz, 1H), 6.75 (dd, J = 7.3, 0.9 Hz, 1H), 5.34 (s, 1H), 3.85-2.84 (m, 4H), 2.56-2.44 (m, 2H), 2.16-2.01 (m, 1H), 1.82-1.73 (m, 2H), 1.12 (s, 6H), 0.90 (d, J = 6.6 Hz, 6H). | 457.5 |
| 217 | (400 MHz, DMSO-$d_6$) δ 9.14 (s, 1H), 8.81 (s, 1H), 8.36-8.29 (m, 1H), 8.24-8.17 (m, 1H), 8.08-8.02 (m, 1H), 7.75-7.69 (m, 1H), 7.65-7.56 (m, 1H), 7.41-7.36 (m, 1H), 7.21 (dd, J = 7.4, 2.2 Hz, 1H), 6.75 (dd, J = 7.4, 0.9 Hz, 1H), 5.34 (s, 1H), 3.85-2.87 (m, 4H), 2.59-2.44 (m, 2H), 2.16-2.01 (m, 1H), 1.91-1.82 (m, 2H), 1.71-1.54 (m, 8H), 0.90 (d, J = 6.6 Hz, 6H). | 483.6 |

TABLE 2-41

| | | |
|---|---|---|
| 218 | (400 MHz, DMSO-$d_6$) δ 9.14 (s, 1H), 8.81 (s, 1H), 8.33 (dd, J = 7.4, 0.8 Hz, 1H), 8.20 (dd, J = 8.4, 0.9 Hz, 1H), 8.08-8.02 (m, 1H), 7.75-7.70 (m, 1H), 7.65-7.56 (m, 1H), 7.43-7.36 (m, 1H), 7.21 (dd, J = 7.5, 2.2 Hz, 1H), 6.75 (dd, J = 7.3, 0.9 Hz, 1H), 5.33 (s, 1H), 4.04-3.38 (m, 2H), 3.12-2.77 (m, 2H), 2.59-2.41 (m, 2H), 2.16-2.01 (m, 1H), 1.96-1.71 (m, 2H), 1.12-1.01 (m, 6H), 0.90 (d, J = 6.6 Hz, 6H). | 457.5 |
| 219 | (400 MHz, DMSO-$d_6$) δ 9.14 (s, 1H), 9.04 (s, 1H), 8.32 (dd, J = 7.4, 0.8 Hz, 1H), 8.20-8.14 (m, 1H), 8.07-8.05 (m, 1H), 8.05-8.02 (m, 1H), 7.75-7.69 (m, 1H), 7.41-7.36 (m, 1H), 7.22 (dd, J = 7.5, 2.2 Hz, 1H), 6.50 (dd, J = 5.7, 2.4 Hz, 1H), 5.34 (s, 1H), 4.27-2.77 (m, 7H), 1.96-1.77 (m, 2H), 1.06 (d, J = 5.4 Hz, 6H). | 431.4 |
| 220 | (400 MHz, DMSO-$d_6$) δ 9.13 (s, 1H), 8.92 (s, 1H), 8.36-8.29 (m, 2H), 8.16-8.09 (m, 1H), 8.08-8.02 (m, 1H), 7.75-7.69 (m, 1H), 7.41-7.36 (m, 1H), 7.18 (dd, J = 7.4, 2.2 Hz, 1H), 6.78 (dd, J = 5.1, 1.5 Hz, 1H), 5.34 (s, 1H), 4.23-2.77 (m, 4H), 2.60 (q, J = 7.6 Hz, 2H), 1.94-1.73 (m, 2H), 1.17 (t, J = 7.6 Hz, 3H), 1.07 (d, J = 5.9 Hz, 6H). | 429.5 |
| 221 | (500 MHz, DMSO-$d_6$) δ 9.23 (s, 1H), 8.90 (s, 1H), 8.38-8.28 (m, 1H), 8.11-8.04 (m, 1H), 8.02-7.89 (m, 1H), 7.81-7.69 (m, 1H), 7.49-7.38 (m, 1H), 7.36-7.26 (m, 1H), 6.46-6.36 (m, 1H), 5.37 (s, 1H), 3.78 (s, 3H), 3.63-3.37 (m, 4H), 2.32 (s, 3H), 2.03-1.91 (m, 4H). | 416.8 |
| 222 | (500 MHz, DMSO-$d_6$) δ 15.28-14.93 (m, 1H), 13.60-13.28 (m, 1H), 11.63-11.25 (m, 1H), 10.59-10.33 (m, 1H), 8.85-8.65 (m, 1H), 8.17-8.13 (m, 1H), 8.13-8.07 (m, 1H), 8.01-7.95 (m, 1H), 7.90-7.84 (m, 1H), 7.00-6.93 (m, 1H), 6.92-6.83 (m, 1H), 5.81-5.62 (m, 1H), 3.99 (s, 3H), 3.89-3.74 (m, 1H), 3.56-3.46 (m, 2H), 3.20-3.09 (m, 1H), 2.56 (s, 3H), 1.92-1.77 (m, 2H), 1.15 (s, 6H). | 444.9 |

Test Example 1: In Vitro Antimalarial Assay

For the evaluation of the antimalarial activity of the compound of the present invention, K1 strain, a drug resistant strain of *Plasmodium falciparum*, and FCR3 strain, a drug sensitive strain thereof, which were generous gift from Professor Kiyoshi Kita of the Graduate School of Medicine and Faculty of Medicine, the University of Tokyo, were used to measure the in vitro antimalarial activity of the compound against those *Plasmodium* species according to the method established by Otoguro et al. (Otoguro, K., Kohana, A., Manabe, C., Ishiyama, A., Ui, H., Shiomi, K., Yamada, H. & Omura, S.: Potent antimalarial activity of polyether antibiotic, X-206. J. Antibiot., 54: 658-663, (2001)).

The parasites were grown based on a slightly modified method from the original method reported by Trager and Jensen (Trager, W. and Jensen, J.: Human malaria parasites in continuous culture, Science, 193: 673-677, (1976)), and those which were maintained and sub-cultured by the method were used. More specifically, in a culture dish, erythrocytes infected with the protozoa, which had been sub-cultured using a RPMI 1640 medium to which 10% human plasma had been added and fresh human erythrocytes, were diluted (hematocrit value: 2 to 5%, parasitaemia: 0.25 to 1%), and were cultured at 37° C. in a mixed gas of 3% $O_2$-4% $CO_2$-93% $N_2$, and continuously cultured while changing the medium and adding fresh erythrocytes at 2- or 3-day intervals.

A drug susceptibility test was performed by modifying the method established by Desjardins et al. (Desjardins, R. E., Canfield, C. J., Haynes, D. E. and Chulay, J. D.: Quantitative assessment of antimalarial activity in vitro by a semiautomated microdilution technique. Antimicrob. Agents Chemother., 16: 710-718 (1979)). More specifically, 190 µL of a suspension of protozoa which had been precultured (hematocrit value: 2%, parasitaemia: 0.5 or 1%) and 10 µL of a solution of a test compound (5% DMSO solution) serially diluted so that the final concentration was 12.5 to 0.0001 µM were put in each well of a 96-well plate, and after mixing, the same was cultured for 72 hours in the above mixed gas.

For the measurement of the growth of protozoa, the method established by Makler (Makler, M. T., Rise, J. M., Williams, J. A., Bancroft, J. E., Piper, R. C., Gibbins, B. L. and Hinrichs, D. J.: Parasite lactate dehydrogenase as an Assay for *Plasmodium falciparum* drug sensitivity, Am. J. Med. Hyg., 48: 739-741 (1993)) was modified to colorimetrically determine parasite lactate dehydrogenase (p-LDH) using Malstat reagent (Flow Inc., USA).

More specifically, 72 hours after the culture, the 96-well plate was directly frozen at −20° C. for 18 hours and melted at 37° C. to hemolyze the protozoan-infected erythrocytes and destroy the protozoa to prepare a crude enzyme solution.

100 μL of Malstat reagent and 20 μL of the crude enzyme solution were added to and mixed in each well of another 96-well plate, and after reacting for 15 minutes at room temperature, 20 μL of a nitroblue tetrazolium 2 mg/mL phenazine ethosulfate 0.1 mg/mL=1:1 solution was added to the respective wells, and reaction was performed in dark conditions at room temperature for 2 hours.

The absorbance of the blue formazan product formed by the reaction was measured at a measurement wavelength of 655 nm by using a microplate reader (Labsystems, Finland) to colorimetrically determine the growth of the protozoa. The 50% growth inhibitory concentration for the protozoa of the compound ($IC_{50}$ value) was determined based on the concentration-response curve of the compound.

(Results of Evaluation)

The compounds of the present invention showed a potent antimalarial activity in the test for in vitro antimalarial activity. The antimalarial activity of the representative compounds of the present invention against cultured *Plasmodium falciparum* is shown in [Table 3-1] to [Table 3-8]. The antimalarial activity is represented by symbol * when the $IC_{50}$ value is less than 0.1 μM, symbol  when 0.1 μM or more and less than 1 μM, and symbol * when 1 μM or more and less than 10 μM. In the case where the test was not performed, NT (Not Tested) is shown.

TABLE 3-1

| Tested Compound Example No. | Strain K1 | Strain FCR3 |
| --- | --- | --- |
| 1 | *** | *** |
| 2 | *** | *** |
| 3 | * | NT |
| 4 | ** | ** |
| 5 | * | * |
| 6 | ** | ** |
| 7 | *** | *** |
| 8 | * | ** |
| 9 | ** | *** |
| 10 | *** | *** |
| 11 | * | ** |
| 12 | ** | ** |
| 13 | ** | *** |
| 14 | * | ** |
| 15 | *** | *** |
| 16 | * | NT |
| 17 | *** | *** |
| 18 | *** | *** |
| 19 | ** | ** |
| 20 | ** | ** |
| 21 | ** | ** |
| 22 | ** | ** |
| 23 | * | ** |
| 24 | * | NT |
| 25 | * | * |
| 26 | *** | *** |
| 27 | ** | * |

TABLE 3-2

| | | |
| --- | --- | --- |
| 28 | *** | *** |
| 29 | ** | ** |
| 30 | *** | *** |
| 31 | ** | ** |
| 32 | *** | *** |
| 33 | ** | *** |
| 34 | *** | ** |
| 35 | * | * |
| 36 | * | * |
| 37 | * | * |
| 38 | ** | ** |
| 39 | * | * |

TABLE 3-2-continued

| | | |
| --- | --- | --- |
| 40 | * | * |
| 41 | ** | *** |
| 42 | ** | ** |
| 43 | ** | *** |
| 44 | *** | *** |
| 45 | * | *** |
| 46 | ** | *** |
| 47 | ** | *** |
| 48 | *** | *** |
| 49 | * | ** |
| 50 | *** | *** |
| 51 | * | ** |
| 52 | * | NT |
| 53 | ** | ** |
| 54 | *** | *** |
| 55 | * | ** |
| 56 | * | NT |
| 57 | * | ** |

TABLE 3-3

| | | |
| --- | --- | --- |
| 58 | *** | *** |
| 59 | * | NT |
| 60 | *** | *** |
| 61 | * | ** |
| 62 | ** | ** |
| 63 | ** | ** |
| 64 | ** | *** |
| 65 | ** | ** |
| 66 | ** | ** |
| 67 | ** | ** |
| 68 | *** | *** |
| 69 | ** | *** |
| 70 | *** | *** |
| 71 | *** | *** |
| 72 | * | ** |
| 73 | ** | ** |
| 74 | ** | *** |
| 75 | ** | *** |
| 76 | * | NT |
| 77 | ** | *** |
| 78 | ** | *** |
| 79 | ** | ** |
| 80 | ** | ** |
| 81 | ** | ** |
| 82 | ** | ** |
| 83 | * | ** |
| 84 | *** | *** |
| 85 | * | * |

TABLE 3-4

| | | |
| --- | --- | --- |
| 86 | ** | ** |
| 87 | *** | *** |
| 88 | *** | *** |
| 89 | ** | *** |
| 90 | ** | *** |
| 91 | ** | *** |
| 92 | *** | *** |
| 93 | *** | *** |
| 94 | *** | *** |
| 95 | *** | *** |
| 96 | ** | ** |
| 97 | ** | ** |
| 98 | ** | ** |
| 99 | ** | ** |
| 100 | ** | ** |
| 101 | * | ** |
| 102 | ** | ** |
| 103 | ** | ** |
| 104 | * | ** |
| 105 | *** | *** |
| 106 | *** | *** |
| 107 | *** | *** |
| 108 | ** | *** |

TABLE 3-4-continued

| | | |
|---|---|---|
| 109 | *** | *** |
| 110 | ** | *** |
| 111 | *** | *** |
| 112 | *** | *** |
| 113 | *** | *** |
| 114 | *** | *** |

TABLE 3-5

| | | |
|---|---|---|
| 115 | *** | *** |
| 116 | *** | *** |
| 117 | *** | *** |
| 118 | *** | *** |
| 119 | *** | *** |
| 120 | * | * |
| 121 | ** | *** |
| 122 | ** | ** |
| 123 | ** | *** |
| 124 | ** | ** |
| 125 | *** | *** |
| 126 | *** | *** |
| 127 | *** | *** |
| 128 | *** | *** |
| 129 | *** | *** |
| 130 | *** | *** |
| 131 | *** | *** |
| 132 | *** | *** |
| 133 | *** | *** |
| 134 | *** | *** |
| 135 | *** | *** |
| 136 | *** | *** |
| 137 | *** | *** |
| 138 | ** | *** |
| 139 | *** | *** |

TABLE 3-6

| | | |
|---|---|---|
| 140 | *** | *** |
| 141 | ** | *** |
| 142 | *** | *** |
| 143 | ** | * |
| 144 | ** | ** |
| 145 | ** | *** |
| 146 | *** | *** |
| 147 | *** | *** |
| 148 | *** | *** |
| 149 | *** | *** |
| 150 | ** | *** |
| 151 | ** | ** |
| 152 | *** | *** |
| 153 | *** | *** |
| 154 | *** | *** |
| 155 | *** | *** |
| 156 | ** | *** |
| 157 | *** | *** |
| 158 | ** | *** |
| 159 | *** | *** |
| 160 | *** | *** |
| 161 | *** | *** |
| 162 | ** | *** |
| 163 | ** | *** |
| 164 | * | ** |
| 165 | *** | *** |
| 166 | *** | *** |
| 167 | ** | *** |
| 168 | ** | *** |

TABLE 3-7

| | | |
|---|---|---|
| 169 | *** | *** |
| 170 | *** | *** |
| 171 | ** | ** |
| 172 | ** | *** |

TABLE 3-7-continued

| | | |
|---|---|---|
| 173 | ** | ** |
| 174 | *** | *** |
| 175 | *** | *** |
| 176 | *** | *** |
| 177 | *** | *** |
| 178 | *** | *** |
| 179 | ** | ** |
| 180 | *** | *** |
| 181 | *** | ** |
| 182 | ** | ** |
| 183 | ** | ** |
| 184 | ** | ** |
| 185 | *** | *** |
| 186 | *** | *** |
| 187 | ** | ** |
| 188 | *** | *** |
| 189 | *** | *** |
| 190 | *** | *** |
| 191 | ** | ** |
| 192 | * | ** |
| 193 | *** | *** |
| 194 | *** | *** |
| 195 | ** | ** |
| 196 | *** | *** |
| 197 | ** | ** |

TABLE 3-8

| | | |
|---|---|---|
| 198 | ** | *** |
| 199 | *** | *** |
| 200 | ** | ** |
| 201 | ** | ** |
| 202 | ** | ** |
| 203 | ** | ** |
| 204 | ** | ** |
| 205 | ** | ** |
| 206 | *** | *** |
| 207 | ** | ** |
| 208 | ** | ** |
| 209 | ** | ** |

The compounds of the present invention showed a similarly high antimalarial activity for both the drug resistant strain, K1 strain, and the drug sensitive FCR strain. The results show that the compounds of the present invention have excellent efficacy for inhibiting the growth of *Plasmodium* species.

Test Example 2: In Vivo Antimalarial Assay

In vivo antimalarial activity of the compound of the present invention was determined using a mouse model infected with rodent malaria *P. berghei* N strain (drug sensitive strain) by slightly modifying the method described in the above publication of Otoguro et al. (2001) and the method reported by Peters et al. (Peters, W., Portus, J. H. and Robinson, B. L.: The chemotherapy of rodent malaria. XXII. The value of drug-resistant strains of *P. berghei* in Screening for blood schizonticidal activity. Ann. Trop. Med. Parasitol., 69: 155-171, (1975)). The *P. berghei* N strain was generous gift from Dr. W. Peters (Northwick Park Institute for Medical Research, Middlesex, United Kingdom).

A group of three ICR male mice (Charles River Laboratories Japan, Inc.) weighing 18 to 20 g was used as a test animal. Using protozoa maintained and sub-cultured by in vivo passage, $2 \times 10^6$ parasite-infected erythrocytes were prepared, and the mice were infected therewith by tail vein injection. For the therapeutic test, a 1-day suppressive test was performed. The day of infection was defined as day 0. Two hours after the infection, a solution of the test compound (solvent: 3% DMSO/0.5% methylcellulose400-solution or suspension) was administered intraperitoneally (i.p.) once to 3 times. On day 4, blood smear preparation was prepared by collecting from the tail vein and the ratio of parasite-infected erythrocytes (parasitaemia) was investigated to determine the therapeutic effect (inhibition percentage) based on the infection rate of the group to which the compound was not administered. The significance test was performed by Dunnett's test.

In vivo antimalarial activities of representative compounds of the present invention are shown in Table 4.

TABLE 4

| Tested Conpound Example No. | Dosage Amount | Therapeutical Effect (%) inhibition | Significant Difference |
| --- | --- | --- | --- |
| 28 | 10 mg/kg | 51.4 | P = 0.0055 |
| 32 | 10 mg/kg | 47.5 | P = 0.0636 |
| 34 | 10 mg/kg | 51.5 | P = 0.0135 |
| 68 | 10 mg/kg | 41.7 | P = 0.0656 |
| 93* | 3 mg/kg | 64.2 | P = 0.0005 |
| 94 | 3 mg/kg | 42.9 | P = 0.0182 |
| 105 | 10 mg/kg | 41.9 | P = 0.0059 |
| 106** | 10 mg/kg | 87.4 | P = 0.0008 |
| 114 | 10 mg/kg | 70.9 | P < 0.0001 |
| 142** | 10 mg/kg | 84.5 | P < 0.0001 |
| 147* | 10 mg/kg | 83.4 | P = 0.0227 |
| 161* | 10 mg/kg | 64.3 | P = 0.0022 |
| 165* | 10 mg/kg | 98.0 | P = 0.0004 |
| 170 | 10 mg/kg | 92.9 | P = 0.0006 |
| 174* | 10 mg/kg | 93.6 | P = 0.0029 |

*Administered twice (day 0 and 1)
**Administered three times (day 0, 1 and 2)

The compounds of the present invention significantly suppressed the parasitaemia with 50% inhibition in a mouse model infected with rodent malaria *P. berghei* N strain compared with the vehicle control group when injected i.p. at 3 or 10 mg/kg once or twice, showing therapeutic effect. The results suggest that the effective dose 50 ($ED_{50}$) of the compounds of the present invention is about 3 to 10 mg/kg, indicating the compounds have excellent efficacy as a therapeutic agent for *plasmodium* infection at low doses.

INDUSTRIAL APPLICABILITY

The compound of the present invention is useful as an agent for treating, preventing and/or inhibiting propagation of infection with human infectious *Plasmodium* such as *Plasmodium falciparum, Plasmodium vivax, Plasmodium malariae, Plasmodium ovale* and *Plasmodium knowlesi*. The compound of the present invention is also useful for treating, preventing and inhibiting propagation of infection with *Plasmodium* resistant to existing antimalarials such as chloroquine and fansidar. The compound may also be used as an agent for inhibiting growth of *Plasmodium* in the form of a reagent for experiment and research.

The invention claimed is:

1. A compound of the formula (I):

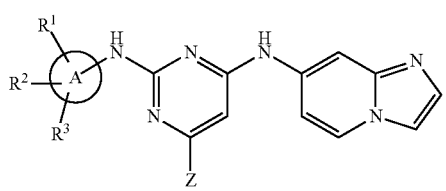

(I)

wherein the ring A is a 6-membered heteroaryl group having one or more nitrogen atom(s) optionally substituted with $R^1$, $R^2$ and $R^3$;

Z is an optionally substituted alkoxy group, an optionally substituted amino group, an optionally substituted heterocyloalkyl group or an optionally substituted heteroaryl group; and $R^1$, $R^2$ and $R^3$ are independently selected from the group consisting of a hydrogen atom, a halogen atom, an optionally substituted alkyl group, an optionally substituted cycloalkyl group, an optionally substituted alkoxy group, an optionally substituted cycloalkyloxy group, an optionally substituted heterocycloalkyloxy group, an optionally substituted phenoxy group, an optionally substituted amino group, a nitro group and a hydroxy group;

or pharmaceutically acceptable salt thereof.

2. The compound according to claim 1, wherein the ring A is an optionally substituted 6-membered heteroaryl group containing a nitrogen atom or pharmaceutically acceptable salt thereof.

3. The compound according to claim 1, wherein the ring A is an optionally substituted 6-membered heteroaryl group containing two nitrogen atoms or pharmaceutically acceptable salt thereof.

4. The compound according to claim 1, wherein the group of

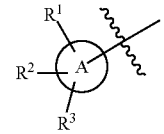

is a heteroaryl group selected from the group consisting of

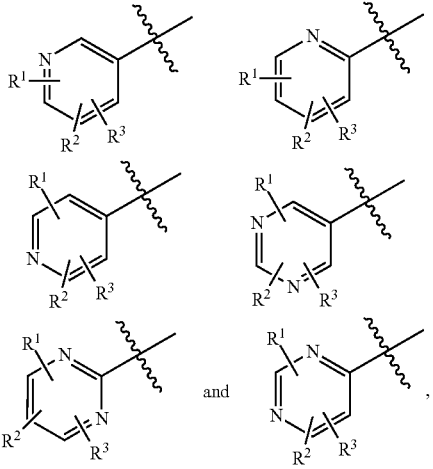

or pharmaceutically acceptable salt thereof.

5. A pharmaceutical composition comprising the compound according to claim 1 or pharmaceutically acceptable salt thereof, and a pharmaceutically acceptable carrier.

6. A therapeutic agent for treating infection diseases of malaria *plasmodium*, comprising the compound according to claim 1 or a pharmaceutically acceptable salt thereof.

* * * * *